United States Patent
Krueger et al.

(10) Patent No.: US 12,272,432 B2
(45) Date of Patent: Apr. 8, 2025

(54) BLOCKCHAIN-BASED DISTRIBUTION OF MEDICAL DATA RECORDS

(71) Applicant: Siemens Healthcare GmbH, Erlangen (DE)

(72) Inventors: Benedikt Krueger, Ebensfeld (DE); Robert James Taylor, San Francisco, CA (US)

(73) Assignee: Siemens Healthineers AG, Forchheim (DE)

( * ) Notice: Subject to any disclaimer, the term of this patent is extended or adjusted under 35 U.S.C. 154(b) by 642 days.

(21) Appl. No.: 17/263,593

(22) PCT Filed: Jun. 7, 2019

(86) PCT No.: PCT/EP2019/064965
§ 371 (c)(1),
(2) Date: Jan. 27, 2021

(87) PCT Pub. No.: WO2020/025202
PCT Pub. Date: Feb. 6, 2020

(65) Prior Publication Data
US 2021/0375408 A1 Dec. 2, 2021

(30) Foreign Application Priority Data

Aug. 3, 2018 (EP) .................................. 18187291

(51) Int. Cl.
*G06Q 20/40* (2012.01)
*G06F 16/955* (2019.01)
(Continued)

(52) U.S. Cl.
CPC ......... *G16H 10/60* (2018.01); *G06F 16/9566* (2019.01); *G06F 21/6245* (2013.01); *G06Q 20/401* (2013.01); *G06Q 2220/00* (2013.01)

(58) Field of Classification Search
CPC ................... G06Q 20/00–425; H04L 9/00–50
See application file for complete search history.

(56) References Cited

U.S. PATENT DOCUMENTS

| 10,025,941 B1 | 7/2018 | Griffin et al. |
| 2009/0037224 A1 | 2/2009 | Raduchel |

(Continued)

FOREIGN PATENT DOCUMENTS

| CN | 101742960 A | 6/2010 |
| CN | 102693357 A | 9/2012 |

(Continued)

OTHER PUBLICATIONS

Jia, Bokang et al.: "Opus—Decentralized music distribution using InterPlanetary File Systems (IPFS) on the Ethereum blockchain V0.8.3" 2016/2017; https://opus-foundation.org/whitepaper.pdf.

(Continued)

*Primary Examiner* — Ari Shahabi
(74) *Attorney, Agent, or Firm* — Harness, Dickey & Pierce, P.L.C.

(57) ABSTRACT

A method is for providing a uniform resource locator. In an embodiment, the method includes receiving a medical data record via an interface, the medical data record being related to a patient; determining the uniform resource locater related to the medical data record via a computation unit, the uniform resource locator including an authorization token based on the medical data record, the medical data record being accessible by following the uniform resource locator; and providing the uniform resource locator with the interface to the patient. By providing a uniform resource locator of an embodiment including an authorization token, access to the medical data record can be granted fast and efficient, e.g. by a patient forwarding the uniform resource locator to another entity (e.g. a physician), while at the same time (Continued)

non-authorized entities cannot access the medical data record due to their lack of the suitable authorization token.

10 Claims, 12 Drawing Sheets

(51) Int. Cl.
*G06F 21/62* (2013.01)
*G16H 10/60* (2018.01)

(56) References Cited

U.S. PATENT DOCUMENTS

| | | | |
|---|---|---|---|
| 2013/0006865 A1* | 1/2013 | Spates | H04L 9/083 705/50 |
| 2015/0332283 A1* | 11/2015 | Witchey | G16H 10/60 705/3 |
| 2016/0098723 A1 | 4/2016 | Feeney | |
| 2017/0039330 A1* | 2/2017 | Tanner, Jr. | G06Q 20/065 |
| 2018/0341648 A1 | 11/2018 | Kakavand et al. | |
| 2019/0005268 A1 | 1/2019 | Gupta | |
| 2019/0294822 A1 | 9/2019 | Hennebert | |
| 2020/0358782 A1 | 11/2020 | Hager et al. | |

FOREIGN PATENT DOCUMENTS

| | | |
|---|---|---|
| CN | 204946108 U | 1/2016 |
| CN | 107578814 A | 1/2018 |
| FR | 3079323 A1 | 9/2019 |
| WO | WO 2015175722 A1 | 11/2015 |
| WO | WO 2016189488 A2 | 12/2016 |
| WO | WO 2017136643 A1 | 8/2017 |
| WO | WO 2018115992 A1 | 6/2018 |

OTHER PUBLICATIONS

"Opus"; http://opus-foundation.org/; https://web.archive.org/web/20171216153252/http://opus-foundation.org/; last accessed Jan. 14, 2021.

International Search Report PCT/ISA/210 and Written Opinion of the International Searching Authority PCT/ISA/237 for International Application No. PCT/EP2019/064965 dated Jun. 7, 2019.

Anonymous; "Distributed ledger—Wikipedia"; published: Jan. 7, 2017; XP055503017.

* cited by examiner

BLOCKCHAIN-BASED DISTRIBUTION OF MEDICAL DATA RECORDS

PRIORITY STATEMENT

This application is the national phase under 35 U.S.C. § 371 of PCT International Application No. PCT/EP2019/064965, which has an International filing date of Jun. 7, 2019, which designated the United States of America and which claims priority to European application number EP18187291.2, filed Aug. 3, 2018, the entire contents of each of which are hereby incorporated herein by reference.

FIELD

Embodiments of invention generally relate to a method and system for blockchain-based distribution of medical data records.

BACKGROUND

Medical data records, such as medical images, medical diagnosis or laboratory reports, are usually stored in the systems of the medical institutions (e.g. hospitals) that created the respective medical data record, which makes it difficult to access medical data records of a patient which are stored in a distributed way at different medical institutions.

A common solution for a better accessibility of such medical data records is to store them so that they can be accessed from the outside of the medical institution having generated the respective medical data record, for example within a cloud storage or within a webserver. In this case, it has to be ensured that the medical data records can only be accessed by authorized entities, in particular only by entities authorized by the patient the medical data record relates to.

SUMMARY

The inventors have discovered that a need of embodiments of the present invention is to provide a system for regulating access to medical data records, advantageously allowing for a compensation of the patient the medical data record relates to.

Embodiments of the present invention aim to improve upon or even solve the needs by a method for providing a uniform resource locator, a providing system, a computer program product and a computer-readable medium. Advantageous features and embodiments are contained in the claims and in the description.

In the following, embodiments of the invention are described with respect to systems, units and apparatuses as well as with respect to methods. Features, advantages or alternative embodiments herein can be assigned to the other corresponding objects and vice versa. In other words, the systems, units and apparatuses can be improved with features described or claimed in the context of the corresponding methods. In this case, the functional features of the method are embodied by objective units of the systems, units and apparatuses.

Furthermore, embodiments of the invention are described with in context of different methods, systems, units and apparatuses corresponding to different possible aspects of the invention. It has to be understood that advantageous embodiments and features of any object described in the context of one method, system, unit or apparatus can also be advantageous embodiments and features of the same object for other methods, systems, units and apparatuses.

In particular, embodiments of the invention are described in context of methods and systems for providing a uniform resource locator, for providing a location information and for storing consent. It has to be understood that advantageous embodiments and features of these methods and systems can also be advantageous embodiments and features of the other methods and systems.

In particular, embodiments of the invention are furthermore described in context of methods and systems for using a uniform resource locator, for providing a location information and for using consent information. It has to be understood that advantageous embodiments and features of these methods and systems can also be advantageous embodiments and features of the other methods and systems.

Furthermore, it has to be understood that the methods and systems for using an object provided or created by another method or system can always be extended with steps and/or components of the another method or system. In other words, methods or systems for providing and/or creating an object and methods or systems for using the object can always be combined into a joint method or system of creating and using the object.

In one embodiment, the invention relates to a method for providing an uniform resource locator, comprising the step of receiving a medical data record with an interface, wherein the medical data record is related to a patient, the step of determining the uniform resource locater related to the medical data record with a computation unit, wherein the uniform resource locator comprises an authorization token based on the medical data record, and wherein the medical data record can be accessed by following the uniform resource locator, and the step of providing the uniform resource locator with the interface to the patient.

In another embodiment, the invention relates to a method for using a uniform resource locator provided by a method for providing a uniform resource locator, comprising the step of receiving an access request directed to a requested medical data record by an interface, wherein the requested medical data record is stored within a memory unit, wherein the access request is based on the uniform resource locator, and comprising the step of providing the requested medical data record based on the access request with the interface. It is not essential for the invention that the medical data record is provided, and it is not essential for the invention that the access request is based on the uniform resource locator.

In another embodiment, the invention relates to a providing system for providing a uniform resource locator, comprising:
  an interface, configured for receiving a medical data record, wherein the medical data record is related to a patient, and furthermore configured for providing the uniform resource locator to the patient, and
  a computation unit, configured for determining the uniform resource locator related to the medical data record, wherein the uniform resource locator comprises an authorization token based on the medical data record, and wherein the medical data record can be accessed by following the uniform resource locator.

In a particular embodiment, the providing system for providing a uniform resource locator can be configured to execute the method for providing a uniform resource locator according to the invention and its embodiments. The providing system is configured to execute the method and its aspects by its interface and its computation unit being configured to execute the respective method steps.

In another embodiment, the invention relates to a computer program product comprising a computer program, the computer program being loadable into a memory unit of a providing system, including program code sections to make the providing system execute the method for providing a uniform resource locator according to an embodiment of the invention when the computer program is executed in the providing system.

In a further possible embodiment, the invention relates to a computer-readable medium, on which program code sections of a computer program are saved, the program code sections being loadable into and/or executable in a providing system to make the providing system execute the method for providing a uniform resource locator according to an embodiment of the invention when the program code sections are executed in the accessing system.

The realization of embodiments of the invention by a computer program product and/or a computer-readable medium has the advantage that already existing providing systems can be easily adopted by software updates in order to work as proposed by embodiments of the invention.

In a further possible embodiment, the invention relates to usage system for using a uniform resource locator provided by a method for providing the uniform resource locator according to the invention or one of its embodiments, comprising:
   an interface, configured for receiving an access request directed to a requested medical data record, wherein the requested medical data record is stored within a repository, wherein the access request is based on the uniform resource locator, furthermore configured for providing the requested medical data record based on the access request, and
   an computation unit.

In a further possible embodiment, the invention relates to a computer program product comprising a computer program, the computer program being loadable into a memory unit of an usage system, including program code sections to make the usage system execute the method for using a uniform resource locator according to an embodiment of the invention when the computer program is executed in the usage system.

In a further possible embodiment, the invention relates to a computer-readable medium, on which program code sections of a computer program are saved, the program code sections being loadable into and/or executable in an usage system to make the usage system execute the method for using a uniform resource locator according to an embodiment of the invention when the program code sections are executed in the usage system The realization of embodiments of the invention by a computer program product and/or a computer-readable medium has the advantage that already existing accessing systems can be easily adopted by software updates in order to work as proposed by embodiments of the invention.

BRIEF DESCRIPTION OF THE DRAWINGS

The properties, features and advantages of this invention described above, as well as the manner they are achieved, become clearer and more understandable in the light of the following description and embodiments, which will be described in details in the context of the drawings. This following description does not limit the invention on the contained embodiments. Same components or parts can be labeled with the same reference signs in different figures. Spaces in uniform resource locators and file locations are not relevant and only for better readability. In general the figures are not for scale. In the following.

DETAILED DESCRIPTION OF THE EXAMPLE EMBODIMENTS

Figure 1:
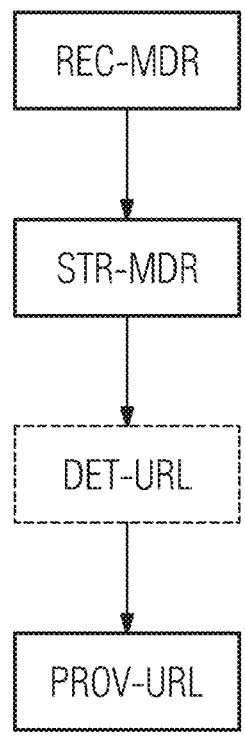
FIG. 1 displays a first embodiment of the method for providing a uniform resource locator, FIG. 2 displays a second embodiment of the method for providing a uniform resource locator, FIG. 3 displays an embodiment of data blocks of the distributed consent ledger, FIG. 4 displays an embodiment of data blocks of the distributed ownership ledger, FIG. 5 displays a flowchart of an embodiment a method for storing a medical data record in a repository.

In one embodiment, the invention relates to a method for providing an uniform resource locator, comprising the step of receiving a medical data record with an interface, wherein the medical data record is related to a patient, the step of determining the uniform resource locater related to the medical data record with a computation unit, wherein the uniform resource locator comprises an authorization token based on the medical data record, and wherein the medical data record can be accessed by following the uniform resource locator, and the step of providing the uniform resource locator with the interface to the patient.

In particular, the interface can be the interface of a providing system. In particular, the computation unit can be the computation unit of the providing system. In particular, the providing system can furthermore comprise a memory unit. In particular, the providing system can comprise a patient client and/or a server, wherein the interface can be the interface of the patient client and/or of the server, wherein the computation unit can be a computation unit of the patient client and/or of the server, and wherein the memory unit can be a memory unit of the patient client and/or of the server.

In general, a medical data record comprises medical data related to a patient. The medical data record can comprise a medical image dataset. Such medical image dataset is acquired from the patient using a medical imaging apparatus, e.g. a magnetic resonance (an acronym is "MR") apparatus, a single-photon emission tomography (an acronym is "SPECT") apparatus, a positron emission tomography (an acronym is "PET") apparatus, a computed tomography (an acronym is "CT") apparatus, an ultrasound apparatus, an X-ray apparatus, a C-arm apparatus or a combined medical imaging apparatuses formed by any combination composed of the aforementioned imaging modalities. The medical image dataset can also comprise automatically, semi-automatically or manually generated processing information, such as segmented organs, contour information, registration information, etc.

The medical data record can also comprise medical data acquired or derived from other medical apparatuses which are not medical imaging apparatuses. Such other medical apparatuses can e.g. be a treatment apparatus, e.g. a radiotherapy device, a lithotripsy device, a laser treatment device, an infusion pump or an interventional treatment device. The medical data can also stem from an apparatus for intensive medicine, a mobile monitoring device, a respiratory device, an anesthetic machine, an ECG (acronym for electrocardiography) device, an EEG (acronym for electroencephalography) device, a blood pressure measurement device, an infusion device or a dialysis device. The medical data record can also comprise laboratory diagnostics or genetic information.

The medical data record can also comprise a complete or part of an electronic health record of a patient. Therefore, the medical data record can comprise information about a disease history of the patient. The medical data record can also contain annotation information, which describes automatically, semi-automatically or manually generated diagnostic findings in the medical dataset. The medical data record can also comprise demographic metadata related to the patient, such as gender, age, weight, size, etc.

Other medical data which can be considered by those skilled in the art can also be part of the medical data record. In particular, also a link to a medical data record or a hash value of a medical data record can be considered as medical data record.

In general, a uniform resource locator (acronym "URL") is a reference to a resource that specifies the location of the resource on a computer network and a mechanism for retrieving it. In particular, the uniform resource locator is a reference to the medical data record. The terms "uniform resource locator" and "web address" can be used as synonyms.

The usage of a uniform resource locator is not essential for the invention, in particular, any kind of string for identifying and/or locating an abstract or a physical resource can be used, e.g. a uniform resource identifier (acronym "URI") or an international resource identifier (acronym "IRI"). In particular, the terms "uniform resource identifier" or "international resource identifier" can replace the term "uniform resource locator" throughout the description and the claims.

In particular, the uniform resource locator can be used for accessing the medical data record. In particular, the uniform resource locater can be contained in a hyperlink of an electronic document, in particular in a hyperlink of an e-mail or in a hyperlink of a website, wherein both the e-mail and the website can be defined in terms of a text document e.g. using the HTML (acronym for "Hypertext Markup Language") standard. If the uniform resource locator is contained in a hyperlink, the medical data record can be accessed by following the hyperlink.

The term "uniform resource locator" in this application can also be understood as being a request based on a uniform resource locator. In particular, the term "uniform resource locator" can be replace with "request based on a/the uniform resource locator". Such a request based on a uniform resource locator can comprise further data, wherein in particular the further data is sent to a server characterized and/or identified by the uniform resource locator. In particular, a request is a request based on a communication protocol of the application layer, e.g. of the Internet Protocol Suite or the OSI model. In particular, a request based on a uniform resource locator is a HTTP request (acronym for "Hypertext Transfer Protocol"), a HTTPS request (acronym for "Hypertext Transfer Protocol Secure") or an FTP request comprising the uniform resource locator.

In general, the authorization token is a component of the uniform resource locator, wherein the presence of the authorization token in the URL and/or submitting the authorization token with the URL is a necessary condition to access the medical data record. In particular, the authorization token can be a string contained in the URL, in particular within the path part or the query part of the URL.

If the uniform resource locator is understood as a request based on a uniform resource locator, the authorization token can be part of the further data sent to the server characterized and/or identified by the uniform resource locator. In particular, if the uniform resource locator is understood as an HTTP POST request, the authorization token can be contained in the data submitted by the HTTP POST request.

In general, the authorization token can be specific to the medical data record, which means that everybody having access to the uniform resource locator can access the medical data record. For example, the authorization token can comprise the location of the medical data record within the server. In particular, if the server does not provide a list with medical data records stored in the server, the knowledge of the authorization token is necessary to access the medical data record. Alternatively, the authorization token can also be specific to an authorized entity entitled to access the medical data record. In particular, different authorization tokens can be used for different authorized entities entitled to access the medical data record. This can be used for tracking access to the medical data record. Alternatively, the authorization token can also be specific to the medical data record and to an authorized entity entitled to access the medical data record, combining the advantages of both approaches.

Instead of the term "authorized entity" the term "accessing entity" can be used, indicating that an authorized entity is allowed or entitled to access the respective medical data record.

The inventors recognized that by providing a uniform resource locator comprising an authorization token access to the medical data record can be granted fast and efficient, e.g. by a patient forwarding the uniform resource locator to another entity (e.g. a physician), while at the same time non-authorized entities cannot access the medical data record due to their lack of the suitable authorization token.

According to a further embodiment of the invention, the method for providing a uniform resource locator comprises the step of storing the medical data record with a memory unit, wherein the uniform resource locator comprises the location of the medical data record in the memory unit. In particular, the memory unit can be a web server or web storage (in particular a cloud storage). In particular, the medical data record is stored within a repository within the memory unit. In particular, the repository is a part of the memory unit of the providing system or stored within the memory unit of the providing system, and in particular, the repository is a part of the memory unit of the server of the providing system or stored in the memory unit of the server of the providing system.

In particular, the location of the medical data record is contained in the path part of the URL, and in particular, the memory unit and/or the server and/or the repository are contained in the host part of the URL. Alternatively, the uniform resource locator can comprise the location of the medical data record as a query parameter.

If the term uniform resource locator is understood being a request based on a uniform resource locator, in particular a HTTP POST request, it is to be understood that the uniform resource locator comprises the location of the medical data record also if the location of the medical data record is contained in the further data sent to the server characterized and/or identified by the uniform resource locator.

The location of the medical data record can correspond to the location of the medical data record in the filesystem of the memory unit or in the filesystem of the server or in filesystem of the repository of the server. Alternatively, the location of the medical data record can be a number or a string which can be mapped to the location of the medical data record in the filesystem of the memory unit or in the filesystem of the server or in filesystem of the repository of the server via a table (e.g. a hashtable). In particular, the mapping is executed by the server.

In particular, the location of the medical data record can comprise the authentication token, or the authentication token can comprise the location of the medical data record. In particular, the location of the medical data record can be identical with the authentication token.

The inventors recognized that by storing the medical data record in the memory unit, in particular within the server or within the repository the availability of the medical data record can be improved.

According to a further embodiment of the invention, the method for providing a uniform resource locator comprises the step of receiving an identifier of an authorized entity with the interface, wherein the authorized entity is allowed to access the medical data record, and wherein the uniform resource locator is based on the identifier of the authorized entity. In particular, the uniform resource locator is based on the identifier of the authorized entity by the authorization token being based on the identifier of the authorized entity.

In general an entity can be a person, a group of person, a legal entity (such as a company), a group of legal entities, or an object, in particular an information technology object as a server, a client, a storage medium, or a computer. In particular, an entity can be a medical professional like an employee of a hospital, a physician, a nurse or technical staff of a hospital, or any group thereof. In particular, an entity can be a hospital, a medical practice, or any group thereof. Furthermore an entity can also be a medical research facility or a medical researcher. An authorized entity is an entity authorized to access the medical data record.

An identifier of authorized entity can generally be used to unambiguously identify the authorized entity. In particular, if the entity is a person accessing the medical data record, the identifier of the entity can comprise the name of the person accessing the medical data record, the data of birth of the person accessing the medical data record, an ID of the person accessing the medical data record (e.g. the social insurance number, the ID number, a driving license number, or a passport number) and/or the employer of the person accessing the medical data record. In particular, if the entity is a company (e.g. a hospital), the identifier of the identity can comprise the company name. In particular, the identifier of the entity accessing the medical data record can comprise the IP address of a computer used by the entity accessing the medical data record. In particular, the identifier of the entity accessing the medical data record can be based on a public key or on a private key related with the entity accessing the medical data record. In particular, the identifier of the authorized entity can also be a shared secret or token, which is known both by the authorized entity and a system granting access to the medical data record.

In particular, the uniform resource locator and/or the authentication token can be based on the identifier of the authorized entity by the uniform resource locator and/or the authentication token comprising the identifier of the authorized entity as substring.

The inventors recognized that by including the identifier of an authorized entity into the uniform resource locator it is possible to track based on the uniform resource locator which entity has accessed the medical data record. Furthermore, it is possible to differentiate the access of several authorized entities, for example by granting access to a first authorized entity for a longer timespan than for a second authorized entity.

According to a further embodiment of the invention, the identifier of the authorized entity is based on a digital certificate. In particular, the identifier of the authorized entity is a digital certificate or a part of a digital certificate. In particular, the digital certificate is signed by a certificate authority.

Other terms for "digital certificate" are "public key certificate" or "identity certificate". The digital certificate can be an electronic document relating to the ownership of a public key, in particular to the ownership of the authorized entity. The access certificate therefore usually contains information about the public key and the authorized entity related to this public key. Furthermore, the access certificate typically comprises a digital signature which verifies the certificate's content. In particular the digital signature is based on a private key related to a parent digital certificate. The digital certificate is the to be signed by a certificate authority if the certificate authority issues the digital signature using a private key of the certificate authority (which typically is the private key of the parent digital certificate). The validity of a certificate can be proven using the public key corresponding to the private key of the certificate authority (or equivalently, based on another digital certificate certifying the certificate authority).

The inventors recognized that by using digital certificates as identifiers of authorized entities the security of the access to the medical data record can be increased, because the digital certificate is a proof of identity of the authorized entity.

According to a further embodiment of the invention, the method for providing a uniform resource locator comprises the step of determining consent information with the computation unit, wherein the consent information is related to the consent of the patient to the use of the medical data record by the authorized entity, wherein the consent information is based on the medical data record and/or on the identifier of the authorized entity, and the step of documenting the consent information in a distributed consent ledger with the computation unit.

A distributed consent ledger is a distributed ledger. In general, a distributed ledger is a certain type of a decentralized database. In particular, the distributed ledger is distributed in the sense that there are several copies of (at least parts of) the distributed ledger in different memory units, wherein the memory units are spatially distributed. The distributed ledger comprises multiple records, wherein the multiple records can be identified with database entries. In particular, the multiple records are organized as data blocks. In particular, the records are created by different entities, in particular different nodes of a network, and stored with the different entities, in particular within the different nodes if the records. In other words, the construction and maintenance of the records is typically not performed by a central authority, but independently by nodes of the network. In typical cases, all nodes of the network maintain one copy of the distributed ledger.

In general, updating the distributed ledger is typically based on a consensus mechanism, wherein a consensus mechanism ensures that the different copies of the distributed ledger match, also in the cases of a delayed communication between the entities storing the copies of the distributed ledger.

In particular, documenting consent information in the distributed consent ledger is executed by storing the consent information, a link to the consent information and/or a hash of the consent information in the distributed consent ledger In particular, storing data in a distributed ledger can comprise appending a further data block to the distributed ledger, wherein the further data block comprises the data to be stored. Appending a further data block to the distributed ledger can comprise executing the consensus mechanism, wherein executing the consensus mechanism can comprise a proof of work, a proof of storage, a proof of stake, and/or a proof of elapsed time. A proof of work can be a compute-bound proof of work, a network-bound proof of work and/or a memory-bound proof of work.

In particular, the consent information can be based on the medical data record and on the identifier of the authorized entity, in this case, the consent information can encode the patient's consent to the authorized entity using the medical data record. In particular, the consent information can be based on the medical data record, and not on the identifier of the authorized entity, in this case, the consent information can encode the patient's consent to any entity using the medical data record. In particular, the consent information can be based on the identifier of the authorized entity, and not on the identifier of the medical data record, in this case, the consent information can encode the patient's consent to the authorized entity using all medical data records related to the patient. In particular, the consent information can comprise a smart contract.

The inventors recognized that by documenting consent information in a distributed consent ledger the consent of the patient to the use of the medical data record by the authorized entity can be stored in a revision-safe and manipulation-safe way.

According to a further embodiment of the invention, the method for providing a uniform resource locator comprises receiving a first identifier of the patient with the interface, wherein the consent information is furthermore based on the first identifier of the patient.

In particular, the first identifier of the patient is an identifier of the patient. In particular, there can be a second identifier of the patient being an identifier of the patient, wherein the second identifier of the patient can be identical with the first identifier of the patient, or wherein the second identifier of the patient and the first identifier of the patient can be different.

In particular, an identifier of the patient is based on a key pair of the patient comprising a public key and a private key. The identifier of the patient can comprise the public key and/or the private key. In particular, the identifier is denoted as related to a public key, if it comprises the public key and/or if it comprises the private key associated with the public key. In particular, the identifier is denoted as related to a private key, if it comprises the private key and/or if it comprises the public key associated with the private key. An identifier of the patient can be used for signing a dataset, in particular, a private key contained in the identifier of the patient or related to the identifier of the patient can be used for signing the dataset.

In general, the identifier of a patient can be transferred from the patient to another entity, if the identifier of the patient comprises a public key, but not an associated private key. The identifier of the patient can also be transferred to another entity, if the identifier of the patient comprises a private key, in this case, this identifier of the patient should not be used again afterwards.

The inventors recognized that by the consent information being based on a first identifier of the patient a manipulation of the consent information can be made more difficult, in particular, it can be ensured that the consent information is actually issued by the patient itself.

According to a further embodiment of the invention, the consent information comprises a consent signature based on the medical data record and/or based on the identifier of the authorized entity, wherein the consent signature is signed based on the first identifier of the patient. In particular, the first identifier of the patient comprises a first private key related to the patient, and the consent signature is signed based on the first identifier of the patient by being signed with the first private key contained in the first identifier of the patient.

In particular, the consent signature is a digital signature. In general a digital signature relies on an asymmetric key pair comprising a private key and a public key, originating from an asymmetrical cryptography system. A public key is corresponding with a private key or vice versa, if the private key and the public key form an asymmetric key pair.

In particular, a digital signature is the output of a signing algorithm, wherein the signing algorithm takes as first input the data to be signed (also denoted as "message") and as second input a signing information. In particular, the signing information is a private key. In particular, a signature is signed with a private key, if the private key was used as second input for the signing algorithm when creating the signature. In particular, a signature is based on certain data, if the certain data was used as first input for the signing algorithm when creating the signature.

In particular, for a signing algorithm there exists a signature verifying algorithm, wherein the signature verifying algorithm takes as input a dataset, a signature and a public key, and wherein the output of the signature verifying algorithm determines whether the given signature is the output of the signing algorithm applied to the dataset with a private key corresponding to the given public key.

In particular, the signature verifying algorithm can verify the validity of a signature without the knowledge of the private key corresponding to the public key. In particular, a private key used to sign a signature cannot be deduced from the signature.

The inventors recognized that by using a signature signed based on a first identifier of the patient it can undeniably be documented that the consent information was issued and/or confirmed by the patient, so that the level of data protection can be increased.

According to a further embodiment of the invention, the method for providing a uniform resource locator comprises the step of receiving usage information with the interface, wherein the consent information is furthermore based on the usage information.

In general the usage information is related to the kind of usage of the medical data record allowed by the patient. In other words, the usage information is related to the kind of usage of the medical data record the patient consents with. In general terms, the usage information describes how the medical data record may be used.

The inventors recognized that by usage information being included into the consent information it can be documented in a revision-safety way to which possible uses of its data the patient consented.

According to a further embodiment of the invention, the method for providing a uniform resource locator comprises the step of receiving a second identifier of the patient with the interface, the step of determining ownership information with the computation unit, wherein the ownership information comprises an ownership signature based on the medical data record, wherein the ownership signature is signed based on the second identifier of the patient, and the step of documenting the ownership information in a distributed ownership ledger with the computation unit. In particular, the second identifier of the patient comprises a second private key related to the patient, and the ownership signature is signed based on the second identifier of the patient by being signed with the second private key contained in the second identifier of the patient.

In particular, the second identifier of the patient is an identifier of the patient. In particular, the second identifier of the patient can be identical with the first identifier of the patient, alternatively, the second identifier of the patient can comprise the first identifier of the patient, alternatively, the first identifier of the patient can comprise the second identifier of the patient. In particular, the distributed ownership ledger can be identical with the distributed consent ledger, alternatively one of the two distributed ledgers can comprise the other one of the two distributed ledgers.

The inventors recognized that by documenting the ownership information in a distributed ownership ledger it can be documented undeniably that a certain medical data record is related to a patient, e.g. for assigning royalties to a patient. In particular, if the first identifier of the patient and the second identifier of the patient are different (e.g. if they are based on a first asymmetric key pair and a different second asymmetric key pair), there is no relation between the consent information and the ownership information, which makes relating the medical data record to a patient harder for an external entity.

According to a further possible embodiment of the invention, the consent information comprises a first hash of the medical data record, and the ownership information comprises a second hash of the medical data record, wherein the first hash of the medical data record and the second hash of the medical data record are different. In particular, the first hash of the medical data record can be calculated with a first hash function, and the second hash of the medical data record can be calculated with a second hash function, wherein the first hash function and the second hash function are different. In particular, the first hash of the medical data record can be based on a hash function with a first seed, and the second hash of the medical data record can be based on a hash function with a second seed, wherein the first seed and the second seed are different.

The inventors recognized that by using different hashes in the consent information and the ownership information, the consent information and the ownership information cannot be associated to each other by an external party, increasing the data privacy because the accumulation of metadata is made more difficult.

According to a further possible embodiment of the invention, the consent information comprises a first hash of the medical data record, and the ownership information comprises a second hash of the medical data record, wherein the second hash is based on a combination of the medical data record and of other data. In particular, the other data can be protected health information (an acronym is "PHI") of the patient. In particular, the other data is data only known to the patient.

The inventors recognized that by using different hashes in the consent information and the ownership information, the consent information and the ownership information cannot be associated to each other by an external party, increasing the data privacy because the accumulation of metadata is made more difficult. Furthermore, by using other data which is only known to the patient, the patient can prove its ownership using the other data.

According to a further possible embodiment of the invention, the method for providing an uniform resource locator comprises a step of unlocking access to the medical data record with the computation unit, wherein the step of unlocking access to the medical data record is executed after the step of documenting the consent information in the distributed consent ledger and/or after the step of documenting the ownership information in the distributed ownership ledger.

The inventors recognized that by allowing access to the medical data record only after documenting the consent information and/or the ownership information in the respective distributed ledger, fraudulent consent information and/or the ownership information documented in the respective ledger by another entity can be detected due to the existence of earlier consent information and/or ownership information.

According to a further embodiment of the invention, the consent information comprises a smart contract, wherein the smart contracts regulates a transfer of cryptocurrency in the event of a usage of the medical data record, wherein the cryptocurrency is transferred from a first account to a second account,
  wherein the first account is related to an entity using the medical data record, and wherein the second account is related to the first identifier of the patient and/or to the second identifier of the patient.

In general a cryptocurrency is a digital asset or a digital medium which can be exchanged between different entities, wherein methods of cryptography are used for transferring cryptocurrencies from a first entity to a second entity, for the creation of a new amount of cryptocurrency and/or for verifying transfers of cryptocurrency from a first entity to a second entity. As an alternative term for "cryptocurrency" the term "virtual currency" can be used. In particular, a cryptocurrency is a digital currency. Cryptocurrency can be stored in accounts (another term is "wallet"), in particular, an account corresponds to a asymmetric key pair comprising a private key and a public key, wherein the private key must be used for transferring cryptocurrency from the account to another account, and wherein the public key must be used for transferring cryptocurrency from another account to the account. In particular, an account can be identified by the public key.

In general, a smart contract comprises program elements which can be executed by a server, a client, or any other computation node. In particular, the program elements can comprise program logic, source code, scripting language and/or compiled machine code. In particular, a smart contract is documented in a distributed ledger, in particular in a distributed ownership ledger or in a distributed consent ledger. In particular, a smart contract can comprise conditions in terms of program logic, and consequences in terms of program logic, wherein the consequences are activated or executed if certain conditions are fulfilled.

In general, transferring a certain amount of cryptocurrency from a first account to a second account comprises creating a transaction log, wherein the first account corresponds to a asymmetric key pair comprising a first private key and a first public key, and wherein the second account corresponds to an asymmetric key pair comprising a second private key and a second public key, and wherein the transaction log comprises the second public key and at least one key of the first private key and the first public key, and wherein the transaction log furthermore comprises the amount of cryptocurrency being transferred. In particular, a transaction log can also comprise a signature based on the amount of cryptocurrency being transferred and the second public key, signed with the first private key.

In particular, transferring a certain amount of cryptocurrency is executed by including the transaction log into a data block of the distributed ledger or another distributed ledger.

The inventors recognized that by transferring cryptocurrency an efficient payment process for usage of the medical data record can be initiated, while not disclosing the identity of the patients related to the medical data record.

According to further possible embodiment of the invention the distributed consent ledger and/or the distributed owner ledger comprises data blocks.

In general, data blocks are the elementary data records of the ledger. In particular, a data block is an immutable data structure, which means that a data block cannot be changed or modified. This implies that changes to the ledger can only be performed by adding or removing data blocks. In particular, the immutability of a data block can be ensured by storing a hash value of the data block within the data block or outside the data block.

The inventors recognized that using a distributed consent ledger and/or the distributed owner ledger comprising data blocks different copies of the distributed consent ledger and/or the distributed owner ledger can be synchronized more efficiently. In particular, using immutable data blocks it can be made harder for someone to manipulate the distributed consent ledger and/or the distributed owner ledger.

According to a further possible embodiment of the invention, a first data block of the distributed consent ledger comprises a link information related to a second data block of the distributed consent ledger, and/or a first data block of the distributed ownership ledger comprises a link information related to a second data block of the distributed ownership ledger. In particular, the first data block and the second data block can be identical. In particular, each of the data blocks of the distributed consent ledger comprises a link to a data block of the distributed consent ledger, and/or each of the data blocks of the distributed ownership ledger comprises a link to a data block of the distributed ownership ledger.

In particular, a first data block of the distributed consent ledger and a second data block of the distributed consent ledger can be linked, and/or a first data block of the distributed ownership ledger and a second data block of the distributed ownership ledger can be linked. This link can be an undirected or a directed link. In particular, a link of the first data block and the second data block is present, if the first data block comprises a link information related to the second data block and/or if the second data block comprises a link information related to the first data block. In particular, a link information can be a data integrity information. In particular, by inspecting the data integrity information related to the first data block a manipulation and/or altering of the first data block can be recognized or determined.

A common example for a link information related to a first data block is a hash of (at least parts) of the first data block, in particular, the hash of (at least parts) of the first data block may be stored in the second data block. Storing the hash of the first data block in the second data block allows verifying that the at least one of the data blocks was not altered after the determining of the hash, if it can be assumed that the hash contained in the second data block was not altered.

It is also possible that the data blocks of the distributed consent ledger and/or the distributed owner ledger comprise several link informations, in particular each of the further link informations can be a hash of another data block of the respective distributed ledger. It is possible that a link information contained in a data block of the distributed consent ledger and/or the distributed owner ledger is related to the data block, in particular, it is possible that the link information in a data block is identical with the hash of (at least parts) of the data block.

The inventors have recognized that by using link information in the data blocks the structure of the distributed consent ledger and/or the distributed owner ledger can be incorporated into the data blocks, so that the structure of the distributed ledger need not to be stored in an external and/or separate data item.

According to a further possible embodiment of the invention, a link information related to a second data block comprises a hash of the second data block.

In general a hash of a data block is the result of a hash function being applied to the data block, the result of a hash function being applied to a subset of information contained in the data block, or the result of a hash function being applied to a combination of a first subset of information contained in the data block and a second subset of information, wherein the second subset of information is a subset of information of the data block that contains or will contain the hash.

In general a hash function is a function that maps data of arbitrary size to data of a fixed size. In particular, the hash function is a cryptographic hash function. In particular, a cryptographic hash function is a deterministic function; in particular the output of the hash function does only depend on the input of the hash function. In particular, a cryptographic hash function can be calculated in a fast manner for all input values. In particular, a cryptographic hash function is only brute-force invertible, i.e. given the output of a cryptographic hash function it is only possible to calculate the corresponding input of the cryptographic hash function by calculating the cryptographic hash function for an large amount of input values (i.e. a brute-force attack). In other words, finding the input value corresponding to the output value of a cryptographic hash function is an intractable problem. In particular, finding a first input value and a second input value of a cryptographic hash function that lead to an identical output value is an intractable problem. In particular, a cryptographic hash function is scattering; i.e. even correlated inputs of the cryptographic hash function lead to uncorrelated outputs of the cryptographic hash function.

In particular, a hash function can calculate a Merkle root of the input data, in particular by computing hashes within a Merkle tree.

The inventors recognized that using a hash of a second data block as link information comprised by a first data block makes the second data block immutable, or at least changes or manipulations of the second data block can be determined by inspecting the first data block, in particular by comparing a hash calculated based on the second data block with the hash of the second data block stored in the first data block.

In another embodiment, the invention relates to a method for using a uniform resource locator provided by a method for providing a uniform resource locator, comprising the step of receiving an access request directed to a requested medical data record by an interface, wherein the requested medical data record is stored within a memory unit, wherein the access request is based on the uniform resource locator, and comprising the step of providing the requested medical data record based on the access request with the interface. It is not essential for the invention that the medical data record is provided, and it is not essential for the invention that the access request is based on the uniform resource locator.

In particular, the interface can be the interface of a usage system. In particular, the usage system can furthermore comprise a computation unit. In particular, the usage system can furthermore comprise a memory unit. In particular, the memory unit comprises a repository, and in particular, the requested medical data record is stored within this repository. In particular, the usage system can comprise a user client and/or a server, wherein the interface can be the interface of the user client and/or of the server, wherein the computation unit can be a computation unit of the user client and/or of the server, and wherein the memory unit can be a memory unit of the user client and/or of the server.

In particular, a requested medical data record is a medical data record. In particular, the requested medical data record is one of the medical data records stored within the memory unit.

In particular, the interface for receiving the access request is an interface of the server. In particular, the access request is sent to the interface of the server by an interface of a client, in particular by an interface of the user client. In particular, the medical data record is provided to the interface of the client, in particular to the interface of the user client. In particular, the client or the user client is a client or user client of an authorized entity and/or a requesting entity.

An access request is directed to a requested medical data record, if the access request specifies the requested medical data record as a medical data record to be retrieved. In particular, the access request is directed to a requested medical data record by the uniform resource locator comprising a location of the requested medical data record in a repository, in particular in a repository of the server. In particular, the access request can be based on the uniform resource locator by the access request being identical with the uniform resource locator, by the uniform resource locator comprising the access request, or by the access request comprising the uniform resource locator.

The inventors recognized that by this proposed method the requested medical data record can be provided to authorized entities or persons in an efficient but yet safe way.

According to a further possible embodiment of the invention, the step of providing the requested medical data record with the interface comprises sending the requested medical data record with the interface to the user client. The inventors recognized that by directly sending the requested medical data record to the user client the user client can very efficiently use (e.g. view or manipulate) the medical data record without any further interaction with the server.

According to a further possible embodiment of the invention, within the step of providing the requested medical data record, the requested medical data record is provided to the user client in a secured environment. For example, the requested medical data record is provided as read-only object within a website. In particular, only parts of the requested medical data records are provided to the user client (e.g. only rendered images, but not the raw imaging data). The inventors have recognized that by not sending the requested medical data record to the user client directly it can be ensured that the requested medical data record is only used by the user client and/or the requesting entity in a consented way. In particular, it is not possible for the user client and/or the requesting entity to store or distributed the requested medical data record. This enhances the data privacy of the proposed method.

According to a further possible embodiment of the invention, the step of providing the requested medical data record comprises the substep of receiving a trainable algorithm by the interface, the step of performing a training step for the trainable algorithm based on the requested medical data record by a computing unit, and the step of providing the trainable algorithm by the interface.

In general, a trainable algorithm is an algorithm mapping input data to output data based on an internal parameter, wherein the internal parameter can be adapted or modified by a training step. In particular, the trainable algorithm is a neural network (e.g. a deep neural network or a convolutional neural network), wherein the internal parameters of a neural network are the edge weights. In particular, adapting or modifying the internal parameter of a neural network can be executed via backpropagation.

The inventors recognized that by training the trainable algorithm based on the requested medical data record on the server the requested medical data record needs not to be transferred to the user client, so the user client and/or the requesting entity cannot unauthorized distribute the requested medical data record.

According to a further embodiment of the invention, the access request is initiated by a requesting entity, wherein consent information based on medical data records and on identifiers of authorized entities are documented in a distributed consent ledger, the method furthermore comprising the step of receiving an identifier of the requesting entity with the interface, and the step of performing a first check whether the distributed consent ledger documents a consent information based on the requested medical data record and on the identifier of the requesting entity with a computation unit, wherein the step of providing is only executed in case of a positive first check. In particular, the computation unit is a computation unit of the usage system, and in particular, the computation unit is a computation unit of the server.

In particular, the distributed consent ledger documents consent information if the distributed consent ledger comprises the consent information. In particular, the distributed consent ledger comprises the consent information, if one of the data blocks of the distributed consent ledger comprises the consent information. In particular, the consent information is based on the requested medical data record, if the consent information comprises the requested medical data record and/or if the consent information comprises a hash of the requested medical data record. In particular, the consent information is based on the identifier of the requesting entity if the consent information comprises the identifier of the requesting entity.

In the case of a consent information being based on the requested medical data record by comprising a hash of the medical data record, the method can furthermore comprise the step of determining a hash of the requested medical data record, the method can furthermore comprise the step of selecting consent information documented in the distributed consent ledger comprising the hash of the requested medical data record. In particular, the step of performing the first check can then be based on the consent information selected.

The inventors recognized that by performing the described first check it can be ensured that the requested medical data record is only provided to the requesting entity if the patient (the medical data record relates to) gave its consent to share the requested medical data record with the requesting entity.

According to a further possible embodiment of the invention, the consent information documented in the distributed consent ledger comprise a consent signature based on the respective medical data records and/or based on the respective identifier of the authorized entity, wherein the consent signature is signed based on a first identifier of the patient the respective medical data record is related to, and the method for using a uniform resource locator furthermore comprises the step of performing a second check whether the consent signature is validly signed based on the first identifier of the patient, wherein the step of providing is only executed in the case of a positive second check.

In particular, if the consent signature is signed with a private key of the second identifier of the patient, the second check can be based on the associated public key of the second identifier of the patient. In particular, the second check can comprise the execution of a signature validation algorithm, taking as input the consent signature and the associated public key of the second identifier of the patient.

The inventors recognized that by performing the described second check it can be ensured that the consent information actually was issued and/or acknowledged by the patient the medical data record relates to.

According to a further possible embodiment of the invention, the identifier of the requesting entity is based on a digital certificate. In particular, the identifier of the requesting entity is a digital certificate. In particular, the digital certificate is signed by a certificate authority. In particular, the step of performing a first check can be based on a comparison of the identifier of the requesting entity and the identifier of an authorized entity, both identifiers being digital certificates. In particular, the step of performing the check can comprise checking the validity of digital certificate being the identifier of the requesting entity.

The inventors recognized that by using a digital certificate as identifier of the requesting entity the security of the method can be improved, because the usage of a digital certificate allows proofing the identity of the requesting entity.

According to a further possible embodiment of the invention, the identifier of the requesting entity is a digital certificate, and the access request comprises a signature signed with the private key related to the digital certificate. The inventors recognized that by using this signature it can be proven that the requesting entity possesses the private key related to the digital certificate, which indicates that the requesting entity is the owner of the digital certificate, without exposing the private key to the server or to a third party. In particular, the sever can use the signature verification algorithm based on the public key of the digital certificate to proof the validity of the signature. In particular, the server and the user client can execute a challenge-respond method, in particular, the server can provide data the signature is to be created based on to the user client.

According to a further possible embodiment of the invention, the access request comprises an intended usage information, and the method furthermore comprises the step of determining a stored usage information based on the distributed consent ledger, wherein the stored usage information is documented in the distributed consent ledger related to the medical data record, and method furthermore comprises the step of performing a third check whether the intended usage information and the stored usage information match.

In general, the intended usage information and the stored usage information match, if the intended usage information specifies that the medical data record will be used according to the stored usage information. In particular, if both the intended usage information and the stored usage information comprise one or several items describing the intended or allowed use of the medical data record, the intended usage information and the stored usage information match if the items of the intended usage information are a subset of the items of the stored usage information.

The inventors recognized that by performing the third check related to the usage of the medical data record it can be ensured that the medical data record is only used according to the consent of the patient the medical data record is related to.

According to a further embodiment of the invention, ownership information are documented in a distributed ownership ledger, wherein each ownership information comprises a ownership signatures based on medical data records, wherein the ownership signature is signed based on a second identifier of a patient, and the method for using a uniform resource locator furthermore comprises the step of determining an ownership second identifier of the patient being owner of the requested medical data record based on the distributed ownership ledger with the computation unit, and the step of transferring cryptocurrency from a first account to a second account with the computation unit, wherein the second account is related to the ownership second identifier of the patient.

In particular, the distributed ownership ledger documents ownership information if the distributed ownership ledger comprises the ownership information. In particular, the distributed ownership ledger comprises the ownership information, if one of the data blocks of the distributed ownership ledgers comprises the ownership information. In particular, an ownership signature is based on a medical data record, if the ownership signature is the result of a signature algorithm applied to the medical data record and/or the hash of the medical data record. In particular, an ownership information comprising an ownership signature can furthermore comprise the medical data record and/or the hash of the medical data the ownership signature is based on. In particular, an ownership information comprising an ownership signature can furthermore comprise the second identifier the ownership information is signed based on or part of the second identifier the ownership information is signed based on.

In particular, the ownership second identifier is one of the second identifiers contained in the distributed ownership ledger, wherein a second identifier is contained in the distributed ownership ledger if there is an ownership information comprising a ownership signature signed based on the second identifier.

In particular, if consent information is documented in a distributed consent ledger, and if the distributed consent ledger documents consent information based on the requested medical data record, and if the documented consent information furthermore comprises a consent signature signed based on a first identifier of the patient, the second identifier and the first identifier are not identical. In particular, a private key contained in the first identifier is not equivalent with a private key contained in the second identifier, and a public key contained in the first identifier is not equivalent to a public key contained in the second identifier.

The inventors recognized that by the proposed additional steps a payment for a usage of the requested medical data record from the requesting entity to the patient can be induced. In particular, if there are differing second identities of the same patient for different medical data records related to the same patient, the transfers of cryptocurrency induced by the usage of different requested medical data records related to the same patient cannot be traced back to the same patient, making it difficult to use (possibly public) metadata to gather information about patients.

According to a further embodiment of the invention, the method for using a uniform resource locator furthermore comprises the step of receiving, by a trusted entity, an account information by the patient being owner of the requested medical data record, the step of transferring cryptocurrency from the second account to a third account based on the account information, wherein the third account is related to the trusted entity, and the step initiating a payment from the trusted entity to the patient by the trusted entity.

In particular, the account information is sent from a user client to the trusted entity, in particular to a payment server owned by the trusted entity, in particular from an interface of the user client to an interface of the payment server. In particular, the step of transferring cryptocurrency is executed by a computation unit of the payment server.

In particular, the account information is a private key related to the patient, in particular, the account information is a private key contained in a second identifier of a patient.

The payment initiated can comprise the transfer of a cryptocurrency, or the transfer of a standard currency.

The inventors recognized that by the proposed additional steps the patient can receive a payment for the usage of the medical data records related to the patient, while by the detour through the trusted entity the metadata of the single cryptocurrency transactions cannot be related to the patient.

In another embodiment, the invention relates to a providing system for providing a uniform resource locator, comprising:
 an interface, configured for receiving a medical data record, wherein the medical data record is related to a patient,
 furthermore configured for providing the uniform resource locator to the patient,
 a computation unit, configured for determining the uniform resource locator related to the medical data record, wherein the uniform resource locator comprises an authorization token based on the medical data record, and wherein the medical data record can be accessed by following the uniform resource locator.

In particular the providing system for providing a uniform resource locator can be configured to execute the method for providing a uniform resource locator according to the invention and its aspects and embodiments. The providing system is configured to execute the method and its aspects and embodiments by its interface and its computation unit being configured to execute the respective method steps.

The providing system can be realized as a data processing system or as a part of a data processing system. Such a data processing system can, for example, comprise a cloud-computing system, a computer network, a computer, a tablet computer, a smartphone or the like. The providing units can comprise hardware and/or software. The hardware can be, for example, a processor system, a memory system and combinations thereof. The hardware can be configurable by the software and/or be operable by the software.

The providing system can be realized as a server or as part of a server, alternatively, the providing system can be realized as a patient client or as part of a patient client, alternatively, the providing system can be realized as combination of a server and a patient client.

In another embodiment, the invention relates to a computer program product comprising a computer program, the computer program being loadable into a memory unit of a providing system, including program code sections to make the providing system execute the method for providing a uniform resource locator according to an embodiment of the invention when the computer program is executed in the providing system.

In a further possible embodiment, the invention relates to a computer-readable medium, on which program code sections of a computer program are saved, the program code sections being loadable into and/or executable in a providing system to make the providing system execute the method for providing a uniform resource locator according to an embodiment of the invention when the program code sections are executed in the accessing system.

The realization of embodiments of the invention by a computer program product and/or a computer-readable medium has the advantage that already existing providing systems can be easily adopted by software updates in order to work as proposed by embodiments of the invention.

In a further possible embodiment, the invention relates to usage system for using a uniform resource locator provided by a method for providing the uniform resource locator according to the invention or one of its embodiments, comprising:
 an interface, configured for receiving an access request directed to a requested medical data record, wherein the requested medical data record is stored within a repository, wherein the access request is based on the uniform resource locator,
 furthermore configured for providing the requested medical data record based on the access request,
 an computation unit.

In particular the usage system for using a uniform resource locator can be configured to execute the method for using a uniform resource locator according to the invention and its embodiments. The usage system is configured to execute the method and its embodiments by its interface and its computation unit being configured to execute the respective method steps.

The usage system can be realized as a data processing system or as a part of a data processing system. Such a data processing system can, for example, comprise a cloud-computing system, a computer network, a computer, a tablet computer, a smartphone or the like. The usage system can comprise hardware and/or software. The hardware can be, for example, a processor system, a memory system and combinations thereof. The hardware can be configurable by the software and/or be operable by the software.

The usage system can be realized as a server or as part of a server, alternatively, the usage system can be realized as a user client or as part of a user client, alternatively, the usage system can be realized as combination of a server and a user client.

In a further possible embodiment, the invention relates to a computer program product comprising a computer program, the computer program being loadable into a memory unit of an usage system, including program code sections to make the usage system execute the method for using a uniform resource locator according to an embodiment of the invention when the computer program is executed in the usage system.

In a further possible embodiment, the invention relates to a computer-readable medium, on which program code sections of a computer program are saved, the program code sections being loadable into and/or executable in an usage system to make the usage system execute the method for using a uniform resource locator according to an embodiment of the invention when the program code sections are executed in the usage system The realization of embodiments of the invention by a computer program product and/or a computer-readable medium has the advantage that already existing accessing systems can be easily adopted by software updates in order to work as proposed by embodiments of the invention.

According to a further possible embodiment, the invention relates to a method for providing a location information related to a medical data record. The method comprises receiving the medical data record with an interface, wherein the medical data record is related to a patient. Furthermore, the method comprises storing the medical data record within a repository with a computation unit. Furthermore, the method comprises determining the location information related to the medical data record stored within the repository with the computation unit, wherein the medical dataset can be accessed based on the location information. Furthermore, the method comprises providing the location information with the interface to the patient. In particular, the location information can be a uniform resource locator.

In particular, the interface is an interface of a providing system. In particular, the computation unit is a computation unit of the providing system. In particular, the memory unit is a memory unit of the providing system. In particular, the providing system can comprise a patient client and/or a server, wherein the interface can be the interface of the patient client and/or of the server, wherein the computation unit can be a computation unit of the patient client and/or of the server, and wherein the memory unit can be a memory unit of the patient client and/or of the server. In particular, the medical data record is stored within a repository within the memory unit. In particular, the repository is a part of the memory unit of the providing system or stored within the memory unit of the providing system, and in particular, the repository is a part of the memory unit of the server of the providing system or stored in the memory unit of the server of the providing system.

The inventors recognized that by this method medical data records relating to a patient can be accessed and used by the patient, including forwarding medical data records to a physician. In particular, a patient can decide based on forwarding only selected links which subset of the medical data records related to him a physician can access.

According to a further possible embodiment of the invention, the method for providing a location information furthermore comprises receiving an identifier of an authorized entity with the interface, wherein the authorized entity is allowed to access the medical data record stored within the memory unit, and wherein the location information is based on the identifier of the authorized entity.

The inventors have recognized that a location information based on the identifier of the authorized entity can be used to allow access to the medical data record using the location information only by the authorized entities. In particular, in the case the authorized entity forwards the location information to an unauthorized entity, the unauthorized entity is not able to access the medical data record based on the location information.

According to a further possible embodiment of the invention, the method for providing a location information furthermore comprises documenting the medical data record and the identifier of the authorized entity in a distributed ledger with the computation unit. In particular, the medical data record can be documented in the distributed ledger by documenting a hash of the medical data record in the distributed ledger. In particular, the identifier of the authorized entity can be documented in the distributed ledger by documenting a hash of the identifier of the authorized entity in the distributed ledger. In particular the medical data record and the identifier of the authorized entity can be documented in the distributed ledger by documenting a hash of a dataset in the distributed ledger, wherein the dataset is based on the medical data record and the identifier of the authorized entity. In particular, the dataset can be based on the medical data record by comprising the medical data record, and the dataset can be based on the identifier of the authorized entity by comprising the identifier of the authorized entity.

The inventors recognized that by documenting the medical data record and the identifier of the authorized entity in a distributed ledger, the process of a patient granting an authorized entity access to the medical data record can be documented in a revision-safety way, leading to a better data protection of the system.

According to a further possible embodiment of the invention, the step of documenting the medical data record and the identifier of the authorized entity in a distributed ledger comprises creating a signature based on the medical data record and/or on the identifier of the authorized entity, wherein the signature is signed with a private key related to the patient.

The inventors recognized that by creating a signature based on the medical data record and/or on the identifier of the authorized entity signed with the private key related to the patient it can be documented that the patient itself intents or intended to share the medical data record with the authorized entity.

According to a further possible embodiment of the invention, the method for providing a location information furthermore comprises sending the location information to the authorized entity with the interface.

In particular, the location information can provided to the authorized entity by creating an electronic message and sending the electronic message to the authorized entity. Examples for electronic messages are e-mail, short message service (an acronym is "SMS"), a message according to the Extensible Messaging and Presence Protocol (an acronym is "XMPP"), or other electronic messages. Alternatively, the location information can also be displayed on the patient device, e.g. as text information or as one-dimensional or two-dimensional code (such as a barcode, a QR-Code, a Matrix Code or an Aztec-Code). The displayed location information can then be entered into the user device manually or by taking a picture of the displayed code.

The inventors recognized that by providing the location information to the authorized entity the authorized entity is able to access the medical data record instantly without searching databases of medical data records or of location informations for the correct medical data record or the correct location information.

According to a further possible embodiment, the invention relates to a method for using a location information provided by a method for providing a location information, comprising receiving an access request to the medical data record by an interface, wherein the medical data record is stored within a memory unit, and wherein the access request is based on the location information. The method for using a location information furthermore comprises providing the medical data record with the interface.

In particular, the interface is an interface of a usage system. In particular, the usage system can furthermore comprise a computation unit. In particular, the memory unit is a memory unit of the usage system. In particular, the providing system can comprise a user client and/or a server, wherein the interface can be the interface of the user client and/or of the server, wherein the computation unit can be a computation unit of the user client and/or of the server, and wherein the memory unit can be a memory unit of the user client and/or of the server. In particular, the medical data record is stored within a repository within the memory unit. In particular, the repository is a part of the memory unit of the usage system or stored within the memory unit of the usage system, and in particular, the repository is a part of the memory unit of the server of the usage system or stored in the memory unit of the server of the usage system.

In particular, the medical data record can be encrypted before being provided. In particular, the medical data record can be encrypted using an asymmetric encryption using a public key of an entity receiving the medical data record.

The inventors recognized that by this method the medical data record can be provided in an efficient and direct manner, without searching the repository for the correct medical data record.

According to a further possible embodiment of the invention, the method for using a location information provided by a method for providing a location information comprises receiving an identifier of a requesting entity with the interface, wherein the access request is initiated by the requesting entity. The method furthermore comprises performing a check whether a pair comprising the medical data record and the identifier of the requesting entity are documented in the distributed ledger with the computation unit, wherein the step of providing is only executed in case of a positive check.

The inventors recognized that by performing the check and providing the medical data record only in the case of a positive check it can be ensured that the medical data record is only provided to an authorized entity, and not to an unauthorized entity.

According to a further possible embodiment the invention relates to a providing system for providing a location information related to a medical data record, comprising:
  an interface, configured for receiving the medical data record, wherein the medical data record is related to a patient,
  furthermore configured for providing the location information with the interface to the patient,
  a computation unit, configured for storing the medical data record within a memory unit, furthermore configured for determining the location information related to the medical data record stored within the memory unit, wherein the medical dataset can be accessed based on the location information.

According to a further possible embodiment, the invention relates to a computer program product comprising program elements which induce a providing system to carry out the steps of the method for providing a location information according an embodiment of the invention, when the program elements are loaded into a memory unit of the providing system.

According to a further possible embodiment, the invention relates to a computer-readable medium, on which program code sections of a computer program are saved, the program code sections being loadable into and/or executable in a providing system to make the providing system execute the method for providing a location information according to an embodiment of the invention, when the program code sections are executed in the providing system.

According to a further possible embodiment, the invention relates to a usage system, configured for receiving an access request to a medical data record, wherein the medical data record is stored within the usage system, in particular within a memory unit of the usage system, wherein the access request is based on a location information provided by a method for providing a location information according to the invention, furthermore configured for providing the medical data.

According to a further possible embodiment, the invention relates to a computer program product comprising program elements which induce a usage system to carry out the steps of the method for using a location information according to an embodiment of the invention, when the program elements are loaded into a memory unit of the usage system.

According to a further possible embodiment, the invention relates to a computer-readable medium, on which program code sections of a computer program are saved, the program code sections being loadable into and/or executable in a usage system to make the usage system execute the method for using a location information according to an embodiment of the invention, when the program code sections are executed in the usage system.

According to a further possible embodiment, the invention relates to a method for storing consent, comprising receiving a medical data record with an interface, wherein the medical data record is related to a patient. The method furthermore comprises receiving an identifier of an authorized entity with the interface. The method furthermore comprises determining consent information with a computation unit, wherein the consent information is based on the medical data record and the identifier of the authorized entity. The method furthermore comprises documenting the consent information in a distributed consent ledger with the computation unit.

In particular, the interface is an interface of a providing system. In particular, the computation unit is a computation unit of the providing system. In particular, the providing system can comprise a memory unit. In particular, the providing system can comprise a patient client and/or a server, wherein the interface can be the interface of the patient client and/or of the server, wherein the computation unit can be a computation unit of the patient client and/or of the server, and wherein the memory unit can be a memory unit of the patient client and/or of the server. In particular, the medical data record is stored within a repository within the memory unit. In particular, the repository is a part of the memory unit of the providing system or stored within the memory unit of the providing system, and in particular, the repository is a part of the memory unit of the server of the providing system or stored in the memory unit of the server of the providing system.

In particular, the consent information is based on the medical data record by comprising a hash of the medical data record. In particular, the consent information is based on the identifier of the authorized entity by comprising the identifier of the authorized entity or a hash of the identifier of the authorized entity. In particular, the consent information is based on the medical data record and on the identifier of the authorized entity by comprising a hash of a combination of the medical data record and the identifier of the authorized entity. In particular, the identifier of the authorized entity may be based on a private key and/or a public key associated with the authorized entity. In particular, the identifier of the authorized entity may comprise a public key associated with the authorized entity.

The inventors recognized that by storing consent information in a distributed consent ledger the consent information can be stored in a revision-safety and non-disputable way.

According to a further possible embodiment of the invention, the method for storing consent information comprises receiving a first identifier of the patient with the interface, wherein the consent information is furthermore based on the first identifier of the patient. In particular, the first identifier of the patient can be based on a private key and/or a public key related to the patient.

The inventors recognized, that by the consent information being based on the first identifier of the patient it can be stored in a revision-safety and non-disputable way that it was actually the patient issuing the consent information or giving its consent to using the data.

According to a further possible embodiment of the method for storing consent information, the consent information comprises a consent signature based on the medical data record and based on the identifier of the authorized entity, wherein the consent signature is signed with the first identifier of the patient.

The inventors recognized that by the consent information comprising a consent signature the fact that a patient actually consented to the use of the medical data record can be checked easily be performing a check of the consent signature based on the private key of the respective patient.

According to a further possible embodiment of the invention, the method for storing consent information comprises receiving a second identifier of the patient with the interface. Furthermore, the method comprises determining ownership information with the computation unit, wherein the ownership information comprises an ownership signature based on the medical data record, wherein the ownership signature is signed with the second identifier of the patient. Furthermore, the method comprises documenting the ownership information in a distributed ownership ledger.

In particular, the second identifier of the patient can be identical with the first identifier of the patient; alternatively, the first identifier of the patient and the second identifier of the patient can be different. In particular, the distributed ownership ledger can be identical with the distributed consent ledger; alternatively, the distributed ownership ledger and the distributed consent ledger can be different.

The inventors recognized that by the ownership signature being signed with the second identifier of the patient, whereas the consent signature is signed with the first identifier of the patient, the ownership of the medical data record can be documented separately from the consent to use the medical data record, so that the anonymization of the system can be improved, and it is more difficult to gather information about patients using metadata.

According to a further possible embodiment of the invention, the method for storing consent information comprises receiving usage information with the interface, wherein the consent information is furthermore based on the usage information.

The inventors recognized that by including usage information into the consent information the usages the patient consented to can be stored in a revision-safety way. In particular, using the medical data in a non-consented way can be documented and/or prevented.

According to a further possible embodiment of the invention, within the method for storing consent information the consent information comprises a smart contract.

The inventors recognized that by a smart contract being contained in the consent information it can be ensured that the medical data record is only used in a way the patient consented to.

According to a further possible embodiment of the invention, within the method for storing consent information the smart contracts regulates a transfer of cryptocurrency in the event of using the medical data record, wherein the cryptocurrency is transfer from a first account to a second account, wherein the first account is related to an entity using the medical data record, and wherein the second account is related to the first identifier of the patient and/or to the second identifier of the patient.

The inventors recognized that by transferring cryptocurrency an efficient payment process for usage of the medical data record can be initiated, while not disclosing the identity of the patients related to the medical data record.

According to a further possible embodiment, the invention relates to a method for using consent information stored in a distributed consent ledger according to the method for storing consent information and its embodiments, comprising receiving an access request directed to a requested medical data record by an interface, wherein the requested medical data record is stored within a memory unit, and wherein the requested medical data record is related to a patient, furthermore comprising locating consent information in the distributed consent ledger with a computation unit, wherein the consent information is related to the requested medical data record, performing a check based on the consent information whether the patient consented to a use of the requested medical data record with the computation unit, furthermore comprising, in case of a positive first check, processing the requested medical data record with the computation unit.

In particular, the interface is an interface of a usage system. In particular, the computation unit is a computation unit of the usage system. In particular, the memory unit is a memory unit of the usage system. In particular, the providing system can comprise a user client and/or a server, wherein the interface can be the interface of the user client and/or of the server, wherein the computation unit can be a computation unit of the user client and/or of the server, and wherein the memory unit can be a memory unit of the user client and/or of the server. In particular, the medical data record is stored within a repository within the memory unit. In particular, the repository is a part of the memory unit of the usage system or stored within the memory unit of the usage system, and in particular, the repository is a part of the memory unit of the server of the usage system or stored in the memory unit of the server of the usage system.

In particular, the consent information is related to the requested medical data record if the consent information comprises the requested medical data record, and/or if the consent information comprises a hash of the requested medical data record, and/or if the consent information comprises a link to the requested medical data record, in particular an uniform resource locator directing to the medical data record.

In particular, whether the patient consented to a use of the requested medical data record can be determined by whether a consent information based on the requested medical data record is contained in the distributed consent ledger. Alternatively, whether the patient consented to a use of the requested medical data record can be encoded within the consent information.

In particular, the interface is an interface of the server and/or the repository. In particular, the computation unit is an computation unit of the server.

The inventors recognized that by this method for using consent information. the processing of medical data records can be tied to the consent given by the patient being subject of the medical data record.

According to a further possible embodiment of the invention, within the method for using consent information stored in a distributed consent ledger, the access request is initiated by a requesting entity, and the method furthermore comprises receiving an identifier of the requesting entity with the interface. Furthermore, the consent information comprises an identifier of an authorized entity, and the check is furthermore based on a comparison of the identifier of the requesting entity and the identifier of the authorized entity. In particular, the check is positive if the identifier of the requesting entity and the identifier of the authorized entity are equivalent. In particular, the check can also be positive if the identifier of the requesting entity is derived from the identifier of the authorized entity. In particular, the consent information comprises a plurality of identifiers of authorized entities.

The inventors recognized that by comparing identifiers of authorized entities with the identifier of the requesting entity it can be ensured that the requested medical data record is only processed by or for an entity the patient gave its consent to be able to do so.

According to a further possible embodiment of the invention, within the method for using consent information stored in a distributed consent ledger, the consent information comprises a smart contract. Furthermore, processing the requested medical data record comprises executing the smart contract.

The inventors recognized that by executing smart contracts contained in the consent information during if processing the requested medical data record, consequences of processing the requested medical data record can occur as an immediate result of the processing. Examples for such consequences could sending a message informing about the processing of the requested medical data record, or payments related to the processing of the requested medical data record.

According to a further possible embodiment of the invention, within the method for using consent information stored in a distributed consent ledger, the access request comprises a trainable function, wherein processing the requested medical data record comprises training the trainable function based on the requested medical data record, and optionally providing the trainable function after training the trainable function based on the requested medical data record.

In general, a trainable function is a function mapping input data to output data, wherein the output data is furthermore dependent on at least one parameter of the trainable function. In particular, training the trainable function comprises adapting the at least one parameter based on training data. In particular, the parameter of the trainable function can be adapted by applying the trainable function to input data to calculated output data, and by comparing the output data by known output data corresponding to the input data (supervised learning). Also other forms of adapting the parameters are known, for example semi-supervised learning or unsupervised learning. Examples for trainable functions are artificial neural networks (in particular convolutional artificial neural networks, in particular deep convolutional artificial neural networks) and support vector machines.

The inventors have recognized that by training a trainable function on the server and/or on the repository based on the requested medical data record, the requested medical data record does not need to be transmitted to outside of the server and/or the repository. In particular, the requested medical entity cannot be sent from the requesting entity to an unauthorized entity, neither on accident nor on purpose. Furthermore, the number of training steps performed based on the requested medical data record can be controlled; in particular, each training step can be billed separately.

According to a further possible embodiment of the invention, within the method for using consent information stored in a distributed consent ledger, processing the requested medical data record comprises displaying the requested medical data record in a non-copyable way.

In particular, the requested medical data record can be displayed in a web-interface, wherein by using server side code or client side code (like JavaScript) making a copy of the requested medical data record can be hampered or even made impossible. Furthermore, an on-premises viewer software can be used on a user client which does not allow to copy a displayed requested medical data record, and processing can comprises sending the requested medical data record to the on-premises software viewer.

The inventors recognized that by displaying the requested medical data record in a non-copyable way a user can use the requested medical data record as a reference value or a reference case, without being able to store the requested medical data record or to distributed the requested medical data record to an unauthorized entity. In particular, each use of the requested medical data record as a reference value or a reference case can be billed separately.

According to a further possible embodiment of the invention, within the method for using consent information stored in a distributed consent ledger, ownership information are documented in a distributed ownership ledger, wherein each ownership information comprises an ownership signatures based on medical data records, wherein the ownership signature is signed based on a second identifier of a patient, the method furthermore comprising determining an second identifier of the patient being owner of the requested medical data record based on the distributed ownership ledger with the computation unit, and the method furthermore comprising transferring cryptocurrency from a first account to a second account, wherein the first account is related to the identifier of the requesting entity, and wherein the second account is related to the second identifier of the patient.

The inventors recognized that by the proposed additional steps a payment for a usage of the requested medical data record from the requesting entity to the patient can be induced. In particular, if there are differing second identities of the same patient for different medical data records related to the same patient, the transfers of cryptocurrency induced by the usage of different requested medical data records related to the same patient cannot be traced back to the same patient, making it difficult to use (possibly public) metadata to gather information about patients.

According to a further possible embodiment of the invention, the method for using consent information stored in a distributed consent ledger comprises receiving, by a trusted entity, an account information by the patient being owner of the medical data record, transferring cryptocurrency from the second account to a third account based on the account information, wherein the third account is related to the trusted entity, and initiating a payment from the trusted entity to the patient.

The inventors recognized that by the proposed additional steps the patient can receive a payment for the usage of the medical data records related to the patient, while by the detour through the trusted entity the metadata of the single cryptocurrency transactions cannot be related to the patient.

According to a further possible embodiment, the invention relates to a consent storage system for storing consent, comprising:
   an interface, configured for receiving a medical data record with an interface, wherein the medical data record is related to a patient,
   furthermore configured for receiving an identifier of an authorized entity with the interface,
   a computation unit, configured for determining consent information with a computation unit, wherein the consent information is based on the medical data record and the identifier of the authorized entity, furthermore configured for documenting the consent information in a distributed consent ledger with the computation unit.

In particular, the consent storage system for storing consent can be configured to execute the method for storing consent according to the invention and its embodiments. The consent storage system is configured to execute the method and its embodiments by its interface and its computation unit being configured to execute the respective method steps.

The consent storage system can be realized as a data processing system or as a part of a data processing system. Such a data processing system can, for example, comprise a cloud-computing system, a computer network, a computer, a tablet computer, a smartphone or the like. The consent storage system can comprise hardware and/or software. The hardware can be, for example, a processor system, a memory system and combinations thereof. The hardware can be configurable by the software and/or be operable by the software.

The consent storage system can be realized as a server or as part of a server, alternatively, the consent storage system can be realized as a patient client or as part of a patient client, alternatively, the consent storage system can be realized as combination of a server and a patient client. In particular, the consent storage system can be identical with a providing system.

According to a further possible embodiment, the invention relates to a computer program product comprising program elements which induce a consent storage system to carry out the steps of the method for method for storing consent an embodiment of the invention, when the program elements are loaded into a memory unit of the consent storage system.

According to a further possible embodiment, the invention relates to a computer-readable medium, on which program code sections of a computer program are saved, the program code sections being loadable into and/or executable in a consent storage system to make the consent storage system execute the method for storing consent according to an embodiment of the invention, when the program code sections are executed in the consent storage system.

The realization of the invention by a computer program product and/or a computer-readable medium has the advantage that already existing providing systems can be easily adopted by software updates in order to work as proposed by the invention.

According to a further possible embodiment, the invention relates to a consent usage system for using consent information stored in a distributed consent ledger according to the method according for storing consent, comprising:
   an interface, configured for receiving an access request directed to a requested medical data record by an interface, wherein the requested medical data record is stored within a repository, and wherein the requested medical data record is related to a patient,
   a computation unit, configured for locating consent information in the distributed consent ledger with a computation unit, wherein the consent information is related to the requested medical data record,
   Furthermore configured for performing a check (CHK) based on the consent information whether the patient consented to use the requested medical data record with the computation unit,
   furthermore configured, in case of a positive first check, for processing the requested medical data record with the computation unit.

In particular, the consent usage system for using consent information stored in a distributed consent ledger can be configured to execute the method for using consent information stored in a distributed consent ledger according to the invention and its embodiments. The consent usage system is configured to execute the method and its embodiments by its interface and its computation unit being configured to execute the respective method steps.

The consent usage system can be realized as a data processing system or as a part of a data processing system. Such a data processing system can, for example, comprise a cloud-computing system, a computer network, a computer, a tablet computer, a smartphone or the like. The consent usage system can comprise hardware and/or software. The hardware can be, for example, a processor system, a memory system and combinations thereof. The hardware can be configurable by the software and/or be operable by the software.

The consent usage system can be realized as a server or as part of a server, alternatively, the consent usage system can be realized as a user client or as part of a user client, alternatively, the consent usage system can be realized as combination of a server and a user client. In particular, the consent usage system can be identical with a usage system.

According to a further possible embodiment, the invention relates to a computer program product comprising program elements which induce a consent usage system to carry out the steps of the method for using consent information stored in a distributed consent ledger according to an embodiment of the invention, when the program elements are loaded into a memory unit of the consent usage system.

According to a further possible embodiment, the invention relates to a computer-readable medium, on which program code sections of a computer program are saved, the program code sections being loadable into and/or executable in a consent usage system to make the consent usage system execute the method for using consent information stored in a distributed consent ledger according to an embodiment of the invention, when the program code sections are executed in the usage system.

The realization of the invention by a computer program product and/or a computer-readable medium has the advantage that already existing providing systems can be easily adopted by software updates in order to work as proposed by embodiments of the invention.

FIG. 1 displays a flowchart of the first embodiment of the method for providing PROV-URL a uniform resource locator URL. The first step of the displayed embodiment is receiving REC-MDR a medical data record MDR, MDR.j, MDR.k, MDR.l with an interface PS.IF, wherein the medical data record MDR, MDR.j, MDR.k, MDR.l is related to a patient PAT. In particular, the interface PS.IF is an interface PS.IF of a providing system PS. In this embodiment, the providing system PS comprises a server S being a webserver connected with the internet.

In this embodiment, the medical data record MDR, MDR.j, MDR.k, MDR.l comprises a medical imaging dataset. Alternatively, the medical data record MDR, MDR.j, MDR.k, MDR.l can also comprise other medical data, for example personal health information, laboratory reports, an electronic medical record, diagnosis information or other medical data.

The second step of the displayed embodiment is storing STR-MDR the medical data record MDR, MDR.j, MDR.k, MDR.l with a memory unit PS.MU of the providing system PS. In particular, the memory unit PS.MU of the providing system PS comprises a repository located within the server S, wherein the medical data record MDR, MDR.j, MDR.k, MDR.l is stored within the repository of the server S. In this embodiment, the medical data record MDR, MDR.j, MDR.k, MDR.l is stored as a file within a folder of a folder structure of the repository. In particular, a filename and is assigned to the medical data record MDR, MDR.j, MDR.k, MDR.l.

The second step of storing STR.MDR the medical data record MDR, MDR.j, MDR.k, MDR.l with the memory unit PS.MU is optional. Alternatively, the medical data record MDR, MDR.j, MDR.k, MDR.l can be stored with the memory unit before executing the method for providing PROV-URL a uniform resource locator URL. In this case, the step of receiving REC-MDR the medical data record MDR, MDR.j, MDR.k, MDR.l with the interface PS.IF can comprise receiving the filename and/or the location of the medical data record MDR, MDR.j, MDR.k, MDR.l already stored in the repository.

In this embodiment, the medical data record MDR, MDR.j, MDR.k, MDR.l is stored for example in the folder "data/ct/" and has the filename "mdr_1.dat". The server S being a webserver is accessible by the uniform resource locator "cloud-storage.com"

The third step of the displayed embodiment is determining DET-URL the uniform resource locator URL related to the medical data record MDR, MDR.j, MDR.k, MDR.l with a computation unit PS.CU, wherein the uniform resource locator URL comprises an authorization token based on the medical data record MDR, MDR.j, MDR.k, MDR.l, wherein the uniform resource locator URL comprises the location of the medical data record MDR, MDR.j, MDR.k, MDR.l in the repository and wherein the medical data record MDR, MDR.j, MDR.k, MDR.l can be accessed by following the uniform resource locator URL. In particular, the computation unit PS.CU is a computation unit PS.CU of the providing system PS; in particular, the computation unit PS.CU is a computation unit S.CU of the server.

In this embodiment, the uniform resource locator URL is "http://cloud-storage.com/data/ct/mdr_1.dat?auth=7597655124", wherein "cloud-storage.com/data/ct/mdr_1.dat" is the location of the medical data record MDR, MDR.j, MDR.k, MDR.l, and "7597655124" is the authorization token. Instead of the "http" (acronym for "Hypertext Transfer Protocol") scheme other schemes can be used, e.g. the "https" (acronym for "Hypertext Transfer Protocol Secure") scheme or the "ftp" (acronym for "File Transfer Protocol") can be used.

Alternatively, the uniform resource locator URL can be "http://cloud-storage.com? mdr=3694721586&auth=7597655124", wherein the "3694721586" is the location of the medical data record MDR, MDR.j, MDR.k, MDR.l, and "7597655124" is the authorization token. In this case, the location of the medical data record MDR, MDR.j, MDR.k, MDR.l is not equivalent with the location of the medical data record MDR, MDR.j, MDR.k, MDR.l in the file system of the memory unit PS.MU or the repository, but a string (in particular, a hash), which has to be mapped to the location of the medical data record MDR, MDR.j, MDR.k, MDR.l in the file system of the memory unit PS.MU or the repository by the memory unit PS.MU or the repository if the medical data record MDR, MDR.j, MDR.k, MDR.l should be accessed. This mapping can be done via a list storing associations between strings or hashes and the corresponding locations in the file system.

In this embodiment, the authorization token is based on the medical data record MDR, MDR.j, MDR.k, MDR.l by being specific for the medical data record MDR, MDR.j, MDR.k, MDR.l, meaning that this authorization token can only be used for accessing exactly one medical data record MDR, MDR.j, MDR.k, MDR.l, and no other medical data record MDR, MDR.j, MDR.k, MDR.l. For example, the authorization token can be identical with a hash H(MDR), H1/2(MDR.j), H1/2(MDR.k), H1/2(MDR.l) of the medical data record MDR, MDR.j, MDR.k, MDR.l. Alternatively, the correspondence between medical data records MDR, MDR.j, MDR.k, MDR.l (or locations of medical data records MDR, MDR.j, MDR.k, MDR.l) and authorization tokens can be stored in a database or in a list within the memory unit PS.MU or the repository. In the latter case, the step of storing STR-MDR the medical data record MDR, MDR.j, MDR.k, MDR.l or the step of determining DET-URL the uniform resource locator URL comprises determining an authorization token and storing the authorization token in the list.

Alternatively, the authorization token can also be identical with the filename or the filename and the path of the medical data record MDR, MDR.j, MDR.k, MDR.l in the repository. In the example case the authorization token would be "mdr_1.dat" or "data/ct/mdr_1.dat". In other words, there is no list of the medical data records MDR, MDR.j, MDR.k, MDR.l stored in the memory unit PS.MU and/or the repository, and in order to access a certain medical data record MDR, MDR.j, MDR.k, MDR.l, its filename and/or its path and its filename must be known.

Alternatively, the uniform resource locator URL can be a HTTP GET request or a HTTP POST request. For example, the uniform resource locator URL can be the following HTTP GET request:
 GET/get_data.php?mdr=3694721586&auth=
  7597655124 HTTP/1.1
 Host: cloud-storage.com
Here, "3694721586" is the location of the medical data record MDR, MDR.j, MDR.k, MDR.l, and "7597655124" is the authorization token. The same location of the medical data record MDR, MDR.j, MDR.k, MDR.l and the same authorization token are contained in the following HTTP POST request:

POST/get_data.php HTTP/1.1
Host: cloud-storage.com
Content-Type: application/x-www-form-urlencoded
Content-Length: 30
mdr=3694721586&auth=7597655124

The fourth step of the displayed embodiment is providing PROV-URL the uniform resource locator URL with the interface PS.IF to the patient PAT. In particular, the uniform resource locator URL is sent from the interface S.IF of a server to a patient client PC, in particular to an interface PC.IF of the patient client PC.

In this embodiment, the server S is a webserver, and the patient client PC is a mobile device of the patient PAT, in particular a smartphone. The smartphone hosts a app which can be used for handling different uniform resource locators URL to different medical data records MDR, MDR.j, MDR.k, MDR.l of the patient PAT. The server S uses a push message to include the additional uniform resource locators URL into the app, alternatively the server S can send a message containing the uniform resource locators URL to the smartphone, for example an SMS (acronym for "Short Message Service"), an MMS (acronym for "Multimedia Messaging Service") or an e-mail. It is also possible to use methods for providing the uniform resource locator URL, for example by displaying the uniform resource locator URL as one-dimensional or two-dimensional code (e.g. barcode, QR-Code, Matrix-Code, Aztec-Code) on a display device of the server S, so that the uniform resource locator URL can be retrieved by capturing an image of the one-dimensional or two-dimensional code, and by decoding the one-dimensional or two-dimensional code contained in the image.

Figure 2:
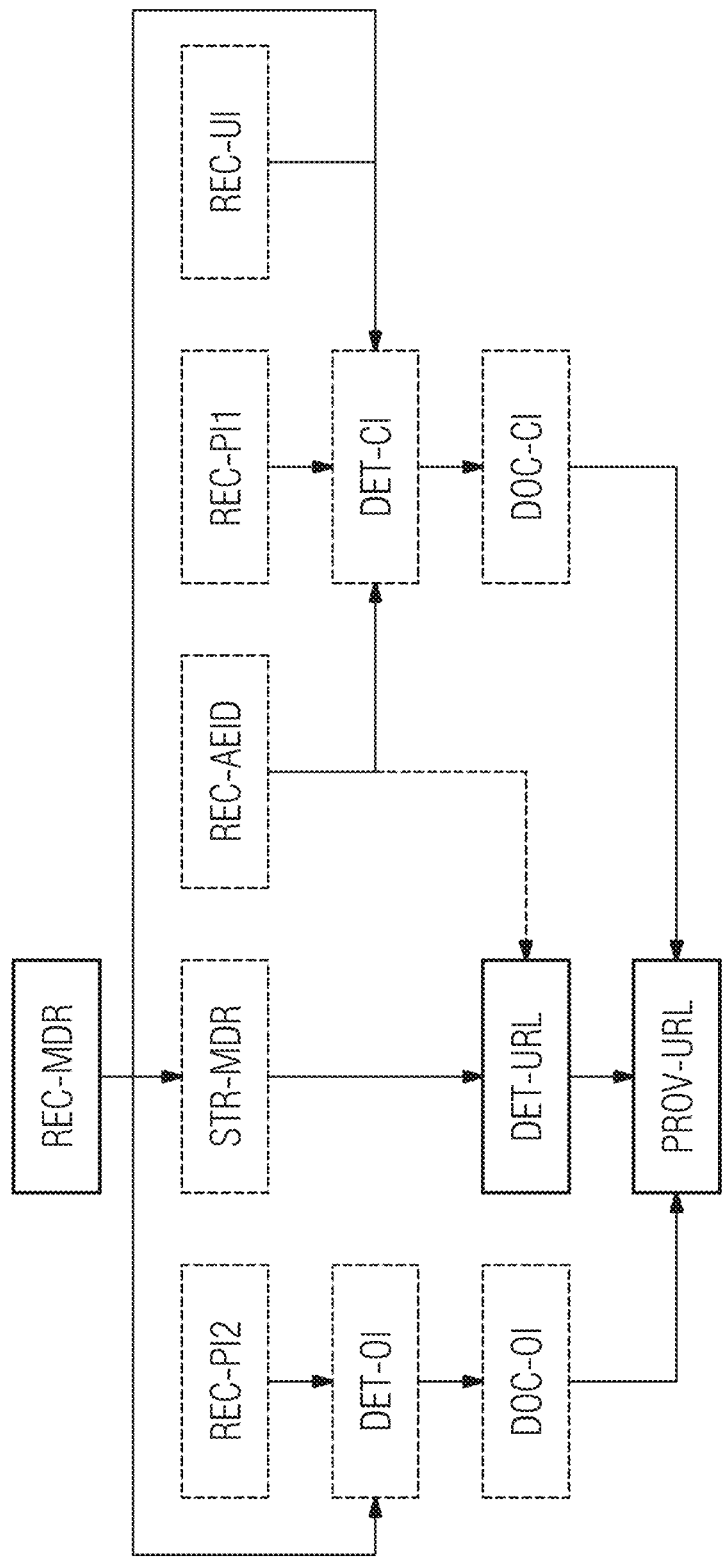

FIG. 2 displays a flowchart of the second embodiment of the method for providing PROV-URL a uniform resource locator URL. Optional steps are marked with dashed lines.

The second embodiment of the method for providing PROV-URL a uniform resource locator URL comprises all steps of the first embodiment of the method for providing PROV-URL a uniform resource locator URL. In particular, the steps of receiving REC-MDR a medical data record MDR, MDR.j, MDR.k, MDR.l, of storing STR.MDR the medical data record MDR, MDR.j, MDR.k, MDR.l, of determining DET-URL the uniform resource locator URL and of providing PROV-URL the uniform resource locator URL can comprise all features and alternative embodiments described with respect to the first embodiment and/or FIG. 1.

The second embodiment comprises the step of receiving REC-AEID an identifier AEID, AEID.j, AEID.k, AEID.l of an authorized entity AE by the interface PS.IF, wherein the authorized entity AE is allowed to access the medical data record MDR, MDR.j, MDR.k, MDR.l, wherein the uniform resource locator URL is based on the identifier AEID, AEID.j, AEID.k, AEID.l of the authorized entity AE. In particular, the identifier AEID, AEID.j, AEID.k, AEID.l of the authorized entity AE can be sent by the patient client PC to the server S, in particular to an interface of the server S.

In this embodiment, the identifier AEID, AEID.j, AEID.k, AEID.l of an authorized entity AE is a string variable which identifies the authorized entities AE. The string variable can be stored related to the medical data record MDR, MDR.j, MDR.k, MDR.l in a database of memory unit PS.MU, in particular within the repository. In particular, the memory unit PS.MU can store a list of medical data records MDR, MDR.j, MDR.k, MDR.l stored in the memory unit PS.MU and/or the repository, and for each medical data record MDR, MDR.j, MDR.k, MDR.l one or several string variables for one or more authorized entities AE.

For example, a first authorized entity AE can have the identifier "57458415", and a second authorized entity AE can have the identifier "71497388". The uniform resource locator URL for the first authorized entity AE can then be "http://cloud-storage.com/data/ct/mdr_1.dat?auth=7597655124& eid=57458415", and the uniform resource locator URL for the second authorized entity AE can be "http://cloud-storage.com/data/ct/mdr_1.dat?auth=7597655124& eid=71497388". By including the identifier AEID, AEID.j, AEID.k, AEID.l of the authorized entity AE into the uniform resource locator URL, it can be determined which authorized entity AE accesses the medical data record.

In this embodiment, the same identifier AEID, AEID.j, AEID.k, AEID.l of an authorized entity AE can be used for different medical data records MDR, MDR.j, MDR.k, MDR.l. Alternatively, it is also possible to use different identifiers AEID, AEID.j, AEID.k, AEID.l of the authorized entity AE for different medical data records MDR, MDR.j, MDR.k, MDR.l. In particular, it is not essential for the invention that the uniform resource locator URL comprises the identifier AEID, AEID.j, AEID.k, AEID.l of the authorized entity AE, or that the uniform resource locator URL is based on the identifier AEID, AEID.j, AEID.k, AEID.l of the authorized entity AE.

Alternatively, the identifier AEID, AEID.j, AEID.k, AEID.l of the authorized entity AE can also be based on a digital certificate. In particular, the digital certificate can be signed by a certificate authority. In particular, the identifier AEID, AEID.j, AEID.k, AEID.l of the authorized entity AE can comprise the digital certificate.

The second embodiment furthermore comprises the step of determining DET-CI consent information CI, CI.j, CI.k, CI.l, wherein the consent information CI, CI.j, CI.k, CI.l is related to the consent of the patient PAT to the use of the medical data record MDR, MDR.j, MDR.k, MDR.l by the authorized entity AE, and wherein the consent information CI, CI.j, CI.k, CI.l is based on the medical data record MDR, MDR.j, MDR.k, MDR.l and/or on the identifier AEID, AEID.j, AEID.k, AEID.l of the authorized entity AE. The second embodiment furthermore comprises the step of receiving REC-PI1 a first identifier PID1 of the patient PAT with the interface PS.IF, wherein the consent information CI, CI.j, CI.k, CI.l is furthermore based on the first identifier PID1 of the patient PAT. The second embodiment furthermore comprises the step of receiving REC-UI usage information UI, UI.j, UI.k, UI.l with the interface PS.IF, wherein the consent information CI, CI.j, CI.k, CI.l is furthermore based on the usage information UI, UI.j, UI.k, UI.l.

In this embodiment, the consent information CI, CI.j, CI.k, CI.l comprises a signature SGN(H(MDR) & AEID, PRK) of a hash H(MDR), H1(MDR.j), H1(MDR.k), H1(MDR.l) of the medical data record MDR, MDR.j, MDR.k, MDR.l and the identifier AEID, AEID.j, AEID.k, AEID.l of the authorized entity AE, signed with a first identifier PID1 being a first private key PAT.PRK1, PAT.j.PRK1, PAT.k.PRK1, PAT.l.PRK1 of the patient PAT, the signature being denoted as consent signature CSGN, CSGN.j, CSGN.k, CSGN.l. In this case, the consent information CI, CI.j, CI.k, CI.l is based on both the medical data record MDR, MDR.j, MDR.k, MDR.l and the identifier AEID, AEID.j, AEID.k, AEID.l of the authorized entity AE. The operator "&" means a concatenation of the hash H(MDR), H1(MDR.j), H1(MDR.k), H1(MDR.l) of the medical data record MDR, MDR.j, MDR.k, MDR.l and the identifier AEID, AEID.j, AEID.k, AEID.l of the authorized entity AE, e.g. if both are given as strings, the operator "&" can be interpreted as concatenation of strings, alternatively, of both are given as numbers, the operator "&" can be interpreted as adding the numbers. Alternatively, the consent information CI, CI.j, CI.k, CI.l can also comprise separate signatures for the hash H(MDR), H1(MDR.j), H1(MDR.k), H1(MDR.l) of the medical data record MDR, MDR.j, MDR.k, MDR.l and the identifier AEID, AEID.j, AEID.k, AEID.l of the authorized entity AE. Alternatively, the consent information CI, CI.j, CI.k, CI.l can comprise a (consent) signature SGN(H(MDR), PRK) based only on the medical data record MDR, MDR.j, MDR.k, MDR.l, e.g. being a signature of a hash H(MDR), H1(MDR.j), H1(MDR.k), H1(MDR.l) of the medical data record MDR, MDR.j, MDR.k, MDR.l signed with the first private key PAT.PRK1, PAT.j.PRK1, PAT.k.PRK1, PAT.l.PRK1 of the patient PAT. This case can be interpreted that the patient PAT gives consent that every entity can use the medical data record MDR, MDR.j, MDR.k, MDR.l. Alternatively, the consent information CI, CI.j, CI.k, CI.l can comprise a (consent) signature SGN(AEID, PRK) based only on the identifier AEID, AEID.j, AEID.k, AEID.l of the authorized entity AE. This case can be interpreted that the patient PAT gives consent that the authorized entity AE accesses every medical data record MDR, MDR.j, MDR.k, MDR.l related to the patient PAT.

In this embodiment, the first identifier PID1 of the patient PAT is the first public key PAT.PBK1, PAT.j.PBK1, PAT.k.PBK1, PAT.l.PBK1 related to the first private key PAT.PRK1, PAT.j.PRK1, PAT.k.PRK1, PAT.l.PRK1 used for signing the medical data record MDR, MDR.j, MDR.k, MDR.l and/or on the identifier AEID, AEID.j, AEID.k, AEID.l of the authorized entity AE. The consent information CI, CI.j, CI.k, CI.l then comprises the consent signature CSGN, CSGN.j, CSGN.k, CSGN.l and the first public key PAT.PBK1, PAT.j.PBK1, PAT.k.PBK1, PAT.l.PBK1. Alternatively, the first identifier PID1 of the patient PAT received REC-PI1 is the first private key PAT.PRK1, PAT.j.PRK1, PAT.k.PRK1, PAT.l.PRK1 of the patient PAT. Alternatively, the consent information CI, CI.j, CI.k, CI.l can also be determined on the patient client PC, in this case, the first identifier PID1 of the patient PAT can be identified with the consent information CI, CI.j, CI.k, CI.l itself.

In this embodiment, the usage information UI, UI.j, UI.k, UI.l comprises both a usage type and a usage compensation. The usage type can take the exemplary values or tags "diagnostic", "reference" or "training", or any combination of these tags. If the tag "diagnostic" is set, then the patient PAT gives its consent that the medical data record MDR, MDR.j, MDR.k, MDR.l is used for diagnostic purposes. If the tag "reference" is used, the patient PAT gives its consent that the medical data record MDR, MDR.j, MDR.k, MDR.l may be used as a reference case for physicians. If the tag "training" is used, the patient PAT gives its consent that the medical data record MDR, MDR.j, MDR.k, MDR.l is used for training in machine learning algorithms. The usage compensation can specify an amount of cryptocurrency CC.j, CC.k, CC.l that will be transferred to the patient PAT in the case the medical data record MDR, MDR.j, MDR.k, MDR.l is used. In particular, there can be a different usage compensation for the different usage types.

In this embodiment, the usage information UI, UI.j, UI.k, UI.l can be a smart contract, wherein the smart contracts regulates a transfer of cryptocurrency in the event of a usage of the medical data record MDR, MDR.j, MDR.k, MDR.l, wherein the cryptocurrency is transfer from a first account to a second account, wherein the first account is related to an entity using the medical data record MDR, MDR.j, MDR.k, MDR.l, and wherein the second account is related to the first identifier PID1 of the patient PAT and/or to the second identifier PID2 of the patient PAT.

The second embodiment furthermore comprises the step of documenting DOC-CI the consent information CI, CI.j, CI.k, CI.l in a distributed consent ledger CLDG by the computation unit PS.CU. In this embodiment, the step of documenting DOC-CI the consent information CI, CI.j, CI.k, CI.l is executed by inserting a further data block CDB.i, . . . , CDB.l into the distributed consent ledger CLDG, wherein the further data block CDB.i, . . . , CDB.l comprises the consent information CI, CI.j, CI.k, CI.l. It is possible that the further data block CDB.i, . . . , CDB.l does comprise several consent informations CI, CI.j, CI.k, CI.l, or other data beside the consent information CI, CI.j, CI.k, CI.l. The computation unit PS.CU can also document DOC-CI the consent information CI, CI.j, CI.k, CI.l in a distributed consent ledger CLDG by sending the consent information CI, CI.j, CI.k, CI.l to another computation unit which creates the further data block CDB.i, CDB.l and inserts the further data block CDB.i, . . . , CDB.l into the distributed consent ledger CLDG, and by verifying that a further data block CDB.i, . . . , CDB.l comprising the consent information CI, CI.j, CI.k, CI.l is validly inserted into the distributed consent ledger CLDG.

The second embodiment furthermore comprises the steps of receiving REC-PI2 a second identifier PID2 of the patient PAT with the interface PS.IF, of determining DET-OI ownership information OI, OI.j, OI.k, OI.l with the computation unit PS.CU, wherein the ownership information OI, OI.j, OI.k, OI.l comprises an ownership signature OSGN, OSGN.j, OSGN.l, OSGN.l based on the medical data record MDR, MDR.j, MDR.k, MDR.l, wherein the ownership signature OSGN, OSGN.j, OSGN.l, OSGN.l is signed with the second identifier PID2 of the patient PAT, and of documenting DOC-OI the ownership information OI, OI.j, OI.k, OI.l in a distributed ownership ledger OLDG with the computation unit PS.CU.

In this embodiment, the second identifier PID2 of the patient PAT comprises a pair of a second private key PAT.PRK1, PAT.j.PRK2, PAT.k.PRK2, PAT.l.PRK2 and a second public key PAT.PBK2, PAT.j.PBK2, PAT.k.PBK2, PAT.l.PBK2, and the ownership information OI, OI.j, OI.k, OI.l comprises a hash H(MDR), H2(MDR.j), H2(MDR.k), H2(MDR.l) of the medical data record MDR, MDR.j, MDR.k, MDR.l and the ownership signature OSGN, OSGN.j, OSGN.l, OSGN.l, wherein the ownership signature OSGN, OSGN.j, OSGN.l, OSGN.l is a signature of the hash H(MDR), H2(MDR.j), H2(MDR.k), H2(MDR.l) of the medical data record MDR, MDR.j, MDR.k, MDR.l with the second private key PAT.PRK2, PAT.j.PRK2, PAT.k.PRK2, PAT.l.PRK2 of the second identifier PID2 of the patient PAT.

In this embodiment, the first identifier PID1 of the patient PAT is the first public key PAT.PBK1, PAT.j.PBK1, PAT.k.PBK1, PAT.l.PBK1 related to the first private key PAT.PRK1, PAT.j.PRK1, PAT.k.PRK1, PAT.l.PRK1 used for signing the medical data record MDR, MDR.j, MDR.k, MDR.l and/or on the identifier AEID, AEID.j, AEID.k, AEID.l of the authorized entity AE. The consent information CI, CI.j, CI.k, CI.l then comprises the consent signature CSGN, CSGN.j, CSGN.k, CSGN.l and the first public key PAT.PBK2, PAT.j.PBK2, PAT.k.PBK2, PAT.l.PBK2. Alternatively, the first identifier PID1 of the patient PAT received REC-PI1 is the first private key PAT.PRK1, PAT.j.PRK1, PAT.k.PRK1, PAT.l.PRK1 of the patient PAT. Alternatively, the consent information CI, CI.j, CI.k, CI.l can also be determined on the patient client PC, in this case, the first identifier PID1 of the patient PAT can be identified with the consent information CI, CI.j, CI.k, CI.l itself.

In this embodiment, the step of documenting DOC-OI the ownership information OI.j, OI.k, OI.l is executed by inserting a further data block ODB.i, . . . , ODB.l into the distributed ownership ledger OLDG, wherein the further data block ODB.i, . . . , ODB.l comprises the ownership information OI.j, OI.k, OI.l. It is possible that the further data block ODB.i, . . . , ODB.l does comprise several ownership informations OI.j, OI.k, OI.l, or other data beside the ownership information OI.j, OI.k, OI.l. The computation unit S.CU can also document DOC-OI the ownership information OI.j, OI.k, OI.l in a distributed ownership ledger OLDG by sending the ownership information OI.j, OI.k, OI.l to another computation unit which creates the further data block ODB.i, . . . , ODB.l and inserts the further data block ODB.i, . . . , ODB.l into the distributed ownership ledger OLDG, and by verifying that a further data block ODB.i, . . . , ODB.l comprising the ownership information OI.j, OI.k, OI.l is validly inserted into the distributed ownership ledger OLDG.

Figure 3:
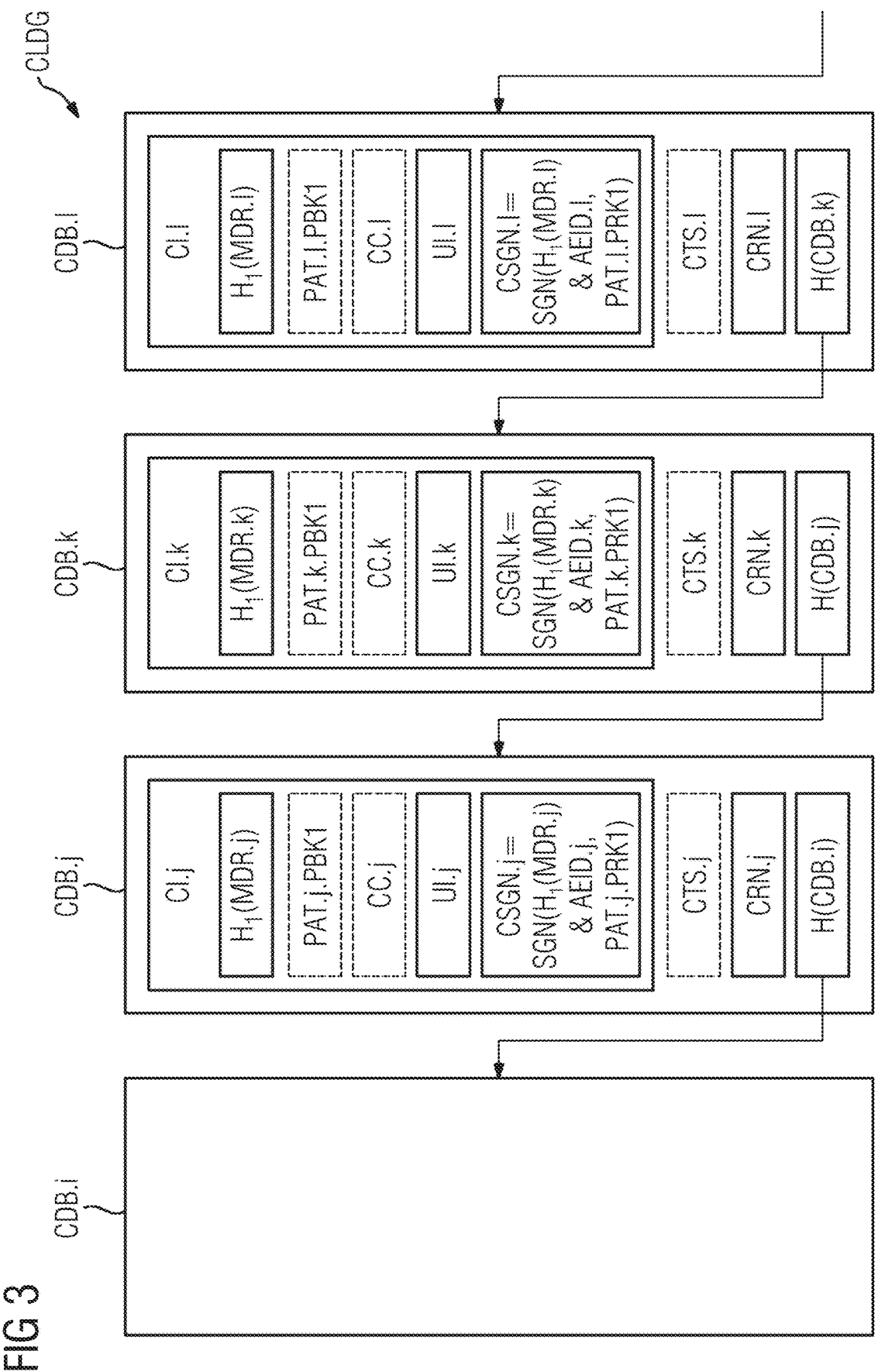
Figure 4:
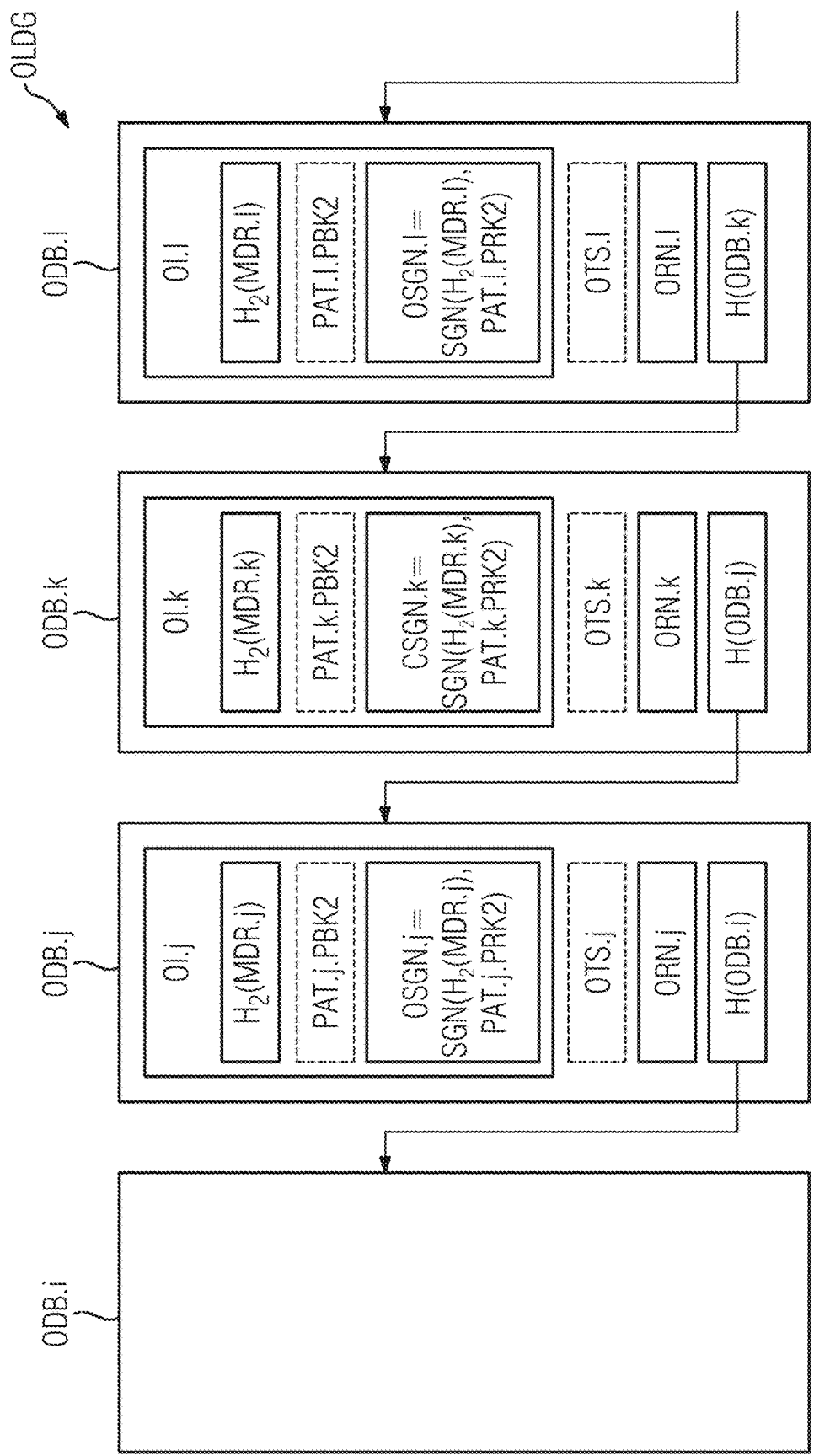

FIG. 3 displays data blocks CDB.i, . . . , CDB.l of an embodiment of a distributed consent ledger CLDG, FIG. 4 displays data blocks ODB.i, . . . , ODB.l of an embodiment of a distributed ownership ledger OLDG. In these embodiments, both the distributed consent ledger CLDG and the distributed ownership ledger OLDG are blockchains. Alternatively, the distributed consent ledger CLDG and/or the distributed ownership ledger OLDG can have a tree structure or the structure of a directed acyclic graph (another name is "tangle"). It is not essential that both the distributed consent ledger CLDG and the distributed ownership ledger OLDG have the same structure. In particular, the distributed consent ledger CLDG and the distributed ownership ledger OLDG can be identical. Furthermore, both the distributed consent ledger CLDG and the distributed ownership ledger OLDG can contain other data blocks not storing consent information CI.j, CI.k, CI.l or ownership information OI.j, OI.k, OI.l.

The data blocks CDB.j, . . . , CDB.l of the distributed consent ledger CLDG comprise consent information CI.j, . . . , CI.l, a timestamp CTS.j, . . . , CTS.l, a nonce CRN.j, . . . , CRN.l and a hash H(CDB.i), . . . , H(CDB.k) of the preceding data block CDB.j, . . . , CDB.l of the distributed consent ledger CLDG. The data blocks ODB.j, . . . , ODB.l of the distributed ownership ledger OLDG comprise ownership information OI, OI.j, . . . , OI.l, a timestamp OTS.j, . . . , OTS.l, a nonce ORN.j, . . . , ORN.l and a hash H(ODB.i), . . . , H(ODB.k) of the preceding data block ODB.j, ODB.l of the distributed ownership ledger OLDG.

In particular, a data block CDB.j, . . . , CDB.l of the distributed consent ledger CLDG can comprise several consent information CI.j, . . . , CI.l related to different medical data records MDR.j, MDR.k, MDR.l. The different medical data records MDR.j, MDR.k, MDR.l may be related to different patients PAT, but the different medical data records MDR.j, MDR.k, MDR.l may also be related to the same patient PAT. In particular, a data block ODB.j, . . . , ODB.l of the distributed ownership ledger OLDG can comprise several ownership information OI.j, . . . , OI.l related to different medical data records MDR.j, MDR.k, MDR.l. The different medical data records MDR.j, MDR.k, MDR.l may be related to different patients PAT, but the different medical data records MDR.j, MDR.k, MDR.l may also be related to the same patient PAT.

In this embodiment of the distributed consent ledger CLDG, the consent information CI.j, CI.k, CI.l comprises a hash H1(MDR.j), H1(MDR.k), H1(MDR.l) of the medical data record MDR.j, MDR.k, MDR.l, a usage information UI.j, UI.k, UI.l and a consent signature CSGN.j, CSGN.k, CSGN.l. Furthermore, the consent information CI.j, CI.k, CI.l comprises a first public key PAT.j.PBK1, . . . , PAT.l.PBK1 of the patient PAT being subject of the respective medical data record MDR.j, MDR.k, MDR.l. Furthermore, the consent information CI.j, CI.k, CI.l comprises an amount of cryptocurrency CC.j, CC.k, CC.l to be paid if using the respective medical data record MDR.j, MDR.k, MDR.l. In this embodiment, the consent signature is calculated as $$CSGN.j = SGN(H1(MDR.j)\ \&\ AEID.j, PAT.j.PRK1)$$

$$CSGN.k = SGN(H1(MDR.k)\ \&\ AEID.k, PAT.k.PRK1)$$

$$CSGN.l = SGN(H1(MDR.l)\ \&\ AEID.l, PAT.l.PRK1)$$

In other words, the consent signature CSGN.j, CSGN.k, CSGN.l is a based on a concatenation of the hash H1(MDR.j), H1(MDR.k), H1(MDR.l) of the medical data record MDR.j, MDR.k, MDR.l and the identifier AEID.j, AEID.k, AEID.l of the respective authorized entity AE; and the consent signature CSGN.j, CSGN.k, CSGN.l is signed with a first private key PAT.j.PRK1, PAT.k.PRK1, PAT.l.PRK1 of the patient PAT the medical data record MDR.j, MDR.k, MDR.l is related to (which corresponds to the first public key PAT.j.PBK1, . . . , PAT.l.PBK1 of the patient PAT). Alternatively, the consent signature CSGN.j, CSGN.k, CSGN.l can be based on a concatenation of the hash H1(MDR.j), H1(MDR.k), H1(MDR.l) of the medical data record MDR.j, MDR.k, MDR.l, the identifier AEID.j, AEID.k, AEID.l of the respective authorized entity AE and the usage information:

$$CSGN.j = SGN(H1(MDR.j)\ \&\ AEID.j\ \&\ UI.j, PAT.j.PRK1)$$

$$CSGN.k = SGN(H1(MDR.k)\ \&\ AEID.k\ \&\ UI.k, PAT.k.PRK1)$$

$$CSGN.l = SGN(H1(MDR.l)\ \&\ AEID.l\ \&\ UI.l, PAT.l.PRK1)$$

Furthermore, the consent signature CSGN.j, CSGN.k, CSGN.l can also be based on a concatenation with the first public key PAT.j.PBK1, . . . , PAT.l.PBK1 of the patient PAT being subject of the respective medical data record MDR.j, MDR.k, MDR.l, or with the amount of cryptocurrency CC.j, CC.k, CC.l to be paid if using the respective medical data record MDR.j, MDR.k, MDR.l.

In particular, the usage information UI.j, UI.k, UI.l can comprise the usage of the medical data record MDR.j, MDR.k, MDR.l the patient PAT consented to. For example, the usage information UI.j, UI.k, UI.l can comprise an array of strings or other variables indicating the allowed usage types, for example ["train_ai", "reference" ] for indicating that the medical data record MDR.j, MDR.k, MDR.l may be used for training an artificial intelligence algorithm or as reference case for similar cases. Alternatively, the usage information UI.j, UI.k, UI.l can also be a string, for example "train_ai/reference". Alternatively, the usage information UI.j, UI.k, UI.l can be an integer referring to specific usage (for example, 0 for no usage, 1 for "train_ai", 2 for "reference", and 3 for "train_ai/reference").

In particular, the amount of cryptocurrency CC.j, CC.k, CC.l to be paid if using the respective medical data record MDR.j, MDR.k, MDR.l can be given as number. In particular, the amount of cryptocurrency CC.j, CC.k, CC.l to be paid if using the respective medical data record MDR.j, MDR.k, MDR.l can be contained in a smart contract stored in the consent information CI.j, CI.k, CI.l data block CDB.j, . . . , CDB.l of the distributed consent ledger CLDG, wherein the smart contract regulates the transfer of cryptocurrency in the case of a usage of the respective medical data record MDR.j, MDR.k, MDR.l.

In this embodiment of the ownership consent ledger OLDG, the ownership information OI.j, OI.k, OI.l comprises a hash H2(MDR.j), H2(MDR.k), H2(MDR.l) of the medical data record MDR.j, MDR.k, MDR.l and a ownership signature OSGN.j, OSGN.k, OSGN.l. In this embodiment, the ownership signature OSGN.j, OSGN.l, OSGN.l is calculated as $$OSGN.j=SGN(H2(MDR.j),PAT.j.PRK2)$$

$$OSGN.k=SGN(H2(MDR.k),PAT.k.PRK2)$$

$$OSGN.1=SGN(H2(MDR.l),PAT.l.PRK2)$$

In other words, the ownership signature OSGN.j, OSGN.k, OSGN.l is a based on the hash H2(MDR.j), H2(MDR.k), H2(MDR.l) of the medical data record MDR.j, MDR.k, MDR.l; and the ownership signature OSGN.j, OSGN.k, OSGN.l is signed with a second private key PAT.j.PRK2, PAT.k.PRK2, PAT.l.PRK2 of the patient PAT the medical data record MDR.j, MDR.k, MDR.l is related to. In a preferred embodiment, the ownership information OI.j, OI.k, OI.l can also comprise a second public key PAT.j.PBK2, PAT.k.PBK2, PAT.l.PBK2 of the patient PAT, wherein the second public key PAT.j.PBK2, PAT.k.PBK2, PAT.l.PBK2 and the second private key PAT.j.PRK2, PAT.k.PRK2, PAT.l.PRK2 form an asymmetric key pair. This second public key PAT.j.PBK2, PAT.k.PBK2, PAT.l.PBK2 can be used for directing payments of cryptocurrency to an account of the patient PAT, wherein the account is identified by the second public key PAT.j.PBK2, PAT.k.PBK2, PAT.l.PBK2. Furthermore, this second public key PAT.j.PBK2, PAT.k.PBK2, PAT.l.PBK2 can also be included into the ownership signature OSGN.j, OSGN.k, OSGN.l.

It has to be understood that the consent information CI.j, CI.k, CI.l and the ownership information OI.j, OI.k, OI.l displayed in FIG. 3 and FIG. 4 are only a certain embodiment of the consent information CI.j, CI.k, CI.l and the ownership information OI.j, OI.k, OI.l contained in the distributed consent ledger CLDG and the distributed ownership ledger OLDG. Both the consent information CI.j, CI.k, CI.l and the ownership information OI.j, OI.k, OI.l can comprise additional data or less data compare with the consent information CI.j, CI.k, CI.l and the ownership information OI.j, OI.k, OI.l displayed in FIG. 3 and FIG. 4.

In these embodiments of the distributed consent ledger CLDG and the distributed ownership ledger OLDG, the hash H1(MDR.j), H1(MDR.k), H1(MDR.l) contained in the consent information CI.j, CI.k, CI.l (which is equal to the hash H1(MDR.j), H1(MDR.k), H1(MDR.l) the consent signature CSGN.j, CSGN.k, CSGN.l is based on) is equal to the hash H2(MDR.j), H2(MDR.k), H2(MDR.l) contained in the ownership information OI.j, OI.k, OI.l (which is equal to the hash H2(MDR.j), H2(MDR.k), H2(MDR.l) the ownership signature OSGN.j, OSGN.k, OSGN.l is based on). Alternatively, the hash H1(MDR.j), H1(MDR.k), H1(MDR.l) contained in the consent information CI.j, CI.k, CI.l can be different from the hash H2(MDR.j), H2(MDR.k), H2(MDR.l) contained in the ownership information OI.j, OI.k, OI.l, in particular, they can be calculated with different seeds or with different hash functions.

In these embodiments of the distributed consent ledger CLDG and the distributed ownership ledger OLDG, the first private key PAT.j.PRK1, PAT.k.PRK1, PAT.l.PRK1 of the patient PAT and the second private key PAT.j.PRK2, PAT.k.PRK2, PAT.l.PRK2 of the patient PAT are different. Alternatively, the first private key PAT.j.PRK1, PAT.k.PRK1, PAT.l.PRK1 of the patient PAT and the second private key PAT.j.PRK2, PAT.k.PRK2, PAT.l.PRK2 of the patient PAT can be identical.

In this embodiment, the timestamp CTS.j, . . . , CTS.l, OTS.j, . . . , OTS.l of a data block CDB.j, . . . , CDB.l, ODB.j, . . . , ODB.l is the creation time of the data block CDB.j, . . . , CDB.l, ODB.j, . . . , ODB.l. Alternatively, the timestamp CTS.j, . . . , CTS.l, OTS.j, . . . , OTS.l of a data block CDB.j, . . . , CDB.l, ODB.j, . . . , ODB.l can be the creation time of the consent information CI.j, . . . , CI.l or the ownership information OI.j, OI.l contained in the data block CDB.j, . . . , CDB.l, ODB.j, ODB.l.

In general, a nonce CRN.j, . . . , CRN.l, ORN.j, . . . , ORN.l is a data item that can be chosen arbitrarily by the creator of the data block CDB.i, . . . , CDB.l, ODB.i, . . . , ODB.j without affecting the actual content of the data block CDB.i, . . . , CDB.l, ODB.i, . . . , ODB.j. In particular, the usage and/or the content of the consent information CI.j, . . . , CI.l and the usage and/or the content of the ownership information OI.j, . . . , OI.l are not affected by the choice of the nonce CRN.j, . . . , CRN.l, ORN.j, . . . , ORN.l. In general, changing the nonce CRN.j, . . . , CRN.l, ORN.j, . . . , ORN.l also changes a hash H(CDB.i), . . . , H(CDB.k), H(ODB.i), . . . , H(ODB.k) of the data block CDB.i, . . . , CDB.l, ODB.i, . . . , ODB.j.

In these embodiments of the distributed consent ledger CLDG and the distributed ownership ledger OLDG, for every data block CDB.j, . . . , CDB.l of the distributed consent ledger CLDG related to a medical data record MDR.j, MDR.k, MDR.l there is a corresponding data block ODB.i, . . . , ODB.j of the distributed ownership ledger OLDG related to the same medical data record MDR.j, MDR.k, MDR.l. In general, there can be data blocks CDB.j, . . . , CDB.l of the distributed consent ledger CLDG related to a medical data record MDR.j, MDR.k, MDR.l with no corresponding data block ODB.i, . . . , ODB.j of the distributed ownership ledger OLDG related to the same medical data record MDR.j, MDR.k, MDR.l, or with two or more corresponding data blocks ODB.i, . . . , ODB.j of the distributed ownership ledger OLDG related to the same medical data record MDR.j, MDR.k, MDR.l. In general, there can be data blocks ODB.i, . . . , ODB.j of the distributed ownership ledger OLDG related to a medical data record MDR.j, MDR.k, MDR.l with no corresponding data block CDB.j, . . . , CDB.l of the distributed consent ledger CLDG related to the same medical data record MDR.j, MDR.k, MDR.l, or with two or more corresponding data blocks CDB.j, . . . , CDB.l of the distributed consent ledger CLDG related to the same medical data record MDR.j, MDR.k, MDR.l.

In particular, for inserting a data block CDB.i, . . . , CDB.l, ODB.i, . . . , ODB.l into the distributed consent ledger CLDG or the distributed ownership ledger OLDG, a consensus algorithm (e.g. proof of work, proof of storage, proof of stake, proof of elapsed time) must be executed, wherein the consensus algorithm may be based on the nonce CRN.j, ..., CRN.l, ORN.j, ..., ORN.l of the data block CDB.i, ..., CDB.l, ODB.i, ..., ODB.l to be inserted. In this embodiment, the nonce CRN.j, ..., CRN.l, ORN.j, ..., ORN.l must be chosen by the creator of the data block CDB.j, ..., CDB.l, ODB.j, ..., ODB.l such that the hash H(CDB.j), ..., H(CDB.l), H(ODB.j), ..., H(ODB.l) of the data block CDB.j, ..., CDB.l, ODB.j, ..., ODB.l fulfills a certain condition. In this embodiment, the condition is that the hash H(CDB.j), ..., H(CDB.l), H(ODB.j), ..., H(ODB.l) of the data block CDB.j, ..., CDB.l, ODB.j, ..., ODB.l is smaller than a given threshold.

In this embodiment, the hash H(CDB.j), H(CDB.k) of a data block CDB.j, CDB.k of the distributed consent ledger CLDG is calculated as $$H(CDB.j)=SHA256(H(CI.j)\& H(CDB.i)\& CRN.j)$$

$$H(CDB.k)=SHA256(H(CI.k)\& H(CDB.j)\& CRN.k),$$

wherein the SHA256 hash function can be replaced with any other suitable hash function. The operation "&" can be understood as arithmetic addition of numbers or as concatenation of strings (by converting numbers to strings before the concatenation). The hash of the consent information CI.j, CI.k is calculated in this embodiment as $$H(CI.j)=SHA256[(MDR.j)\& H(UI.j)\& SGN\\((MDR.j)\& AEID.j,PAT.j.PRK1)]bzw.$$

$$H(CI.k)=SHA256[(MDR.k)\& H(UI.k)\& SGN\\((MDR.k)\& AEID.k,PAT.k.PRK1)],$$

wherein the SHA256 hash function can be replaced with any other suitable hash function. In particular, the hash H1(MDR.j), H1(MDR.k) of the medical data record MDR.j, MDR.k can be the Merkle root of the medical data record MDR.j, MDR.k. Alternatively, the hash H(CDB.j), H(CDB.k) of the data block CDB.j, CDB.k can also be based on other data items contained in the data block CDB.j, CDB.k, in particular on the timestamp CTS.j, CTS.k of the data block CDB.j, CDB.k. Alternatively, the hash H(CDB.j), H(CDB.k) of the data block CDB.j, CDB.k can be based on other items contained in the data block CDB.j, CDB.k.

In this embodiment, the hash H(ODB.j), H(ODB.k) of a data block ODB.j, ODB.k of the distributed ownership ledger OLDG is calculated as $$H(ODB.j)=SHA256(H(OI.j)\& H(ODB.i)\& ORN.j)\\bzw.$$

$$H(ODB.k)=SHA256(H(OI.k)\& H(ODB.j)\& ORN.k),$$

wherein the SHA256 hash function can be replaced with any other suitable hash function. The operation "&" can be understood as arithmetic addition of numbers or as concatenation of strings (by converting numbers to strings before the concatenation). The hash of the ownership information OI.j, OI.k is calculated in this embodiment as $$H(OI.j)=SHA256[(MDR.j)\& SGN((MDR.j),\\PAT.j.PRK2)],$$

$$H(OI.k)=SHA256[(MDR.k)\& SGN((MDR.k),\\PAT.k.PRK2)],$$

wherein the SHA256 hash function can be replaced with any other suitable hash function. In particular, the hash H2(MDR.j), H2(MDR.k) of the medical data record MDR.j, MDR.k can be the Merkle root of the medical data record MDR.j, MDR.k. Alternatively, the hash H(ODB.j), H(ODB.k) of the data block ODB.j, ODB.k can also be based on other data items contained in the data block ODB.j, ODB.k, in particular on the timestamp OTS.j, OTS.k of the data block ODB.j, ODB.k. Alternatively, the hash H(ODB.j), H(ODB.k) of the data block ODB.j, ODB.k can be based on other items contained in the data block ODB.j, ODB.k.

In FIG. 3 and FIG. 4 only a subset data blocks CDB.i, CDB.l, ODB.i, ..., ODB.l of the distributed consent ledger CLDG and the distributed ownership ledger OLDG are displayed, furthermore, also the contents of the data blocks CDB.i, ..., CDB.l, ODB.i, ..., ODB.l are displayed only for a subset of the data blocks CDB.i, ..., CDB.l, ODB.i, ..., ODB.l. In general, the distributed consent ledger CLDG and the distributed ownership ledger OLDG can comprise additional data blocks and additional items of the data blocks, and the data blocks CDB.i, ..., CDB.l, ODB.i, ..., ODB.l can be linked to these additional data blocks.

Furthermore, the distributed consent ledger CLDG and the distributed ownership ledger OLDG are blockchains in FIG. 3 and FIG. 4. Alternatively, the distributed consent ledger CLDG and/or the distributed ownership ledger OLDG can be realized as a block tree, meaning that there can be several data blocks CDB.i, ..., CDB.l, ODB.i, ..., ODB.l comprising the hash H(CDB.i), ..., H(CDB.k), H(ODB.i), ..., H(ODB.k) of a certain data block CDB.i, ..., CDB.k, ODB.i, ..., ODB.k. Alternatively, the distributed consent ledger CLDG and/or the distributed ownership ledger OLDG can be realized as a tangle, meaning that every data block CDB.i, ..., CDB.l, ODB.i, ..., ODB.l can comprise an arbitrary number of hashes H(CDB.i), ..., H(CDB.k), H(ODB.i), ..., H(ODB.k) of certain other data blocks CDB.i, ..., CDB.k, ODB.i, ..., ODB.k. In other words, a tangle has the structure of a directed acyclic graph. In particular, every data block CDB.i, ..., CDB.l, ODB.i, ..., ODB.l can comprise a fixed number of hashes H(CDB.i), ..., H(CDB.k), H(ODB.i), ..., H(ODB.k) of certain other data blocks CDB.i, ..., CDB.k, ODB.i, ..., ODB.k, in particular, this fixed number can be two.

Figure 5:
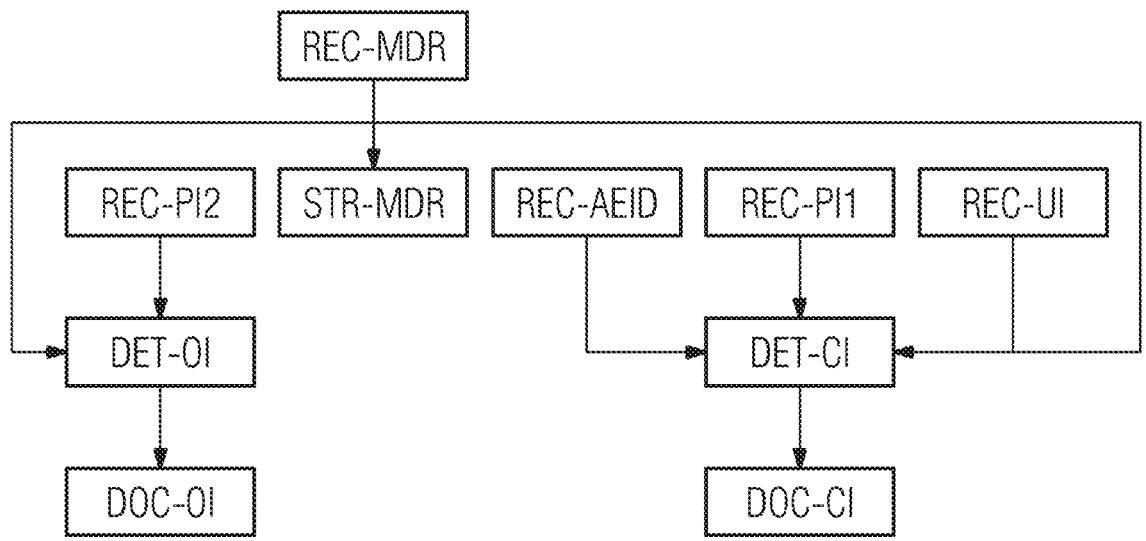

FIG. 5 displays a flowchart of an embodiment a method for storing STR-MDR a medical data record MDR, MDR.j, MDR.k, MDR.l with a memory unit PS.MU. The displayed embodiment comprises all the steps of the second embodiment of the method for providing PROV-URL a uniform resource locator URL displayed in FIG. 2, except the steps of determining DET-URL and providing PROV-URL the uniform resource locator URL. The remaining steps can comprise all advantageous and/or alternative features and/or embodiments of the respective steps of the second embodiment. Steps marked as optional in FIG. 2 are also optional in this embodiment.

The displayed method for storing STR-MDR a medical data record MDR, MDR.j, MDR.k, MDR.l can be used for storing STR-MDR medical data records MDR, MDR.j, MDR.k, MDR.l and granting access to medical data records MDR, MDR.j, MDR.k, MDR.l, without a necessary interaction by the user. In particular, within this embodiment the step of providing PROV-URL the uniform resource locator URL is not executed.

Figure 6:
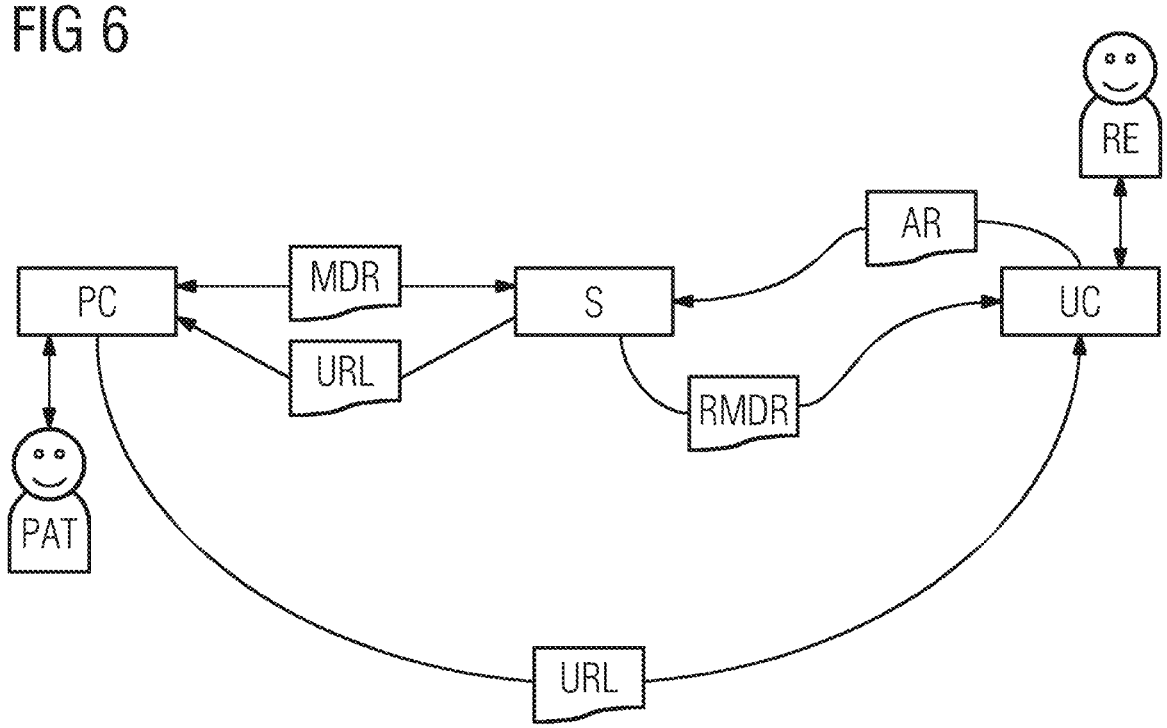
FIG. 6 displays a first embodiment of the data flow between patient client, server and user client FIG. 7 displays a second embodiment of the data flow between patient client, server and user client, FIG. 8 displays a detailed data flow between the patient client and the server for creating signatures, FIG. 9 displays a first embodiment of the method for using a uniform resource locator, FIG. 10 displays a second embodiment of the method for using a uniform resource locator, FIG. 11 displays an embodiment of the data flow between user client, server and trusted entity, FIG. 12 displays an embodiment of a patient client, a server and a user client, FIG. 13 displays a first embodiment of a providing system, FIG. 14 displays a second embodiment of a providing system, FIG. 15 displays a first embodiment of a usage system, FIG. 16 displays a second embodiment of a usage system, FIG. 17 displays an embodiment of the method for method for providing a location information, FIG. 18 displays an embodiment of the method for storing consent.

FIG. 6 displays a first embodiment of the overall data flow between the patient client PC, the server S and the user client UC. In particular, the patient client PC and the server S can be contained in a providing system PS, and the server S and/or the user client UC can be contained in a usage system US.

In this embodiment, the medical data record MDR can be sent from the patient client PC to the server S and/or the medical data record MDR can be sent from the server S to the patient client PC. Alternatively, the hash H(MDR) of the medical data record MDR can be sent from the patient client PC to the server S, and/or the hash H(MDR) of the medical data record MDR can be sent from the server S to the patient client PC.

The uniform resource located URL is based on the medical data record MDR and is sent from the server S to the patient client PC. In particular, the uniform resource locator URL can be used to access the medical data record MDR stored in the server S.

The patient PAT is now able to share access to the medical data record MDR by providing the uniform resource locater URL to a requesting entity RE, in particular by sending the uniform resource locator URL from the patient client PC to a user client UC related to the requesting entity RE. In particular, the requesting entity RE may be a physician of the patient PAT which can use the medical data record MDR for diagnostic purpose.

The requesting entity RE may access the medical data record MDR by issuing an access request AR, the access request AR being based on the uniform resource locator URL, and sending the access request AR to the server S. The server S than identifies the medical data record MDR based on the access request AR and provides the medical data record MDR to the requesting entity RE, in particular to the user client UC of the requesting entity RE.

Figure 7:
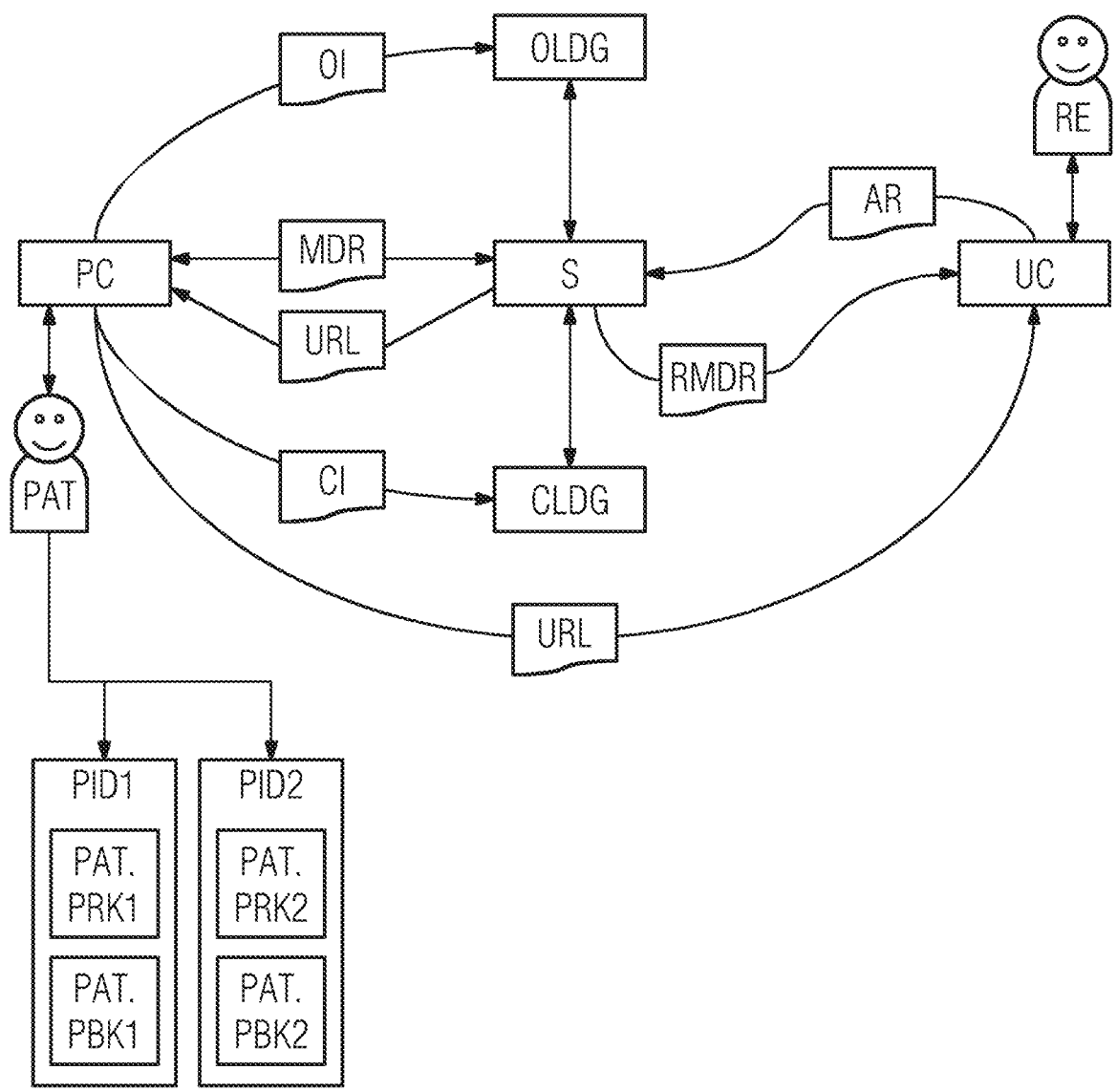

FIG. 7 displays a second embodiment of the overall data flow between the patient client PC, the server S and the user client UC. The second embodiment is based on the first embodiment of the overall data flow, furthermore comprising a distributed ownership ledger OLDG and a distributed consent ledger CLDG, wherein both the patient client PC and the server S can access or interact with both the distributed consent ledger CLDG and the distributed ownership ledger OLDG.

In this second embodiment, there is a first identity PID1 of the patient PAT, comprising a first private key PAT.PRK1 and a related first public key PAT.PBK1, and there is a second identity PID2, comprising a second private key PAT.PRK2 and a related second public key PAT.PBK2.

In this embodiment, the patient client PC receives the medical data record MDR from the server S, wherein the medical data record MDR was uploaded to the server S by the entity creating the medical data record MDR. Alternatively, the patient client PC can also directly receive the medical data record MDR without involvement of the server S. Alternatively, the patient client PC can receive a hash H(MDR) of the medical data record MDR from the server S.

In this embodiment, the patient client PC determines DET-CI, DET-OI the consent information CI and/or the ownership information OI, by optionally calculating a hash H(MDR) of the medical data record MDR (if the medical data record MDR and not the hash H(MDR) of the medical data record MDR was received by the patients client PC), and by optionally creating signatures by signing with its first private key PAT.PRK1 and/or with its second private key PAT.PRK2, wherein the signatures are included in the consent information CI and/or the ownership information OI. Furthermore, the patient client PC directly documents DOC-CI, DOC-OI the ownership information OI in the distributed consent ledger CLDG and/or the distributed ownership ledger OLDG.

If the medical data record MDR was not received by the patient client PC from the server S, the patient client PC also transmits the medical data record MDR to the server S.

In this second embodiment, the server S can perform checks CHK-1, CHK-2, CHK-3 based on the access request AR, requesting in whether the server S is allowed to provide the medical data record MDR to the user client UC. The checks can be based on an interaction of the server S with the distributed consent ledger CLDG and/or the distributed ownership ledger OLDG.

Figure 8:
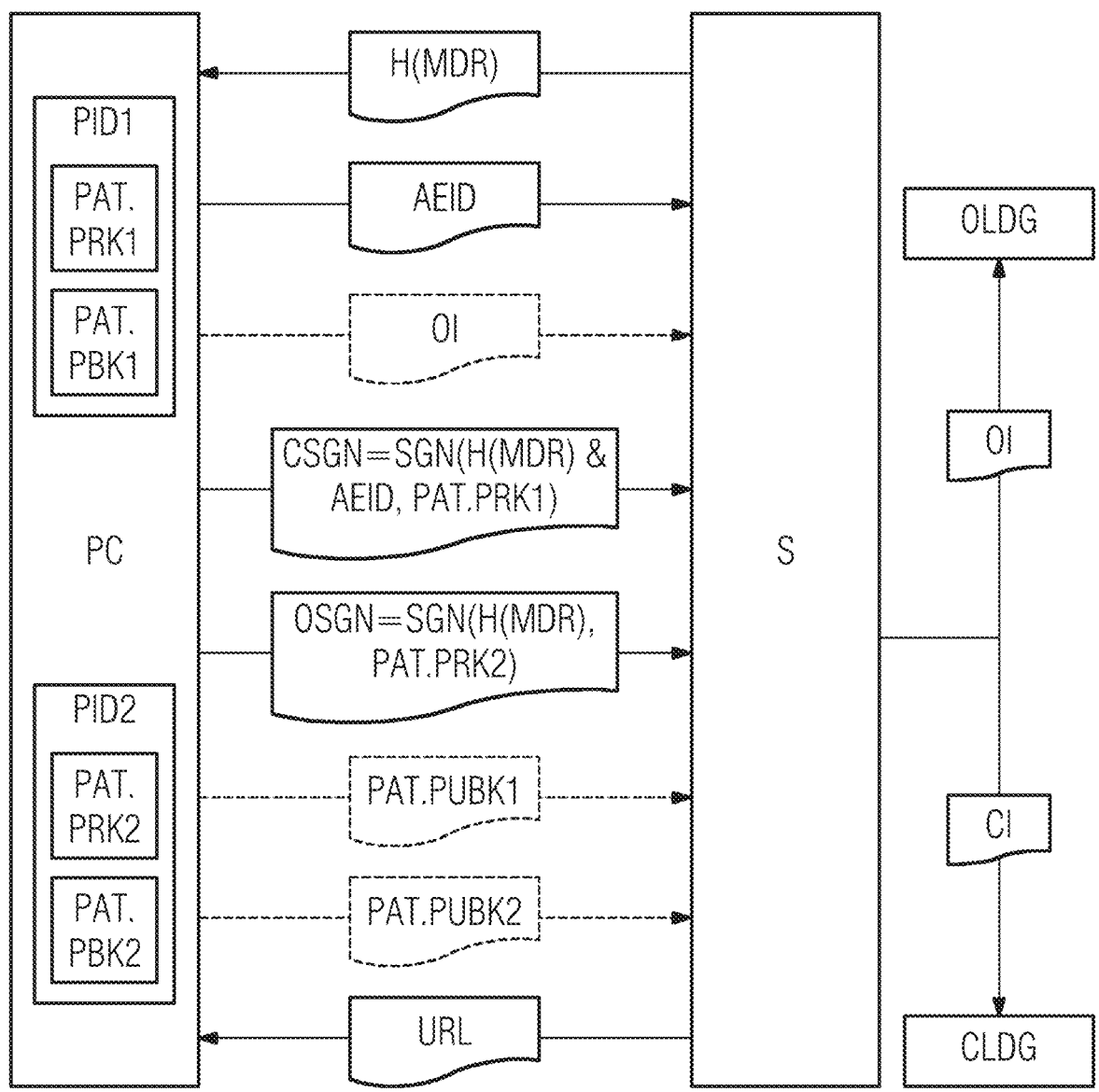

FIG. 8 displays a detailed embodiment of the data exchange between the patient client PC and the server S. The patient client PC and the server S can be part of a providing system PS. In particular, in this detailed embodiment, the consent information CI and the ownership information OI can be created without the server S having access to one of the private keys PAT.PRK1, PAT.PRK2 of the patient PAT, and without the necessity to transfer the medical data record MDR from the server S to the patient client PC.

In this embodiment, the server S receives the medical data record MDR from the data source, e.g. from a medical apparatus, and calculates a hash H(MDR) of the medical data record MDR. Subsequently, the server S sends the hash H(MDR) of the medical data record MDR to the patient client PC. Optionally, the server Scan additionally send metadata related to the medical data record MDR to the patient client PC.

Using the patient client PC, the patient PAT can specify an authorized entity AE which should have access to the medical data record MDR. In particular, the patient client PC can determine the identifier AEID of the authorized entity AE and send the identifier AEID of the authorized entity to the server S. Furthermore, the patient PAT can optionally specify a usage information UI that governs the usage of the medical data record MDR, and send the usage information UI from the patient client PC to the server S.

Furthermore, the patient client PC can create the consent signature CSGN and/or the ownership signature OSGN. In this embodiment, the consent signature CSGN is calculated as $$CSGN=SGN(H(MDR)\& \: AEID, PAT.PRK1),$$

in particular signed with the first private key PAT.PRK1 of the patient PAT, and the ownership signature OSGN is calculated as $$OSGN=SGN(H(MDR), PAT.PRK2),$$

in particular signed with the second private key PAT.PRK2 of the patient PAT. Furthermore, the patient client PC can also provide the first public key PAT.PBK1 and/or the second public key PAT.PBK2 to the server S. The server S determines the consent information CI and/or the ownership information OI based on the consent signature CSGN and/or the ownership signature OSGN and documents the consent information CI and/or the ownership information OI in the distributed consent ledger CLDG and/or the distributed ownership ledger OLDG.

Wherever not already described explicitly, individual embodiments, or their individual embodiments and features, described in relation to the drawings can be combined or exchanged with one another without limiting or widening the scope of the described invention, whenever such a combination or exchange is meaningful and in the sense of this invention. Advantageous which are described with respect to one embodiment of the present invention or with respect to one figure are, wherever applicable, also advantages of other embodiments of the present invention.

Figure 9:
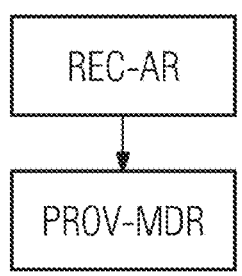

FIG. 9 displays a first embodiment of the method for using a uniform resource locator URL provided by a method for providing the uniform resource locator URL.

The first step of the displayed first embodiment is receiving REC-AR an access request AR directed to a requested medical data record RMDR by an interface US.IF, wherein the requested medical data record RMDR is stored within a memory unit US.MU, and wherein the access request AR is based on the uniform resource locator URL. In this embodiment, the interface US.IF is the interface of the usage system US, in particular, the interface US.IF can be identical with an interface S.IF of the server S. Furthermore, the memory unit US.MU is a memory unit US.MU of the usage system, in particular, the memory unit US.MU can be identical with a memory unit S.MU of the server S. In particular, the memory unit S.MU of the server S can comprise a repository. In particular, the usage system US can be identical with the server S.

In this embodiment, the access request AR is a HTTP GET request or an HTTP POST request based on the uniform resource locator URL. For example, the uniform resource locator URL can be "http://cloud-storage.com/data/ct/mdr_1.dat? auth=7597655124", and the access request AR can be the following HTTP GET request:

GET/data/ct/mdr_1.dat?auth=7597655124 HTTP/1.1
Host: cloud-storage.com

Alternatively, the access request AR can be the following HTTP POST request:

POST/data/ct/mdr_1.dat HTTP/1.1
Host: cloud-storage.com
Content-Type: application/x-www-form-urlencoded
Content-Length: 15
auth=7597655124

The second step of the displayed second embodiment is providing PROV-MDR the requested medical data record RMDR based on the access request AR with the interface US.IF.

In this embodiment, the requested medical data record RMDR is provided to the user client UC by a HTTP response as response to the HTTP GET request or the HTTP POST request. The header of the HTTP response can for example HTTP/1.1200 OK
Server: Apache/1.3.29 (Unix) PHP/4.3.4
Content-Length: 123456
Connection: close
Content-Type: application/x-tar The requested medical data record RMDR is then contained in the body of the HTTP response.

Alternatively the location of the requested medical data record RMDR can also be contained in the uniform resource locator URL as query parameter. For example, in the uniform resource locator URL "http://cloud-storage.com-?mdr=3694721586& auth=7597655124" the location of the requested medical data record RMDR is given by the query parameter "mdr=3694721586", and the memory unit US.MU maps the given parameter to the location of the medical data record MDR, MDR.j, MDR.k, MDR.l in the file system of the memory unit US.MU and/or of the repository of the server S. In particular, in this case there can be intermediate HTTP requests and responses. For example, there can be a HTTP GET request from the user client UC to the memory unit US.MU containing the following data:

GET/get_data.php?mdr=3694721586&auth=
7597655124 HTTP/1.1
Host: cloud-storage.com The server S can answer with the following HTTP response, which resolves the location given as a query parameter into the location in the filesystem of the server S or the repository:

HTTP/1.0302 Found
Date: Wed, 4 Apr. 2011 15:12:44 GMT
Location: http://cloud-storage.com/data/ct/mdr_1.dat The user client UC can then initiate another HTTP GET request or HTTP POST request, as already described before, including the authorization token. Alternatively, the server S can already check the authorization token following the first request, and respond with the location in the filesystem of the memory unit US.MU or the repository in the case of a correct authorization.

In this embodiment, the access request AR is an HTTP request, and the requested medical data record RMDR was provided by an HTTP response. Alternatively other protocols can be uses for sending the access request AR from the user client UC to the server S and/or the memory unit US.MU, and for providing PROV-MDR the requested medical data record RMDR to the user client UC by the server S and/or the memory unit US.MU. Examples for such protocols are HTTPS, WebDAV, FTP, or other data transfer protocols known to the person skilled in the art.

Figure 10:
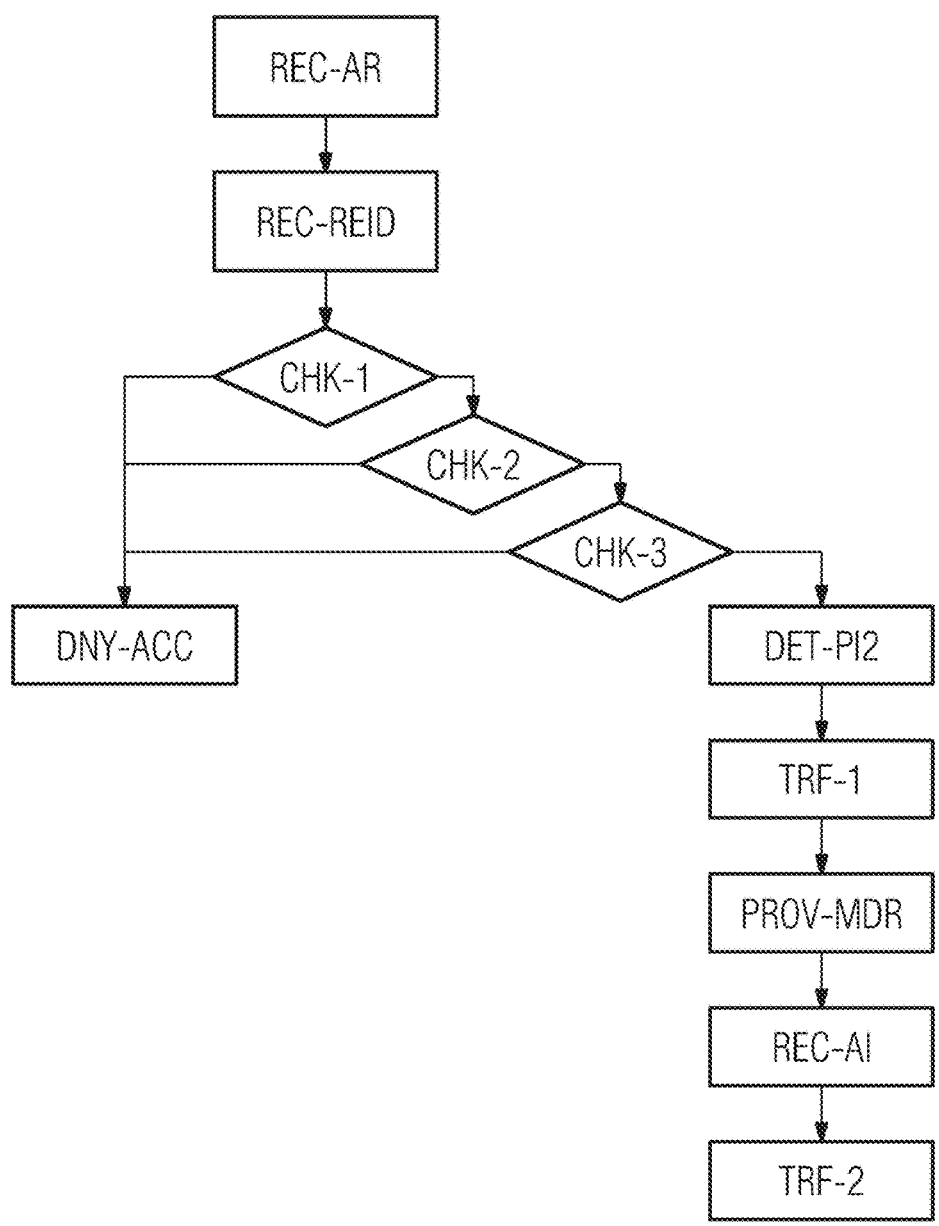

FIG. 10 displays a second embodiment of the method for using a uniform resource locator URL provided by a method for providing the uniform resource locator URL.

The second embodiment comprises the step of receiving REC-AR an access request AR, and the step of providing PROV-MDR the requested medical data record RMDR, both steps already described in the context of the first embodiment, which also can comprise all advantageous features and embodiments described in FIG. 10. All other steps can be considered as optional.

The second step of the second embodiment is receiving REC-REID an identifier of the requesting entity RE with the interface MU.IF. In particular, the identifier of the requesting entity RE is sent by the user client UC.

In this second embodiment, the identifier of the requesting entity RE is contained in the access request AR. Alternatively, the identifier of the requesting entity RE can also be received independently of the access request AR. In particular, the identifier of the requesting entity RE can be a part of the uniform resource locator URL or of a HTTP request based on the uniform resource locator URL.

In this second embodiment, the identifier of the requesting entity RE is based on access credentials, in particular, the identifier of the requesting entity RE comprises a shared secret and/or a digital certificate. Alternatively, the identifier of the requesting entity RE may be any data identifying, in particular uniquely identifying the requesting entity RE.

In particular, the identifier of the requesting entity RE can be identical with the authorization token contained in the uniform resource locator URL. In particular, the authorization token may be identical with the shared secret or the result of a function, in particular a hash function, applied to the shared secret. By applying the hash function or another function onto the shared secret an eavesdropper cannot obtain the shared secret by intercepting the communication between the user client UC and the usage system US and/or the server S.

In the displayed second embodiment, consent information CI, CI.j, . . . , CI.k based on medical data records MDR, MDR.j, MDR.k, MDR.l and on identifiers of authorized entities are documented in a distributed consent ledger CLDG. A further step of the displayed second embodiment is performing a first check CHK-1 whether the distributed consent ledger CLDG documents a consent information CI, CI.j, . . . , CI.k based on the requested medical data record RMDR and on the identifier of the requesting entity RE with a computation unit US.CU.

In this embodiment, the distributed consent ledger CLDG comprises consent information CI, CI.j, . . . , CI.k, wherein each consent information CI, CI.j, . . . , CI.k comprises a hash H(MDR), H1 (MDR.j), ..., H1 (MDR.l) of a medical data record MDR, MDR.j, MDR.k, MDR.l, a usage information UI, UI.j, ..., UI.l and a consent signature CSGN, CSGN.j, ..., CSGN.l, wherein a consent signature CSGN, CSGN.j, ..., CSGN.l is calculated as described with respect to FIG. 3.

In this embodiment, the consent ledger CLDG documents a consent information CI, CI.j, ..., CI.k based on the requested medical data record RMDR and on the identifier of the requesting entity RE, if there is a consent information CI, CI.j, ..., CI.k comprising the hash H(MDR), H1(MDR.j), H1(MDR.k), H1(MDR.l) of the medical data record MDR, MDR.j, MDR.k, MDR.l and a consent signature CSGN, CSGN.j, ..., CSGN.l based on the combination of the hash H(MDR), H1(MDR.j), H1(MDR.k), H1(MDR.l) of the medical data record MDR, MDR.j, MDR.k, MDR.l and the identifier of the requesting entity RE.

In particular, in order to perform the first check CHK-1, the usage system US and/or the server S computes the hash H(RMDR) of the requested medical data record RMDR, and determines all consent informations CI, CI.j, ..., CI.l of the distributed consent ledger CLDG comprising the hash H(RMDR) of the requested medical data record RMDR.

In particular, the identifier AEID, AEID.j, AEID.k, AEID.l of the authorized entity AE can comprise a public key related to the authorized entity AE, and a signature based on the public key related to the authorized entity, wherein the signature is signed with a private key of a certificate authority. The identifier AEID, AEID.j, AEID.k, AEID.l of the authorized entity AE can alternatively or additionally also comprise a signature of a data item with the private key related to the authorized entity (wherein the private key related to the authorized entity AE and the public key related to the authorized entity AE form a asymmetric key pair). In particular, the data item can be created by the usage system US and/or the server S and send to the authorized entity AE, signed by the authorized entity and send back to the usage system US and/or server S.

In particular, the distributed consent ledger CLDG comprises consent information CI, CI.j, ..., CI.k, wherein each consent information CI, CI.j, ..., CI.k comprises a consent signature CSGN, CSGN.j, ..., CSGN.l, wherein each consent signature CSGN, CSGN.j, ..., CSGN.l is based on the respective medical data records MDR, MDR.j, ..., MDR.l and/or based on the respective identifier AEID, AEID.j, ..., AEID.k of the authorized entity AE. In particular, the consent signature CSGN, CSGN.j, ..., CSGN.l is signed based on a first identifier PID1 of the patient PAT the respective medical data record MDR, MDR.j, ..., MDR.l. In particular, the first identifier PID1 of the patient comprises a first private key PAT.PRK1, PAT.j.PRK1, ..., PAT.l.PRK1 of the patient PAT. A further step of the second embodiment is then performing a second check CHK-2 whether the consent signature CSGN, CSGN.j, ..., CSGN.l is validly signed based on the first identifier PID1 of the patient PAT, wherein the step of providing PROV-MDR is only executed in the case of a positive second check.

In this embodiment, the consent signature CSGN, CSGN.j, ..., CSGN.l is calculated as $$CSGN.j = SGN(H1(MDR.j) \& AEID.j, PAT.j.PRK1)$$

$$CSGN.k = SGN(H1(MDR.k) \& AEID.k, PAT.k.PRK1)$$

$$CSGN.l = SGN(H1(MDR.l) \& AEID.l, PAT.l.PRK1)$$

The consent signature CSGN, CSGN.j, ..., CSGN.l can then be verified using the signature verification function VRF and the first public key PAT.j.PBK1, ..., PAT.l.PBK1 of the patient PAT.

$$VRF(CSGN.j, H1(MDR.j) \& AEID.j, PAT.j.PBK1)$$

$$VRF(CSGN.k, H1(MDR.k) \& AEID.k, PAT.k.PBK1)$$

$$VRF(CSGN.l, H1(MDR.l) \& AEID.l, PAT.l.PBK1)$$

The result of the signature verification function is either true or false, depending on whether the consent signature CSGN, CSGN.j, ..., CSGN.l is valid. The outcome of the second check is to be considered as positive of the output of the signature verification function is true.

In this embodiment, for calculating the result of the signature verification function, the hash H(MDR), H1(MDR.j), ... H1 (MDR.l) of the medical data record MDR, MDR.j, ..., MDR.l and the identifier AEID, AEID.j, ..., AEID.l of the authorized entity AE must be known. These two quantities can be contained in the consent information CI.j, ..., CI.l, or can be contained in the access request AR. In particular, the identifier AEID, AEID.j, ..., AEID.l of the authorized entity AE can be replaced with the identifier of the requesting entity RE, so that at the same time it can be checked whether the requesting entity RE is an authorized entity AE.

In this embodiment, there is the step of performing a third check CHK-3 with the computation unit US.CU. In particular, the access request AR comprises an intended usage information, and within the performing of the third check CHK-3 a stored usage information UI, UI.j, UI.k, UI.l is determined based on the distributed consent ledger CLDG. In particular, usage information UI.j, UI.k, UI.l is documented in the distributed consent ledger CLDG related to medical data records MDR, MDR.j, MDR.k, MDR.l, in particular by being contained in the same consent information CI, CI.j, CI.k, CI.l as the related medical data record MDR, MDR.j, MDR.k, MDR.l, and the stored usage information UI, UI.j, UI.k, UI.l determined is the usage information UI, UI.j, UI.k, UI.l related to the requested medical data record RMDR. In particular, performing a third check CHK-3 comprises determining whether the intended usage information matches the stored usage information UI, UI.j, UI.k, UI.l. In particular, the intended usage information and the stored usage information UI, UI.j, UI.k, UI.l match, if the intended usage information and the stored usage information UI, UI.j, UI.k, UI.l are equivalent, or if the intended usage information is a subset of the stored usage information UI, UI.j, UI.k, UI.l.

For example, the stored usage information UI, UI.j, UI.k, UI.l can be "train_ai", indicating that consent is given for the respective medical data record MDR, MDR.j, MDR.k, MDR.l being used for training an artificial intelligence algorithm, and the intended usage information can also be "train_ai", so that the stored usage information UI, UI.j, UI.k, UI.l and the intended usage information match. If in contrast the intended usage information is "reference" indicating that the requested medical data record RMDR should be used as a reference case, the intended usage information would not match the stored usage information UI, UI.j, UI.k, UI.l "train_ai", and the result of the third check would be negative. This would also be the case if the intended usage information is "reference/train_ai", indicating that the requested medical data record RMDR should be used both as a reference for training an artificial intelligence algorithm.

In another example, if the stored usage information UI, UI.j, UI.k, UI.l is "train_ai/reference", the intended usage informations "train_ai", "reference", "reference/train ai" and "train_ai/reference" would match the stored usage information UI, UI.j, UI.k, UI.l, and the result of the third check is true.

In the displayed embodiment, there are the steps of performing a first check CHK-1, of performing a second check CHK-2 and of performing a third check CHK-3. Only in the case of all three checks are positive, the requested medical data record RMDR will be provided PROV-MDR to the requesting entity RE and/or the user client UC. If one of the three checks yields a negative result, the step of denying access DNY-ACC will be performed, e.g. by the server and/or the usage system S sending a HTTP response specifying the HTTP status code 400 ("Bad request"), 401 ("Unauthorized"), 403 ("Forbidden"), 404 ("Not Found") or 451 ("Unavailable for Legal Reasons").

Alternatively, it is also possible to perform no check at all. Alternatively, it is also possible to perform only one check, in particular, it is possible to only perform the first check CHK-1, or it is possible to only perform the second check CHK-2, or it is possible to only perform the third check CHK-3. Alternatively, it is also possible to perform only two checks, in particular, it is possible to only perform the first check CHK-1 and to perform the second check CHK-2, or it is possible to only perform the first check CHK-1 and the perform the third check CHK-3, or it is possible to only perform the second check CHK-2 and to perform the third check CHK-3.

In this embodiment, all performed checks have to yield a positive result to provide PROV-MDR the requested medical data record RMDR by the usage system US and/or server S, and if one or more checks yield a negative result, the access will be denied by the usage system US and/or server S. It is also possible to have other prerequisites for providing PROB-MDR the requested medical data record RMDR by the usage system US and/or server S, for example that at least two of three checks yield a positive result, or that one check or a group of other checks yield a positive result.

A further optional step of the displayed embodiment is determining DET-PI2 a second identifier PID2 of the patient PAT being owner of the requested medical data record RMDR based on the distributed ownership ledger OLDG with the computation unit US.CU. In particular, the second identifier PID2 of the patient PAT can comprise a second public key PAT.j.PBK2, . . . , PAT.l.PBK2 of the patient. In particular, the second identifier PID2 of the patient PAT can be determined by searching the distributed ownership ledger OLDG for the hash H(MDR), H2(MDR.j), H2(MDR.k), H2(MDR.l) of the medical data record MDR, MDR.j, MDR.k, MDR.l.

In the displayed embodiment, the second identifier PID2 of the patient PAT is the second public key PAT.PBK2, PAT.j.PBK2, PAT.k.PBK2, PAT.l.PBK2 of an asymmetric key pair, wherein the patient PAT (in particular, only the patient PAT) has access to the corresponding second private key PAT.PRK2, PAT.j.PRK2, . . . , PAT.l.PRK2.

A further optional step of the displayed embodiment is transferring TRF-1 cryptocurrency from a first account to a second account, wherein the first account is related to the identifier of the requesting entity RE, and wherein the second account is related to the second identifier PID2 of the patient PAT. In this embodiment, transferring TRF-1 cryptocurrency from the first account to the second account is executed via a smart contract, wherein the smart contract is documented in the distributed consent ledger CLDG and/or in the distributed ownership ledger OLDG. Alternatively, transferring TRF-1 cryptocurrency from the first account to the second account can comprise documenting a transaction of cryptocurrency from the first account to the second account within a distributed ledger, wherein this distributed ledger can be identical with the distributed consent ledger CLDG and/or in the distributed ownership ledger OLDG, or wherein this distributed ledger can be different from the distributed consent ledger CLDG and the distributed ownership ledger OLDG.

A further step of the displayed embodiment is providing PROV-MDR the requested medical data record RMDR based on the access request AR with the interface US.IF. In particular, the requested medical data record RMDR is provided PROF-MDR based on the access request AR, if the requested medical data record RMDR is the medical data record the access request AR is directed to. In this embodiment, the requested medical data record RMDR is contained in a HTTP response send from . . . to . . . . Alternatively, other formats, standards and/or protocols can be used, e.g. HTTPS, WebDAV, FTP, or other data transfer protocols known to the person skilled in the art.

A further optional step of the displayed embodiment is receiving REC-AI, by a trusted entity TE, an account information ACCI by the patient PAT being owner of the requested medical data record RMDR. In particular, the account information ACCI can be the second private key PAT.PRK2, PAT.j.PRK2, . . . , PAT.l.PRK2 related to the second identifier PID2 of the patient PAT, wherein the second identifier PID is the second public key PAT.PBK2, PAT.j.PBK2, PAT.l.PBK2 corresponding to the second private key PAT.PRK2, PAT.j.PRK2, . . . , PAT.l.PRK2.

Here, the trusted entity TE is an entity enabling to change cryptocurrency into real money (another term for "real money" is "fiat currency", e.g. Dollars or Euros), without exposing the identity of the receiving party to the public. It is possible that the trusted entity TE may expose the identity of the receiving party to a regulatory authority based on legal requirements. In this embodiment, the receiving party is the patient PAT being owner of the requested medical data record RMDR.

A further optional step of the displayed embodiment is transferring TRF-2 cryptocurrency from the second account to a third account based on the account information ACCI, wherein the third account is related to the trusted entity TE. In this embodiment, the cryptocurrency is transferred from the patient PAT being owner of the requested medical data record RMDR to the trusted entity TE, transferring TRF-2 cryptocurrency from the second account to a third account can comprise documenting a transaction of cryptocurrency from the second account to the third account within a distributed ledger. By the account information ACCI being the second private key PAT.PRK2, PAT.j.PRK2, . . . , PAT.l.PRK2 related to the second identifier PID2 comprising the corresponding second public key PAT.PBK2, PAT.j.PBK2, . . . , PAT.l.PBK2, the trusted entity TE can claim the ownership of the cryptocurrency related to the second identifier PID2 or the second account and initiate a transfer of this ownership. In particular, the step of transferring TRF-2 cryptocurrency from the second account to a third account can then comprise initiating a payment from the trusted entity TE to the patient PAT, wherein this payment is issued in a fiat currency.

By this mechanism, the patient PAT is able to extract fiat currency from its second account, by only the trusted entity TE and not the public being able to correlate the second account with its real identity.

Figure 11:
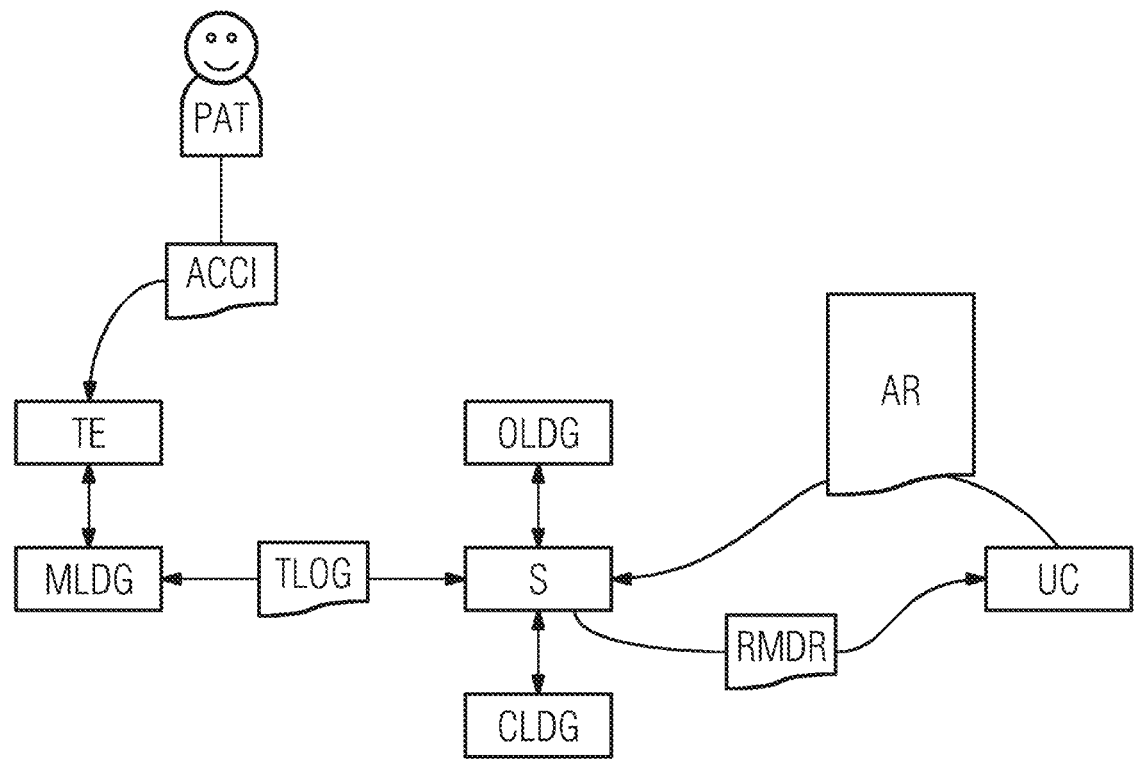

FIG. 11 shows an embodiment of the overall data flow between the user client UC, the server S and a trusted entity TE. The data flow between the user client UC and the server S is identical with the data flow between the user client UC and the server S as displayed and described in FIG. 6 or FIG. 7. In particular, the server S and/or the user client UC can be contained in a usage system US.

Furthermore, in this embodiment the usage system US and/or server S documents a transaction log TLOG within a distributed money ledger MLDG. The transaction log TLOG comprises the transaction of cryptocurrency between a first account and a second account, wherein the first account is an account of the receiving entity RE using the requested medical data record RMDR, and wherein the second account is an account of the patient PAT. In particular, the transaction log comprises the first account, the second account and the amount of cryptocurrency CC.i, CC.j, CC.k being transferred. Alternatively, the transaction of cryptocurrency between the first account and the second account can be regulated via a smart contract. In this case, the smart contract can be stored in the distributed money ledger MLDG or in the distributed consent ledger CLDG.

In particular, the distributed consent ledger CLDG and the distributed money ledger MLDG can be identical; alternatively, the distributed consent ledger CLDG and the distributed money ledger MLDG can be two different distributed ledgers.

Furthermore, in this embodiment the patient PAT provides the trusted entity TE with an account information ACCI, wherein the account information ACCI can be used to claim the cryptocurrencies associated with the second account. In particular, in this embodiment the account information ACCI are a private key corresponding to the public key being the address of the second account. The trusted entity TE can then use the account information ACCI to transfer cryptocurrency from the second account to a third account, the third account being associated with the trusted entity TE. In particular, the transfer of cryptocurrency from the second account to the third account is executed by documenting the transfer of cryptocurrency in the distributed money ledger MLDG.

Figure 12:
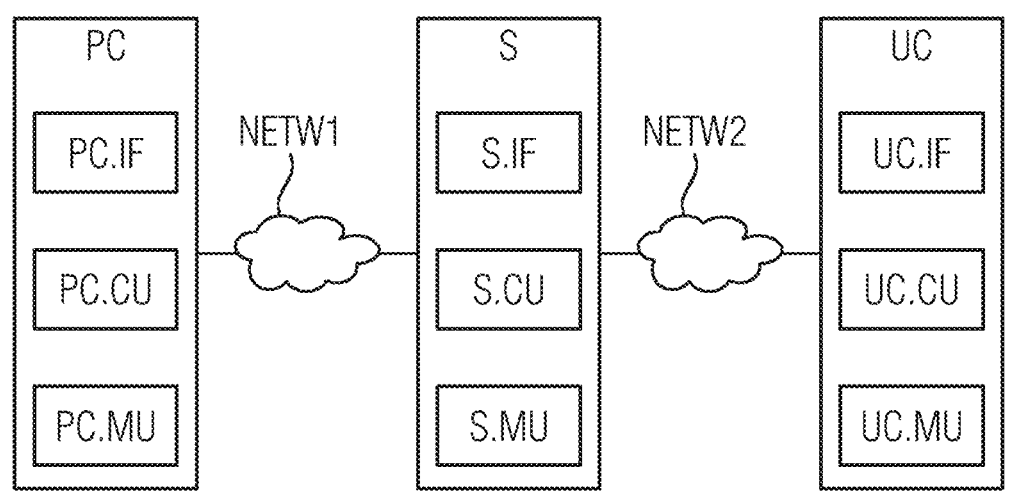

FIG. 12 displays a patient client PC, a server S and a user client UC. The patient client PC, the server S and/or the user client UC can be a (personal) computer, a workstation, a virtual machine running on host hardware, a microcontroller, or an integrated circuit. In particular, the patient client PC, the server S and/or the user client UC can be mobile devices, e.g. a smartphone, a tablet or a device implanted into a patient PAT. As an alternative, the patient client PC, the server S and/or the user client UC can be a real or a virtual group of computers (the technical term for a real group of computers is "cluster", the technical term for a virtual group of computers is "cloud"). In particular the patient client PC, the server S and/or the user client UC can be integrated into a common device.

In the displayed embodiments, the user client UC comprises an interface UC.IF, a computation unit UC.CU and a memory unit UC.MU, the server S comprises an interface S.IF, a computation unit S.CU and a memory unit S.MU, and/or the patient client PC comprises an interface PC.IF, a computation unit PC.CU and a memory unit PC.MU.

The patient client PC and the server S are connected by a first network NETW1, and the server S and the user client UC are connected by a second network NETW2. The first network NETW1 and the second network NETW2 can be identical; alternatively the first network NETW1 and the second network NET2 may be different. Furthermore, the connection between the patient client PC and the server S by the first network NETW1 is optional, and the connection between the user client UC and the server S by the first network NETW2 is optional. It is also possible that the patient client PC and the user client UC are connected by the first network NET1, the second network NET2 and/or another network.

An interface PC.IF, S.IF, UC.IF can be embodied as a hardware interface or as a software interface (e.g. PCIBus, USB or Firewire). In general, a calculation unit PC.CU, S.CU, UC.CU can comprise hardware elements and software elements, for example a microprocessor, a CPU (acronym for "central processing unit"), a GPU (acronym for "graphical processing unit"), a field programmable gate array (an acronym is "FPGA") or an ASIC. (acronym for "application-specific integrated circuit"). The calculation unit PC.CU, S.CU, UC.CU, SERV.CU can be configured for multithreading, i.e. the calculation unit PC.CU, S.CU, UC.CU can host different calculation processes at the same time, executing the either in parallel or switching between active and passive calculation processes. A memory unit PC.MU, S.MU, UC.MU can be e.g. non-permanent main memory (e.g. random access memory) or permanent mass storage (e.g. hard disk, USB stick, SD card, solid state disk).

The first network NETW1 and/or the second network NETW2 can be realized as a LAN (acronym for "local area network"), in particular a WiFi network, or any other local connection, e.g. via Bluetooth or USB (acronym for "universal serial bus"). The network NET can alternatively also be realized as a VPN (acronym for "virtual private network").

Figure 13:
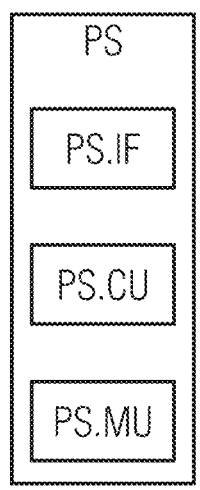
Figure 14:
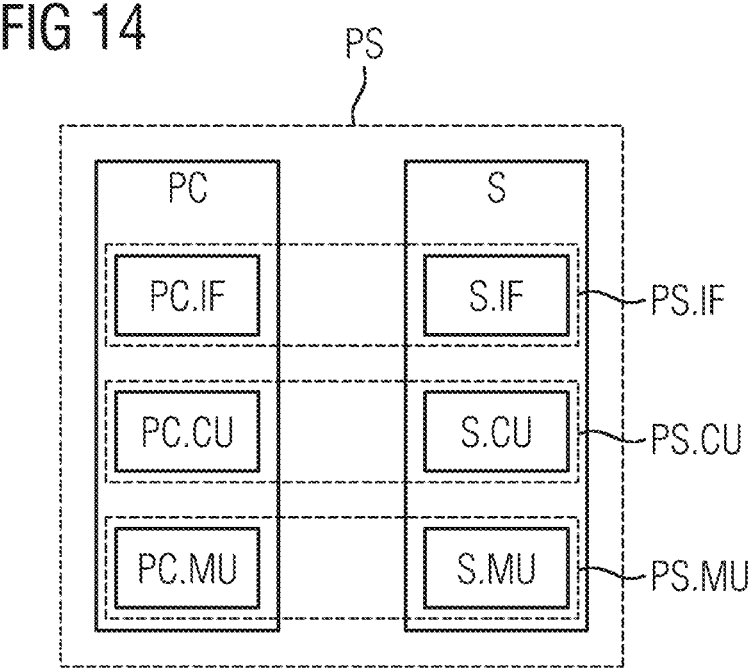
Figure 15:
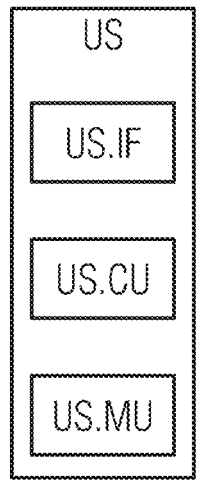
Figure 16:
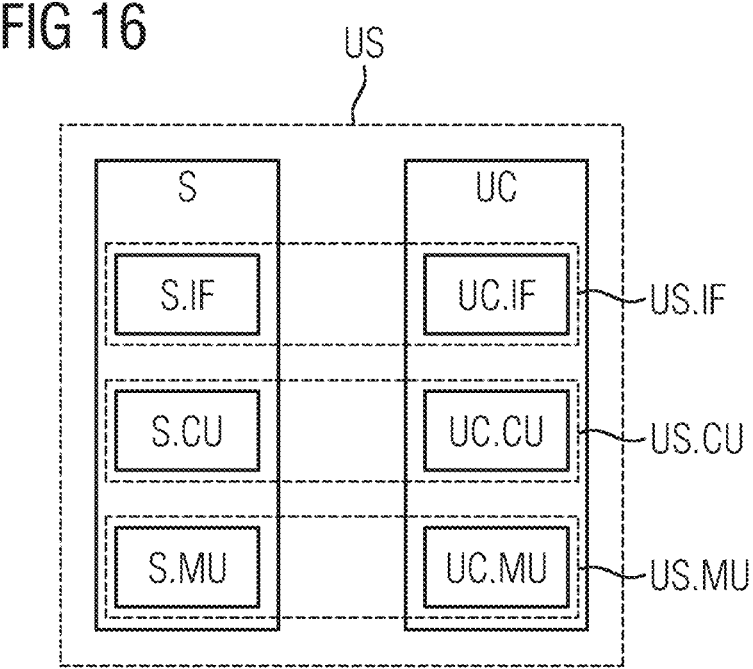

FIG. 13 shows a first embodiment of a providing system PS, FIG. 14 shows a second embodiment of a providing system PS. FIG. 15 shows a first embodiment of a usage system US, and FIG. 16 shows a second embodiment of a usage system US. The providing system PS and/or the usage system US can be a (personal) computer, a workstation, a virtual machine running on host hardware, a microcontroller, or an integrated circuit. In particular, the providing system PS and/or the usage system US, e.g. a smartphone, a tablet or a device implanted into a patient PAT. As an alternative, the providing system PS and/or the usage system US can be a real or a virtual group of computers (the technical term for a real group of computers is "cluster", the technical term for a virtual group of computers is "cloud").

The providing system PS comprises an interface PS.IF, a computation unit PS.CU and a memory unit PS.MU, and/or the usage system US comprises an interface US.IF, a computation unit US.CU and a memory unit US.MU. The interfaces PS.IF, US.IF, the computation units PS.CU, US.CU and the memory units PS.MU, US.MU can have the same advantageous embodiments as described with respect to FIG. 12.

Within the first embodiment of the providing system PS displayed in FIG. 13, the interface PS.IF, the computation unit PS.CU and the memory unit PS.MU are stand-alone units. Within the second embodiment of the providing system PS displayed in FIG. 14, the providing system PS comprises a patient client PC and/or a server S, the interface PS.IF of the providing system PS comprises the interface PC.IF of the patient client PC and/or the interface S.IF of the server S, the computation unit PS.CU of the providing system PS comprises the computation unit PC.CU of the patient client PC and/or the computation unit S.CU of the server S, and the memory unit PS.MU of the providing system PS comprises the memory unit PC.MU of the patient client PC and/or the memory unit S.MU of the server S.

Within the first embodiment of the usage system US displayed in FIG. 13, the interface US.IF, the computation unit US.CU and the memory unit US.MU are stand-alone units. Within the second embodiment of the usage system US displayed in FIG. 14, the usage system US comprises a user client UC and/or a server S, the interface US.IF of the usage system US comprises the interface UC.IF of the user client UC and/or the interface S.IF of the server S, the computation unit US.CU of the usage system US comprises the computation unit UC.CU of the usage client UC and/or the computation unit S.CU of the server S, and the memory unit US.MU of the usage system US comprises the memory unit UC.MU of the usage client UC and/or the memory unit S.MU of the server S.

Figure 17:
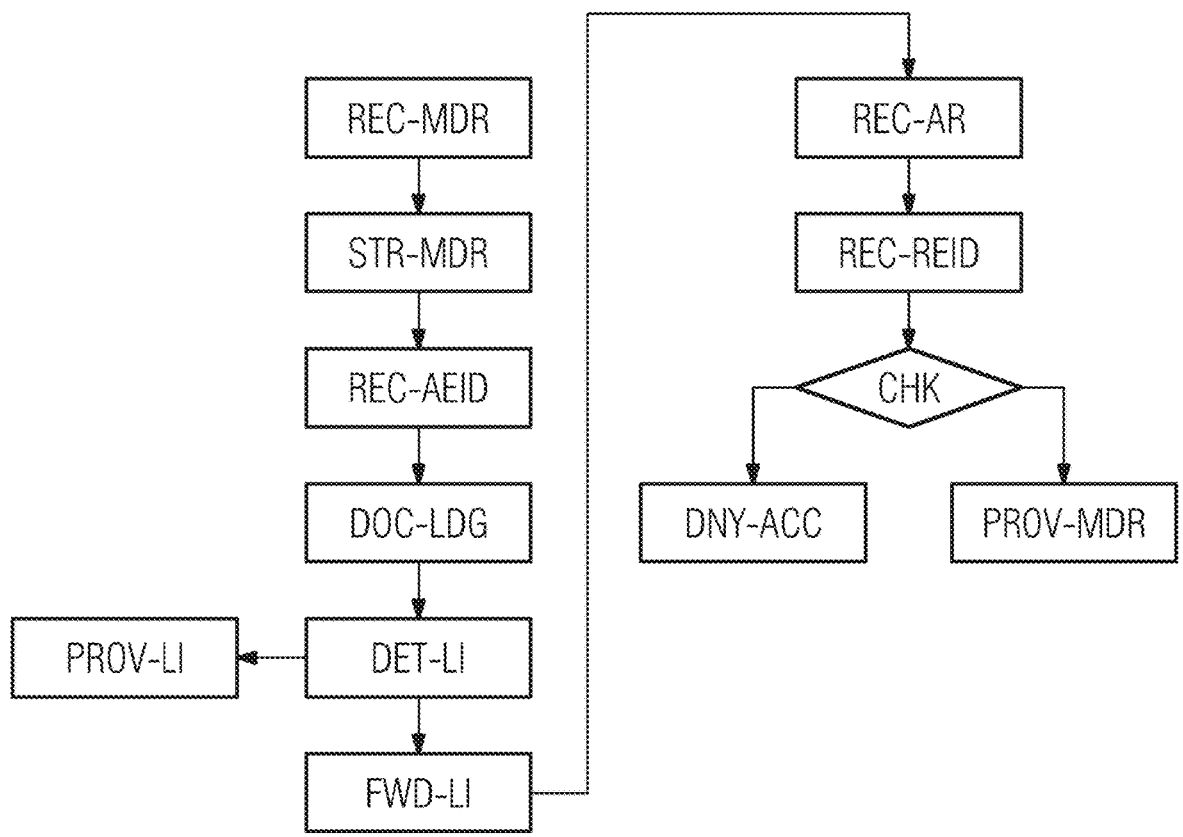

FIG. 17 displays a flowchart an embodiment of the method for providing a location information and an embodiment for the method for using a location information. The flowcharts of the two embodiments are executed subsequently in the displayed flowchart, but it is to be understood that the two embodiments of the methods can also be executed independently of each other. Both embodiments can be executed on a server S and/or a providing system PS and/or a usage system US. The repository can be identified with a memory unit S.MU of the server S and/or with a memory unit PS.MU of the providing system PS and/or with a memory unit US.MU of the usage system US, or can be contained in the respective memory unit US.MU, PS.MU, S.MU.

The first step of the displayed embodiment of the method for providing a location information is receiving REC-MDR the medical data record MDR, MDR.j, MDR.k, MDR.l with an interface PS.IF, wherein the medical data record MDR, MDR.j, MDR.k, MDR.l is related to a patient PAT. The next step is storing STR-MDR the medical data record MDR, MDR.j, MDR.k, MDR.l within a repository with a computation unit US.CU. In particular, the medical data record MDR, MDR.j, MDR.k, MDR.l is stored within the file system of the repository, for example at the file location "data/ct/mdr_1.dat". Furthermore, the providing system PS and/or server S can be accessed in this embodiment by an uniform resource locator URL (resolving to an IP address via a DNS server), for example "http://cloud-storage.com".

The next step of the displayed embodiment of the method for providing a location information is receiving REC-AEID an identifier AEID, AEID.j, AEID.k, AEID.l of an authorized entity AE with the interface PS.IF, wherein the authorized entity AE is allowed to access the medical data record MDR, MDR.j, MDR.k, MDR.l stored within the repository, and wherein the location information is based on the identifier AEID, AEID.j, AEID.k, AEID.l of the authorized entity AE.

In this embodiment, the identifier AEID, AEID.j, AEID.k, AEID.l of the authorized entity AE is a string that can be contained within the location information, and which is additionally stored in the repository related to the medical data record MDR, MDR.j, MDR.k, MDR.l, for example in a list comprising all medical data records MDR, MDR.j, MDR.k, MDR.l stored in the repository and sets of identifiers AEID, AEID.j, AEID.k, AEID.l of authorized entities AE allowed to access the respective medical data record MDR, MDR.j, MDR.k, MDR.l.

In particular, the identifier AEID, AEID.j, AEID.k, AEID.l of the authorized entity AE can be a random number or a random string, as well as a public key related to the authorized entity AE, or data signed with a private key related to the authorized entity AE.

A further step of the displayed embodiment for providing a location information is documenting DOC-LDG the medical data record MDR, MDR.j, MDR.k, MDR.l and the identifier AEID, AEID.j, AEID.k, AEID.l of the authorized entity AE in a distributed ledger CLDG with the computation unit PS.CU. In particular, the distributed ledger CLDG can be a distributed consensus ledger CLDG.

In this embodiment, the medical data record MDR, MDR.j, MDR.k, MDR.l and the identifier AEID, AEID.j, AEID.k, AEID.l of the authorized entity AE is documented in the distributed consensus ledger by storing a signature based on a hash of a combination of the medical data record MDR, MDR.j, MDR.k, MDR.l and the identifier AEID, AEID.j, AEID.k, AEID.l of the authorized entity AE in the distributed consensus ledger, wherein the signature is signed with a private key PAT.PRK1, PAT.j.PRK1, PAT.k.PRK1, PAT.l.PRK1 related to the patient PAT.

A further step of the displayed embodiment for providing a location information is determining DET-LI the location information related to the medical data record MDR, MDR.j, MDR.k, MDR.l stored within the repository with the computation unit US.CU, wherein the medical dataset can be accessed based on the location information. In this embodiment, the location information is a combination of the address of the repository, of the location of the medical data record MDR, MDR.j, MDR.k, MDR.l within the repository, and the identifier AEID, AEID.j, AEID.k, AEID.l of the authorized entity AE. In particular, the location information is a uniform resource locator URL, e.g. given by "http://cloud-storage.com/data/ct/mdr_1.dat& auth=7597655124", wherein "7597655124" is the identifier AEID, AEID.j, AEID.k, AEID.l of the authorized entity AE.

The next step of the displayed embodiment for providing a location information are providing PROV-LI the location information with the interface PS.IF to the patient PAT and sending FWD-LI the location information to the authorized entity AE with the interface PS.IF. In both steps, location information may include the identifier AEID, AEID.j, AEID.k, AEID.l of the authorized entity AE, or the location identifier AEID, AEID.j, AEID.k, AEID.l may not include the identifier AEID, AEID.j, AEID.k, AEID.l of the authorized entity AE. In the latter case, the location information provided to the patient PAT or to the authorized entity AE would be "http://cloud-storage.com/data/ct/mdr_1.dat"

A first step of the displayed embodiment for using a location information displayed in the flowchart is receiving REC-AR an access request AR to the medical data record MDR, MDR.j, MDR.k, MDR.l by the repository or by the interface US.IF of the usage system US, in particular, by the interface S.IF of the server S, wherein the medical data record MDR, MDR.j, MDR.k, MDR.l is stored within the repository, and wherein the access request AR is based on the location information. In particular, the access request AR comprises the location information, wherein the location information comprises the location of the medical data record MDR, MDR.j, MDR.k, MDR.l within the repository. In this embodiment, the access request AR is initiated by a requesting entity RE, wherein the requesting entity RE can be equal to the authorized entity AE, or wherein the requesting entity RE can be unequal to the authorized entity AE.

A further step of the embodiment for using a location information is receiving REC-REID an identifier REID of the requesting entity RE with the interface US.IF, and performing a check CHK whether a pair comprising the medical data record MDR, MDR.j, MDR.k, MDR.l and the identifier of the requesting entity RE are documented in the distributed ledger CLDG with the computation unit US.CU.

In this embodiment, the access request AR comprises the identifier REID of the requesting entity RE, for example as "http://cloud-storage.com/data/ct/mdr_1.dat& auth=7597655124", wherein "7597655124" is the identifier REID of the requesting entity RE and at the same time the identifier AEID, AEID.j, AEID.k, AEID.l of the authorized entity AE, which is documented in the distributed ledger CLDG. So the outcome of the check is positive. If the identifier REID of the requesting entity RE does not math an identifier AEID, AEID.j, AEID.k, AEID.l of the authorized entity AE documented related to the medical data record MDR, MDR.j, MDR.k, MDR.l in the distributed ledger CLDG, the outcome of the check would be negative.

In case of a positive check, a further step of the embodiment for using a location information is providing PROV-MDR the medical data record MDR, MDR.j, MDR.k, MDR.l with the repository, in particular sending the medical data record MDR, MDR.j, MDR.k, MDR.l to a user client UC. In case of a negative check, a further step of the embodiment for using a location information is denying DNY-ACC the access to the medical data record MDR, MDR.j, MDR.k, MDR.l.

Figure 18:
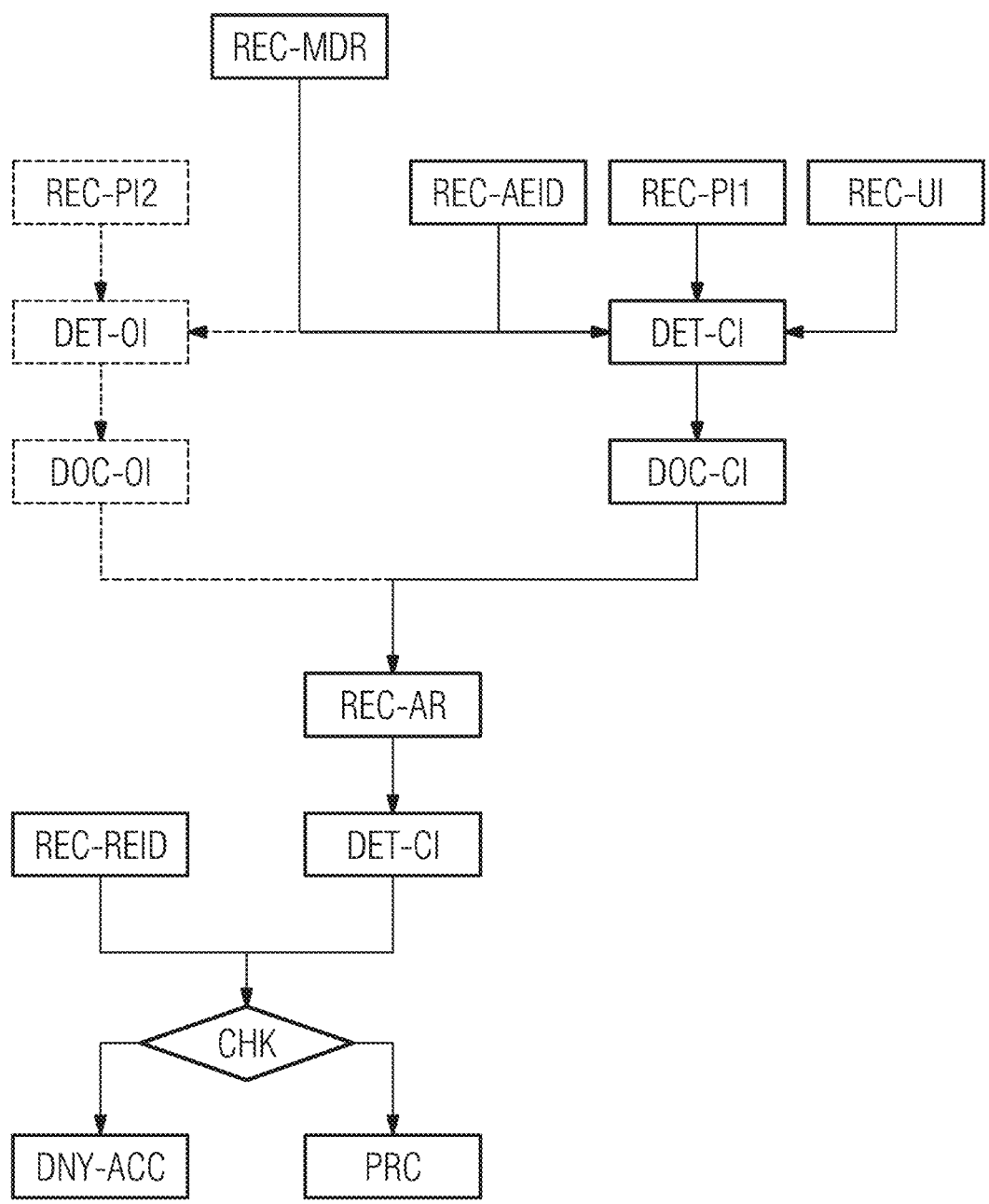

FIG. 18 displays an embodiment of a method for storing consent in a distributed consent ledger CLDG, and an embodiment of a method for using consent information CI, CI.j, CI.k, CI.l stored in a distributed consent ledger CLDG. In particular, consent is stored in terms of consent information CI, CI.j, CI.k, CI.l.

The displayed embodiment of the method for storing consent comprises the step of receiving REC-MDR a medical data record MDR, MDR.j, MDR.k, MDR.l with an interface PS.IF, wherein the medical data record MDR, MDR.j, MDR.k, MDR.l is related to a patient PAT.

The displayed embodiment of the method for storing consent furthermore comprises the step of receiving REC-AEID an identifier AEID, AEID.j, AEID.k, AEID.l of an authorized entity AE with the interface PS.IF, the step of receiving REC-PI1 a first identifier PID1 of the patient PAT with the interface PS.IF, and the step of receiving REC-UI usage information UI, UI.j, UI.k, UI.l with the interface PS.IF.

The displayed embodiment of the method for storing consent furthermore comprises the step of determining DET-CI consent information CI, CI.j, CI.k, CI.l with a computation unit PS.CU, wherein the consent information CI, CI.j, CI.k, CI.l is based on the medical data record MDR, MDR.j, MDR.k, MDR.l and the identifier AEID, AEID.j, AEID.k, AEID.l of the authorized entity AE. In particular, the consent information CI, CI.j, CI.k, CI.l is furthermore based on the first identifier PID1 of the patient PAT. In particular, the consent information CI, CI.j, CI.k, CI.l is furthermore based on the usage information UI, UI.j, UI.k, UI.l.

In the displayed embodiment of the method for storing consent, the consent information CI, CI.j, CI.k, CI.l comprises a consent signature CSGN, CSGN.j, CSGN.k, CSGN.l based on the medical data record MDR, MDR.j, MDR.k, MDR.l and based on the identifier AEID, AEID.j, AEID.k, AEID.l of the authorized entity AE, wherein the consent signature CSGN, CSGN.j, CSGN.k, CSGN.l is signed with the first identifier PID1 of the patient PAT.

The displayed embodiment of the method for storing consent furthermore comprises the step of documenting DOC-CI the consent information CI, CI.j, CI.k, CI.l in a distributed consent ledger CLDG with the computation unit PS.CU.

Within the displayed embodiment, the method for storing consent information CI, CI.j, CI.k, CI.l furthermore comprises the optional steps of receiving REC-PI2 a second identifier PID2 of the patient PAT with the interface PS.IF, determining DET-OI ownership information OI, OI.j, OI.k, OI.l with the computation unit PS.CU, wherein the ownership OI.j, OI.k, OI.l information comprises an ownership signature OSGN, OSGN.j, OSGN.k, OSGN.l based on the medical data record MDR, MDR.j, MDR.k, MDR.l, wherein the ownership signature OSGN, OSGN.j, OSGN.k, OSGN.l is signed with the second identifier PID2 of the patient PAT, and documenting DOC-OI the ownership information OI, OI.j, OI.k, OI.l in a distributed ownership ledger OLDG with the computation unit PS.CU. In particular, the second identifier PID2 of the patient PAT can comprise a second public key PAT.PBK2, PAT.j.PBK2, . . . , PAT.l.PBK2 of the patient.

In particular, in this embodiment of the method for storing consent, the consent information CI, CI.j, CI.k, CI.l comprises a smart contract, wherein the smart contracts regulates a transfer of cryptocurrency in the event of using the medical data record MDR, MDR.j, MDR.k, MDR.l, wherein the cryptocurrency is transfer from a first account to a second account, wherein the first account is related to an entity using the medical data record MDR, MDR.j, MDR.k, MDR.l, and wherein the second account is related to the first identifier PID1 of the patient PAT and/or to the second identifier PID2 of the patient PAT.

The steps of the embodiment of the method for storing consent information CI, CI.j, CI.k, CI.l described until now can additionally comprise all advantageous features and embodiments described before, in particular the advantageous features and embodiments described to the same steps of FIG. 1, FIG. 2 and FIG. 5.

The displayed embodiment of the method for using consent information CI, CI.j, CI.k, CI.l stored in a distributed consent ledger CLDG comprises the step of receiving REC-AR an access request AR directed to a requested medical data record RMDR by an interface US.IF, wherein the requested medical data record RMDR is stored within a memory unit US.MU, and wherein the requested medical data record RMDR is related to a patient PAT. In particular, the access request AR is initiated by a requesting entity RE.

The displayed embodiment of the method for using consent information CI, CI.j, CI.k, CI.l stored in a distributed consent ledger CLDG furthermore comprises the step of locating DET-CI consent information CI, CI.j, CI.k, CI.l in the distributed consent ledger CLDG with a computation unit PS.CU, wherein the consent information CI, CI.j, CI.k, CI.l is related to the requested medical data record RMDR.

The displayed embodiment of the method for using consent information CI, CI.j, CI.k, CI.l stored in a distributed consent ledger CLDG furthermore comprises the step of receiving REC-REID an identifier REID of the requesting entity RE with the interface US.IF.

The displayed embodiment of the method for using consent information CI, CI.j, CI.k, CI.l stored in a distributed consent ledger CLDG furthermore comprises the step of performing a check CHK based on the consent information CI, CI.j, CI.k, CI.l whether the patient PAT consented to use the requested medical data record RMDR with the computation unit US.CU. In this embodiment, the check is furthermore based on a comparison of the identifier REID of the requesting entity RE and the identifier AEID, AEID.j, AEID.k, AEID.l of the authorized entity AE.

In case of a positive check, the displayed embodiment of the method for using consent information CI, CI.j, CI.k, CI.l stored in a distributed consent ledger CLDG furthermore comprises the step of processing PRC the requested medical data record RMDR with the computation unit US.CU. In this embodiment the consent information CI, CI.j, CI.k, CI.l comprises a smart contract, and wherein processing PRC the requested medical data record RMDR comprises executing the smart contract.

In the displayed embodiment, the access request AR comprises a trainable function, wherein processing PRC the requested medical data record RMDR comprises training the trainable function based on the requested medical data record RMDR, and optionally providing the trainable function after training the trainable function based on the requested medical data record RMDR. Alternatively, processing PRC the requested medical data record RMDR can comprise displaying the requested medical data record RMDR in a non-copyable way.

In this embodiment, the trainable function is an artificial neural network comprising edge weights, wherein the edge weights are adjusted by way of training. In particular, for the training and the adjusting of the edge weights, the requested medical data record RMDR is used as an input for the neural network. In this embodiment, the requested medical data record RMDR comprises imaging data and annotations of the imaging data, for example a segmentation of the imaging data, or a diagnostic information relating to the imaging data. In particular, the imaging data is used as an input for the neural network, and the output of the neural network is a calculated annotation of the imaging data, which can be compared with the actual annotation of the imaging data contained in the requested medical data record RMDR. Based on a comparison of the output of the artificial neural network and the actual annotation of the imaging data contained in the requested medical data record RMDR, the parameters of the trainable function, which are the edge weights of the artificial neural networks, can be adjusted in particular by minimizing the distance between the output of the artificial neural network and the actual annotation of the imaging data contained in the requested medical data record RMDR, for example based on a backpropagation algorithm.

In order to display the requested medical data record RMDR in a non-copyable way, the requested medical data record RMDR can be provided to the user client UC in a web browser, and copying the requested medical data record RMDR can be hampered by not allowing a right-click on the requested medical data record RMDR using Javascript. Furthermore, if the requested medical data record RMDR comprises text information, the text information can be rendered as an image, and only the image can be provided to the user client UC. Furthermore, it might be possible to install a specialized application on the user client UC, which does not allow to copy the data displayed within, and to use this specialized application for displaying the requested medical data record RMDR. In particular, the requested medical data record RMDR can be encrypted and/or encoded so that only the specialized application is able to decrypt and/or decode the requested medical data record RMDR.

Additionally, the displayed embodiment can also comprise the step of determining DET-PI2 an second identifier PID2 of the patient PAT being owner of the requested medical data record RMDR based on the distributed ownership ledger OLDG with the computation unit US.PU, and the step of transferring TRF-1 cryptocurrency from a first account to a second account with the computation unit US.CU, wherein the first account is related to the identifier REID of the requesting entity RE, and wherein the second account is related to the second identifier PID2 of the patient PAT. These steps can comprise all advantageous features and embodiments described with respect to the corresponding steps of FIG. 10. In particular, the second identifier PID2 of the patient can comprise a second public key PAT.PBK2, PAT.j.PBK2, ..., PAT.l.PBK2 of the patient.

Additionally, the displayed embodiment can also comprise the step pf receiving REC-AI, by a trusted entity TE, an account information ACCI by the patient PAT being owner of the requested medical data record RMDR, the step of transferring TRF-2 cryptocurrency from the second account to a third account based on the account information ACCI, wherein the third account is related to the trusted entity TE, and the step of initiating a payment from the trusted entity TE to the patient PAT. These steps can comprise all advantageous features and embodiments described with respect to the corresponding steps of FIG. 10.

The properties, features and advantages of this invention, its aspects and embodiments described above, as well as the manner they are achieved, become clearer and more understandable in the light of the following list of possible embodiments. The following list of embodiments does not limit the invention to the listed embodiments. In particular, features of the described embodiments can always be combined or exchanged with one another without limiting or widening the scope of the described invention, whenever such a combination or exchange is meaningful and in the sense of this invention.

Embodiment 1: A method for providing a location information URL related to a medical data record MDR, MDR.j, MDR.k, MDR.l, comprising:
  receiving REC-MDR the medical data record MDR, MDR.j, MDR.k, MDR.l with an interface PS.IF, wherein the medical data record MDR, MDR.j, MDR.k, MDR.l is related to a patient PAT,
  storing STR-MDR the medical data record MDR, MDR.j, MDR.k, MDR.l within memory unit PS.MU with a computation unit PS.CU,
  determining DET-LI the location information URL related to the medical data record MDR, MDR.j, MDR.k, MDR.l stored within the memory unit PS.MU with the computation unit PS.CU, wherein the medical dataset MDR, MDR.j, MDR.k, MDR.l can be accessed based on the location information URL,
  providing PROV-LI the location information URL with the interface PS.IF to the patient PAT.

Embodiment 2: The method according to embodiment 1, furthermore comprising:
  receiving REC-AEID an identifier AEID, AEID.j, AEID.k, AEID.l of an authorized entity AE with the interface PS.IF, wherein the authorized entity AE is allowed to access the medical data record MDR, MDR.j, MDR.k, MDR.l stored within the memory unit PS.MU, and wherein the location information URL is based on the identifier AEID, AEID.j, AEID.k, AEID.l of the authorized entity AE.

Embodiment 3: The method according to embodiment 2, furthermore comprising:
  documenting DOC-LDG the medical data record MDR, MDR.j, MDR.k, MDR.l and the identifier AEID, AEID.j, AEID.k, AEID.l of the authorized entity AE in a distributed ledger CLDG with the computation unit PS.CU.

Embodiment 4: The method according to embodiment 3, wherein the step of documenting DOC-LDG comprises creating a signature based on the medical data record MDR, MDR.j, MDR.k, MDR.l and/or on the identifier AEID, AEID.j, AEID.k, AEID.l of the authorized entity AE, wherein the signature is signed with a private key PAT.PRK1, PAT.j.PRK1, PAT.k.PRK1, PAT.l.PRK1 related to the patient PAT.

Embodiment 5: The method according to one of the embodiments 2 to 4, furthermore comprising:
   sending FWD-LI the location information URL to the authorized entity AE with the interface PS.IF.

Embodiment 6: A method for using a location information URL provided by a method according to one of the embodiments 1 to 5, comprising:
   receiving REC-AR an access request AR to a requested medical data record RMDR by an interface US.IF, wherein the requested medical data record RMDR is stored within a memory unit US.MU, wherein the access request AR is based on the location information URL,
   providing PROV-MDR the requested medical data record RMDR with the interface US.IF.

Embodiment 7: The method according to embodiment 6, wherein the access request AR is initiated by a requesting entity RE, wherein medical data records MDR, MDR.j, MDR.k, MDR.l and identifiers AEID.j, AEID.k, AEID.l of related authorized entities AE are documented in a distributed ledger CLDG, the method furthermore comprising:
   receiving REC-REID an identifier REID of the requesting entity RE with the interface US.IF,
   performing a check CHK whether a pair comprising the requested medical data record RMDR and the identifier REID of the requesting entity RE are documented in the distributed ledger CLDG with a computation unit US.CU, wherein the step of providing PROV-MDR is only executed in case of a positive check.

Embodiment 8: A providing system PS for providing a location information URL related to a medical data record MDR, MDR.j, MDR.k, MDR.l, comprising:
   an interface PS.IF, configured for receiving REC-MDR the medical data record MDR, MDR.j, MDR.k, MDR.l, wherein the medical data record MDR, MDR.j, MDR.k, MDR.l is related to a patient PAT, furthermore configured for providing PROV-LI the location information URL to the patient PAT,
   a computation unit PS.CU, configured for storing STR-MDR the medical data record MDR, MDR.j, MDR.k, MDR.l within a memory unit PS.MU, furthermore configured for determining DET-LI the location information URL related to the medical data record MDR, MDR.j, MDR.k, MDR.l stored within the memory unit PS.MU, wherein the medical dataset MDR, MDR.j, MDR.k, MDR.l can be accessed based on the location information URL.

Embodiment 9: A computer program product comprising program elements which induce a providing system PS to carry out the steps of the method for providing a location information URL according to one of the embodiments 1 to 5, when the program elements are loaded into a memory unit PS.MU of the providing system PS.

Embodiment 10: A computer-readable medium, on which program code sections of a computer program are saved, the program code sections being loadable into and/or executable in a providing system PS to make the providing system PS execute the method for providing a location information URL according to one of the embodiments 1 to 5, when the program code sections are executed in the providing system PS.

Embodiment 11: A usage system US, configured for receiving REC-AR an access request AR to a requested medical data record RMDR, wherein the requested medical data record RMDR is stored within the usage system US, wherein the access request AR is based on a location information URL provided by a method according to one of the embodiments 1 to 5, furthermore configured for providing PROV-MDR the requested medical data record RMDR.

Embodiment 12: A computer program product comprising program elements which induce a usage system US to carry out the steps of the method for using a location information URL according to embodiment 6 or 7, when the program elements are loaded into a memory unit US.MU of the usage system US.

Embodiment 13: A computer-readable medium, on which program code sections of a computer program are saved, the program code sections being loadable into and/or executable in a usage system US to make the usage system US execute the method for using a location information URL according to embodiment 6 or 7, when the program code sections are executed in the usage system US.

Embodiment 14: A method for storing consent, comprising the following steps:
   receiving REC-MDR a medical data record MDR, MDR.j, MDR.k, MDR.l with an interface PS.IF, wherein the medical data record MDR, MDR.j, MDR.k, MDR.l is related to a patient PAT,
   receiving REC-AEID an identifier AEID, AEID.j, AEID.k, AEID.l of an authorized entity AE with the interface PS.IF,
   determining DET-CI consent information CI, CI.j, CI.k, CI.l with a computation unit PS.CU, wherein the consent information CI, CI.j, CI.k, CI.l is based on the medical data record MDR, MDR.j, MDR.k, MDR.l and the identifier AEID, AEID.j, AEID.k, AEID.l of the authorized entity AE,
   documenting DOC-CI the consent information CI, CI.j, CI.k, CI.l in a distributed consent ledger CLDG with the computation unit PS.CU.

Embodiment 15: The method according to embodiment 14, furthermore comprising:
   receiving REC-PI1 a first identifier PID1 of the patient PAT with the interface PS.IF, wherein the consent information CI, CI.j, CI.k, CI.l is furthermore based on the first identifier PID1 of the patient PAT.

Embodiment 16: The method according to claim 15, wherein the consent information CI, CI.j, CI.k, CI.l comprises a consent signature CSGN, CSGN.j, CSGN.k, CSGN.l based on the medical data record MDR, MDR.j, MDR.k, MDR.l and based on the identifier AEID, AEID.j, AEID.k, AEID.l of the authorized entity AE, wherein the consent signature CSGN, CSGN.j, CSGN.k, CSGN.l is signed with the first identifier PID1 of the patient PAT.

Embodiment 17: The method according to one of the embodiments 14 to 16, furthermore comprising:
   receiving REC-PI2 a second identifier PID2 of the patient PAT with the interface PS.IF,
   determining DET-OI ownership information OI, OI.j, OI.k, OI.l with the computation unit PS.CU, wherein the ownership OI.j, OI.k, OI.l information comprises an ownership signature OSGN, OSGN.j, OSGN.k, OSGN.l based on the medical data record MDR, MDR.j, MDR.k, MDR.l, wherein the ownership signature OSGN, OSGN.j, OSGN.k, OSGN.l is signed with the second identifier PID2 of the patient PAT,
   documenting DOC-OI the ownership information OI, OI.j, OI.k, OI.l in a distributed ownership ledger OLDG with the computation unit PS.CU.

Embodiment 18: The method according to one of the embodiments 14 to 17, furthermore comprising:
- receiving REC-UI usage information UI, UI.j, UI.k, UI.l with the interface PS.IF, > wherein the consent information CI, CI.j, CI.k, CI.l is furthermore based on the usage information UI, UI.j, UI.k, UI.l.

Embodiment 19: The method according to one of the embodiments 14 to 18, wherein the consent information CI, CI.j, CI.k, CI.l comprises a smart contract.

Embodiment 20: The method according to embodiment 19, wherein the smart contracts regulates a transfer of cryptocurrency in the event of using the medical data record MDR, MDR.j, MDR.k, MDR.l, wherein the cryptocurrency is transfer from a first account to a second account, wherein the first account is related to an entity using the medical data record MDR, MDR.j, MDR.k, MDR.l, and wherein the second account is related to the first identifier PID1 of the patient PAT and/or to the second identifier PID2 of the patient PAT.

Embodiment 21: A method for using consent information CI, CI.j, CI.k, CI.l stored in a distributed consent ledger CLDG according to the method according to one of the embodiments 14 to 20, comprising:
- receiving REC-UR an access request AR directed to a requested medical data record RMDR by an interface US.IF, wherein the requested medical data record RMDR is stored within memory unit US.MU, and wherein the requested medical data record RMDR is related to a patient PAT,
- locating DET-CI consent information CI, CI.j, CI.k, CI.l in the distributed consent ledger CLDG with a computation unit PS.CU, wherein the consent information CI, CI.j, CI.k, CI.l is related to the requested medical data record RMDR,
- performing a check CHK based on the consent information CI, CI.j, CI.k, CI.l whether the patient PAT consented to use the requested medical data record RMDR with the computation unit US.CU,
- in case of a positive check, processing PRC the requested medical data record RMDR with the computation unit US.CU.

Embodiment 22: The method according to embodiment 21, wherein the access request AR is initiated by a requesting entity RE, the method furthermore comprising:
- receiving REC-REID an identifier REID of the requesting entity RE with the interface US.IF; wherein the consent information CI, CI.j, CI.k, CI.l comprises an identifier AEID.j, AEID.k, AEID.l of an authorized entity AE, wherein the check is furthermore based on a comparison of the identifier REID of the requesting entity RE and the identifier AEID, AEID.j, AEID.k, AEID.l of the authorized entity AE.

Embodiment 23: The method according to embodiment 21 or 22, wherein the consent information CI, CI.j, CI.k, CI.l comprises a smart contract, and wherein processing PRC the requested medical data record RMDR comprises executing the smart contract.

Embodiment 24: The method according to one of the embodiments 21 to 23, wherein the access request AR comprises a trainable function, wherein processing PRC the requested medical data record RMDR comprises training the trainable function based on the requested medical data record RMDR, and optionally providing the trainable function after training the trainable function based on the requested medical data record RMDR.

Embodiment 25: The method according to one of the embodiments 21 to 24, wherein processing PRC the requested medical data record RMDR comprises displaying the requested medical data record RMDR in a non-copyable way.

Embodiment 26: The method according to one of the claims 21 to 25, wherein ownership information OI, OI.j, OI.k, OI.l are documented in a distributed ownership ledger OLDG, wherein each ownership information OI, OI.j, OI.k, OI.l comprises a ownership signatures OSGN, OSGN.j, OSGN.k, OSGN.l based on medical data records MDR, MDR.j, MDR.k, MDR.l, wherein the ownership signature OSGN, OSGN.j, OSGN.k, OSGN.l is signed based on a second identifier PID2 of the patient PAT, furthermore comprising:
- determining DET-PI2 an second identifier PID2 of the patient PAT being owner of the requested medical data record RMDR based on the distributed ownership ledger OLDG with the computation unit US.PU,
- transferring TRF-1 cryptocurrency from a first account to a second account with the computation unit US.CU, wherein the first account is related to the identifier REID of the requesting entity RE, and wherein the second account is related to the second identifier PID2 of the patient PAT.

Embodiment 27: The method according to claim 26, furthermore comprising:
- receiving REC-AI, by a trusted entity TE, an account information ACCI by the patient PAT being owner of the requested medical data record RMDR,
- transferring TRF-2 cryptocurrency from the second account to a third account based on the account information ACCI, wherein the third account is related to the trusted entity TE,
- initiating a payment from the trusted entity TE to the patient PAT.

Embodiment 28: A consent storage system PS for storing consent, comprising:
- an interface PS.IF, configured for receiving REC-MDR a medical data record MDR, MDR.j, MDR.k, MDR.l, wherein the medical data record MDR, MDR.j, MDR.k, MDR.l is related to a patient PAT, furthermore configured for receiving REC-AEID an identifier AEID, AEID.j, AEID.k, AEID.l of an authorized entity AE,
- a computation unit PS.CU, configured for determining DET-CI consent information CI, CI.j, CI.k, CI.l, wherein the consent information CI, CI.j, CI.k, CI.l is based on the medical data record MDR, MDR.j, MDR.k, MDR.l and the identifier AEID, AEID.j, AEID.k, AEID.l of the authorized entity AE, furthermore configured for documenting DOC-CI the consent information CI, CI.j, CI.k, CI.l in a distributed consent ledger CLDG with the computation unit PS.CU.

Embodiment 29: The consent storage system PS according to embodiment 28, furthermore configured for executing the method according to one of the embodiments 14 to 20.

Embodiment 30: A computer program product comprising program elements which induce a consent storage system PS to carry out the steps of the method for storing consent according to one of the embodiments 14 to 20, when the program elements are loaded into a memory unit PS.MU of the consent storage system PS.

Embodiment 31: A computer-readable medium, on which program code sections of a computer program are saved, the program code sections being loadable into and/or executable in a consent storage system PS to make the consent storage system PS execute the method for storing consent according to one of the embodiments 14 to 20, when the program code sections are executed in the consent storage system PS.

Embodiment 32: A consent usage system US for using consent information CI, CI.j, CI.k, CI.l stored in a distributed consent ledger CLDG according to the method according to one of the embodiments 14 to 20, comprising:
an interface US.IF, configured for receiving REC-UR an access request AR directed to a requested medical data record RMDR, wherein the requested medical data record RMDR is stored memory unit US.MU, and wherein the requested medical data record RMDR is related to a patient PAT,
a computation unit US.CU, configured for locating DET-CI a consent information CI, CI.j, CI.k, CI.l in the distributed consent ledger CLDG, wherein the consent information CI, CI.j, CI.k, CI.l is related to the requested medical data record RMDR, furthermore configured for performing a check CHK based on the consent information CI, CI.j, CI.k, CI.l whether the patient PAT consented to use the requested medical data record RMDR, furthermore configured, in case of a positive check, for processing PRC the requested medical data record RMDR.

Embodiment 33: The consent usage system US according to embodiment 32, furthermore configured for executing the method according to one of the embodiments 21 to 27.

Embodiment 34: A computer program product comprising program elements which induce a consent usage system US to carry out the steps of the method for using consent according to one of the embodiments 21 to 27, when the program elements are loaded into a memory unit US.MU of the consent usage system US.

Embodiment 35: A computer-readable medium, on which program code sections of a computer program are saved, the program code sections being loadable into and/or executable in a consent usage system US to make the consent usage system US execute the method for storing consent according to one of the embodiments 21 to 27, when the program code sections are executed in the consent usage system US.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The invention claimed is:

1. A method for providing a uniform resource locator, comprising:
receiving a medical data record via an interface, the medical data record being related to a patient;
receiving an identifier of an authorized entity, a first identifier of the patient, a second identifier of the patient, and usage information via the interface, the authorized entity being permitted to access the medical data record;
storing the medical data record via a memory unit;
forming the uniform resource locator, via a computation unit, the uniform resource locator including a location of the medical data record in the memory unit and an authorization token, the authorization token being based on the medical data record and the identifier of the authorized entity, the medical data record being accessible by following the uniform resource locator;
providing the uniform resource locator, via the interface, to the patient;
determining consent information related to consent of the patient to access the medical data record by the authorized entity via the computation unit, the consent information including a consent signature based on at least one of the medical data record and the identifier of the authorized entity, wherein the consent information is based on the first identifier of the patient, the usage information, and at least one of the medical data record and the identifier of the authorized entity and the consent signature is signed based on the first identifier of the patient;
documenting the consent information in a distributed consent ledger, via the computation unit;
unlocking access to the medical data record, via the computation unit, after the documenting the consent information in the distributed consent ledger;
determining ownership information via the computation unit, the ownership information including an ownership signature based on the medical data record, the ownership signature being signed based on the second identifier of the patient; and
documenting the ownership information in a distributed ownership ledger, via the computation unit, wherein the consent information includes a smart contract,
the smart contract regulates a transfer of cryptocurrency in event of a usage of the medical data record,
the cryptocurrency is transferred from a first account to a second account,
the first account is related to an entity using the medical data record, and
the second account is related to at least one of the first identifier of the patient or the second identifier of the patient.

2. The method of claim 1, further comprising:
receiving an access request directed to a requested medical data record, via the interface, the requested medical data record being stored within the memory unit and the access request being based on the uniform resource locator; and
providing the requested medical data record based on the access request, via the interface.

3. The method of claim 2, wherein the access request is initiated by a requesting entity and the method further comprises:
receiving an identifier of the requesting entity, via the interface; and
performing a first check as to whether the distributed consent ledger documents a consent information based on the requested medical data record and on the identifier of the requesting entity, via the computation unit, wherein the providing is only executed upon the first check performed being positive.

4. The method of claim 3, wherein
the method further comprises:
determining an ownership second identifier based on the distributed ownership ledger, via the computation unit,
transferring the cryptocurrency from the first account to the second account, via the computation unit, and wherein the second account is related to the ownership second identifier of the patient.

5. The method of claim 2, wherein
the method further comprises:
determining an ownership second identifier based on the distributed ownership ledger, via the computation unit, and transferring the cryptocurrency from the first account to the second account, via the computation unit.

6. The method of claim 5, further comprising:
receiving, from a trusted entity, an account information by the patient being owner of the requested medical data record;
transferring, by the trusted entity, the cryptocurrency from the second account to a third account based on the account information, wherein the third account is related to the trusted entity; and
initiating a payment from the trusted entity to the patient, by the trusted entity.

7. The method of claim 1, wherein the identifier of the authorized entity is a string variable identifying the authorized entity.

8. The method of claim 1, wherein the identifier of the authorized entity is at least a portion of a digital certificate identifying the authorized entity.

9. A providing system for providing a uniform resource locator, comprising:
an interface, configured to receive a medical data record, an identifier of an authorized entity, a first identifier of a patient, a second identifier of the patient, and usage information, the medical data record being related to the patient and the authorized entity being permitted to access the medical data record, and provide the uniform resource locator, via the interface, to the patient;
a memory unit configured to store the medical data record; and
a computation unit, configured to form the uniform resource locator, determine consent information related to consent of the patient to access the medical data record by the authorized entity, document the consent information in a distributed consent ledger, unlock access to the medical data record after the consent information is documented in the distributed consent ledger, determine ownership information, and document the ownership information in a distributed ownership ledger, wherein
the uniform resource locator includes a location of the medical data record in the memory unit and an authorization token,
the authorization token is based on the medical data record and the identifier of the authorized entity,
the medical data record is accessible by following the uniform resource locator,
the consent information includes a consent signature based on at least one of the medical data record and the identifier of the authorized entity,
the consent information is based on the first identifier of the patient, the usage information, and at least one of the medical data record and the identifier of the authorized entity and the consent signature is signed based on the first identifier of the patient,
the ownership information includes an ownership signature based on the medical data record,
the ownership signature is signed based on the second identifier of the patient,
the consent information includes a smart contract,
the smart contract regulates a transfer of cryptocurrency in event of a usage of the medical data record,
the cryptocurrency is transferred from a first account to a second account,
the first account is related to an entity using the medical data record, and
the second account is related to at least one of the first identifier of the patient or the second identifier of the patient.

10. A non-transitory computer readable medium storing program elements to induce a providing system to carry out a method for providing a uniform resource locator upon the program elements being executed by the providing system, the method comprising:
receiving a medical data record via an interface, the medical data record being related to a patient;
receiving an identifier of an authorized entity, a first identifier of the patient, a second identifier of the patient, and usage information via the interface, the authorized entity being permitted to access the medical data record;
storing the medical data record via a memory unit;
forming the uniform resource locator, via a computation unit, the uniform resource locator including a location of the medical data record in the memory unit and an authorization token, the authorization token being based on the medical data record and the identifier of the authorized entity, the medical data record being accessible by following the uniform resource locator;
providing the uniform resource locator, via the interface, to the patient;
determining consent information related to consent of the patient to access the medical data record by the authorized entity via the computation unit, the consent information including a consent signature based on at least one of the medical data record and the identifier of the authorized entity, wherein the consent information is based on the first identifier of the patient, the usage information, and at least one of the medical data record and the identifier of the authorized entity and the consent signature is signed based on the first identifier of the patient;
documenting the consent information in a distributed consent ledger, via the computation unit;
unlocking access to the medical data record, via the computation unit, after the documenting the consent information in the distributed consent ledger;
determining ownership information via the computation unit, the ownership information including an ownership signature based on the medical data record, the ownership signature being signed based on the second identifier of the patient; and
documenting the ownership information in a distributed ownership ledger, via the computation unit, wherein
the consent information includes a smart contract,
the smart contract regulates a transfer of cryptocurrency in event of a usage of the medical data record,
the cryptocurrency is transferred from a first account to a second account,
the first account is related to an entity using the medical data record, and
the second account is related to at least one of the first identifier of the patient or the second identifier of the patient.

* * * * *